(12) United States Patent
Watanabe et al.

(10) Patent No.: US 9,605,029 B2
(45) Date of Patent: Mar. 28, 2017

(54) ANTIBODY-BINDING PEPTIDE

(71) Applicant: NATIONAL INSTITUTE OF ADVANCED INDUSTRIAL SCIENCE AND TECHNOLOGY, Tokyo (JP)

(72) Inventors: Hideki Watanabe, Ibaraki (JP); Shinya Honda, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 14/763,589

(22) PCT Filed: Dec. 25, 2013

(86) PCT No.: PCT/JP2013/007583
§ 371 (c)(1),
(2) Date: Jul. 27, 2015

(87) PCT Pub. No.: WO2014/115229
PCT Pub. Date: Jul. 31, 2014

(65) Prior Publication Data
US 2015/0353608 A1 Dec. 10, 2015

(30) Foreign Application Priority Data

Jan. 28, 2013 (JP) .................... 2013-013217

(51) Int. Cl.
| | |
|---|---|
| C07K 14/00 | (2006.01) |
| C07K 7/06 | (2006.01) |
| C07K 7/08 | (2006.01) |
| G01N 33/68 | (2006.01) |
| C07K 16/42 | (2006.01) |

(52) U.S. Cl.
CPC .............. *C07K 14/001* (2013.01); *C07K 7/06* (2013.01); *C07K 7/08* (2013.01); *C07K 16/4208* (2013.01); *G01N 33/6854* (2013.01)

(58) Field of Classification Search
CPC .... C07K 14/001; C07K 16/4208; C07K 7/06; C07K 7/08; C07K 14/00; G01N 33/6854
USPC ..... 530/324, 325, 326, 327, 328; 435/235.1, 435/252.3, 252.33, 320.1
See application file for complete search history.

(56) References Cited

U.S. PATENT DOCUMENTS

2004/0037809 A1* 2/2004 Quay .................... A61K 9/0043
424/85.6
2010/0297606 A1 11/2010 Ito

FOREIGN PATENT DOCUMENTS

| | | |
|---|---|---|
| EP | 2 940 197 A1 | 11/2015 |
| JP | 2004187563 A | 7/2004 |
| JP | 2009112282 A | 5/2009 |
| WO | 0145746 A2 | 6/2001 |
| WO | 2008054030 A1 | 5/2008 |

OTHER PUBLICATIONS

Watanabe et al, "Tracing Primordial Protein Evolution through Structurally Guided Stepwise Segment Elongation", The Journal of Biological Chemistry, Feb. 7, 2014, vol. 289, No. 6, pp. 3394-3404 (12 pgs. total).
Watanabe et al., "Small artificial protein design using minute protein as components", The 13th Japan Protein Science Society Annual Meeting Program/Collection of Summaries, May 31, 2013, 5 pgs. total.
International Search Report dated Apr. 1, 2014, issued by the International Searching Authority in corresponding International Application No. PCT/JP2013/007583.
Bio-Pharmaceutical Handbook, From the manufacturing of Biologics to quality management, Ed. Bio-Virus Committee, PDA Japan Chapter, Jan. 25, 2014, Chapter 5, 11 pgs. total.
Watanabe et al., "Optimizing pH Response of Affinity between Protein G and IgG Fc: *How Electrostatic Modulations Affect Protein-Protein Interactions*", The Journal of Biological Chemistry, May 1, 2009, vol. 284, No. 18, pp. 12373-12383.
Park et al., "Fluorescence Polarization Assay to Quantify Protein—Protein Interactions", Methods in Molecular Biology, Humana Press Inc., Ed. Haian Fu, 2004, vol. 261, pp. 161-165 (7 pgs. total).
Wittig et al., "Native electrophoretic techniques to identify protein—protein interactions", Proteomics, 2009, vol. 9, pp. 5214-5223.
Brymora et al., "Protein-Protein Interactions Identified by Pull-Down Experiments and Mass Spectrometry", Current Protocols in Cell Biology, Supplement 22, 2004, Unit 17.5, 51 pgs. total.
Braisted et al., "Minimizing a binding domain from protein A", Proc. Natl. Acad. Sci. USA, Jun. 1996, vol. 93, pp. 5688-5692.
Joubert et al., "Highly Aggregated Antibody Therapeutics Can Enhance the in Vitro Innate and Late-stage T-cell Immune Responses", The Journal of Biological Chemistry, Jul. 20, 2012, vol. 287, No. 30, pp. 25266-25279 (15 pgs. total).
Luo et al., "Chemical Modifications in Therapeutic Protein Aggregates Generated under Different Stress Conditions", The Journal of Biological Chemistry, Jul. 15, 2011, vol. 286, No. 28, pp. 25134-25144 (12 pgs. total).
Yoshitake et al., "Conjugation of Glucose Oxidase from *Aspergillus niger* and Rabbit Antibodies Using N-Hydroxysuccinimide Ester of N-(4-Carboxycyclohexylmethyl)-Maleimide", Eur. J. Biochem., 1979, vol. 101, pp. 395-399.
Kanmert et al., "Thermal Induction of an Alternatively Folded State in Human IgG-Fc", Biochemistry, 2011, vol. 50, No. 6, pp. 981-988.
Pain, Folding of Proteins, Edition 2, Chapter 2, Department of Biochemistry and Molecular Biology, 2002, 10 pgs. total.

(Continued)

*Primary Examiner* — Julie Ha
(74) *Attorney, Agent, or Firm* — Sughrue Mion, PLLC

(57) ABSTRACT

Polypeptides which have binding activity to an Fc region of immunoglobulin G and can be favorably used in detecting, purifying, immobilizing or removing an antibody, immunoglobulin G or a protein containing an Fc region of immunoglobulin G, are described. Methods for detecting, purifying, immobilizing or removing an antibody, immunoglobulin G or a protein containing an Fc region of immunoglobulin G, by using the peptide, are also described.

11 Claims, 13 Drawing Sheets

(56) References Cited

OTHER PUBLICATIONS

Post sequence protein Experimental Method 3, The basis of structure/function analysis, Ed. Y. Oshima, K. Suzui, Y. Fujii, and T. Muramatsu, 2002, 41 pgs. total.
Feige et al., "Dissecting the Alternatively Folded State of the Antibody Fab Fragment", J. Mol. Biol., 2010, vol. 399, pp. 719-730.
Thies et al., "The Alternatively Folded State of the Antibody $C_H3$ Domain", J. Mol. Biol., 2001, vol. 309, pp. 1077-1085.
Kanno et al., "Assembling of engineered IgG-binding protein on gold surface for highly oriented antibody immobilization", Journal of Biotechnology, 2000, vol. 76, pp. 207-214.
Hober et al., "Protein A chromatography for antibody purification", Journal of Chromatography B, 2007, vol. 848, pp. 40-47.
Buchner et al., "Alternatively Folded States of an Immunoglobulin", Biochemistry, 1991, vol. 30, No. 28, pp. 6922-6929.
Rosenberg, "Effects of Protein Aggregates: An Immunologic Perspective", The AAPS Journal, 2006, vol. 8, No. 3, Article 59, pp. E501-E507.
Berkowitz et al., "Analytical tools for characterizing biopharmaceuticals and the implications for biosimilars", Nat Rev Drug Discov., 2013, vol. 11, No. 7, pp. 527-540 (pp. 1-26).
Sakamoto et al., "Discovery and Characterization of a Peptide Motif That Specifically Recognizes a Non-native Conformation of Human IgG Induced by Acidic pH Conditions", The Journal of Biological Chemistry, Apr. 10, 2009, vol. 284, No. 15, pp. 9986-9993 (9 pgs. total).
Verdoliva et al., "A New Ligand for Immunoglobulin G Subdomains by Screening of a Synthetic Peptide Library", ChemBioChem, 2005, vol. 6, pp. 1242-1253.
Development and market of antibody Drugs, Jul. 2, 2012:CMC Publishing Co., Ltd. Ed. M. Iguchi and E. Kurata, pp. 59-66.
Ehrlich et al., "Identification of peptides that bind to the constant region of a humanized $IgG_1$ monoclonal antibody using phage display", Journal of Molecular Recognition, 1998, vol. 11, pp. 121-125.
Fassina et al., "Immunoglobulin specificity of TG19318: a novel synthetic ligand for antibody affinity purification", Journal of Molecular Recognition, 1998, vol. 11, pp. 128-133.
Krook et al., "Novel peptides binding to the Fc-portion of immunoglobulins obtained from a combinatorial phage display peptide library", Journal of Immunological Methods, 1998, vol. 221, pp. 151-157.
DeLano et al., "Convergent Solutions to Binding at a Protein-Protein Interface", Science, Feb. 18, 2000, vol. 287, pp. 1279-1283 (6 pgs. total).
CMC research/application and ensuring equivalence in bio/antibody pharmaceutical and subsequent products, Aug. 29, 2011: Edition 1, first printing issued, http://www.science-t.com/, ISBN978-4-86428-026-6 C3047, 7 pgs. total.
Fassina et al., "Protein A Mimetic Peptide Ligand for Affinity Purification of Antibodies", Journal of Molecular Recognition, 1996, vol. 9, pp. 564-569.
Shirvill, "Preclinical Development of Monoclonal Antibodies and Related Biologicals", Business Insights, 2010, pp. 15-20, 8 pgs. total.
Dias et al., "Protein Ligand Design: From Phage Display to Synthetic Protein Epitope Mimetics in Human Antibody Fc-Binding Peptidomimetics", J. Am. Chem. Soc., 2006, vol. 128, No. 8, pp. 2726-2732.
Communication, dated Jun. 6, 2016, issued by the European Patent Office in corresponding European Patent Application No. 13873013.0.

\* cited by examiner (A)  (B)

(A)

(B)

SEQUENCE LISTING

```
<160> NUMBER OF SEQ ID NOS: 183

<210> SEQ ID NO 1
<211> LENGTH: 12
<212> TYPE: PRT
<213> ORGANISM: Artificial Sequence
<220> FEATURE:
<223> OTHER INFORMATION: IgG binding peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa is Ile or Leu

<400> SEQUENCE: 1

Tyr Asp Pro Xaa Thr Gly Thr Trp Arg Ser Xaa Xaa
1               5                   10

<210> SEQ ID NO 2
<211> LENGTH: 17
<212> TYPE: PRT
```

-continued

```
<213> ORGANISM: Artificial Sequence
<220> FEATURE:
<223> OTHER INFORMATION: IgG binding peptide, H6

<400> SEQUENCE: 2

Tyr Asp Pro Arg Thr Gly Thr Trp Arg Ser Ser Ile Ala Tyr Gly Gly
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: IgG binding peptide, H3

<400> SEQUENCE: 3

Tyr Asp Pro Gly Thr Gly Thr Trp Arg Ser Tyr Leu Arg Phe Gly Gly
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: IgG binding peptide, D5

<400> SEQUENCE: 4

Tyr Asp Pro Tyr Thr Gly Thr Trp Arg Ser Ser Ile Trp Val Leu Ser
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: IgG binding peptide, E7

<400> SEQUENCE: 5

Tyr Asp Pro Gly Thr Gly Thr Trp Arg Ser Trp Leu Ser Phe Asn Val
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: IgG binding peptide, sC12

<400> SEQUENCE: 6

Tyr Asp Pro Trp Thr Gly Thr Trp Arg Ser Phe Ile Trp Gly Gly Gly
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: IgG binding peptide, G3
```

```
<400> SEQUENCE: 7

Tyr Asp Pro Arg Thr Gly Thr Trp Leu Leu Tyr Ala Ser Arg Leu Leu
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: IgG binding peptide, G11

<400> SEQUENCE: 8

Tyr Asp Pro Val Thr Gly Thr Trp Thr Ser Ser Ile Ala Ser Trp Met
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: IgG binding peptide, sA7

<400> SEQUENCE: 9

Tyr Asp Pro Arg Thr Gly Thr Trp Arg Arg Ser Ser Leu Ser Tyr Ser
1               5                   10                  15

Gly

<210> SEQ ID NO 10
<211> LENGTH: 21
<212> TYPE: PRT
<213> ORGANISM: Artificial Sequence
<220> FEATURE:
<223> OTHER INFORMATION: IgG binding peptide
<220> FEATURE:
<221> NAME/KEY: misc_feature
<222> LOCATION: (2)..(2)
<223> OTHER INFORMATION: Xaa is Arg, Gln, or Ser
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa is Gly or Ser

<400> SEQUENCE: 10

Arg Xaa Xaa Xaa Xaa Tyr Asp Pro Arg Thr Gly Thr Trp Arg Ser Ser
1               5                   10                  15

Ile Ala Tyr Gly Gly
            20

<210> SEQ ID NO 11
<211> LENGTH: 25
<212> TYPE: PRT
<213> ORGANISM: Artificial Sequence
<220> FEATURE:
<223> OTHER INFORMATION: IgG binding peptide, 2A1

<400> SEQUENCE: 11

Gly Val Val Arg Gln Trp Ser Gly Tyr Asp Pro Arg Thr Gly Thr Trp
1               5                   10                  15

Arg Ser Ser Ile Ala Tyr Gly Gly Gly
```

```
            20                  25

<210> SEQ ID NO 12
<211> LENGTH: 25
<212> TYPE: PRT
<213> ORGANISM: Artificial Sequence
<220> FEATURE:
<223> OTHER INFORMATION: IgG binding peptide, 2A4

<400> SEQUENCE: 12

Ala Gly Ser Arg Arg Ala His Gly Tyr Asp Pro Arg Thr Gly Thr Trp
1               5                   10                  15

Arg Ser Ser Ile Ala Tyr Gly Gly Gly
            20                  25

<210> SEQ ID NO 13
<211> LENGTH: 25
<212> TYPE: PRT
<213> ORGANISM: Artificial Sequence
<220> FEATURE:
<223> OTHER INFORMATION: IgG binding peptide, 2F12

<400> SEQUENCE: 13

Ala Ser Val Arg Ser Trp Ser Ser Tyr Asp Pro Arg Thr Gly Thr Trp
1               5                   10                  15

Arg Ser Ser Ile Ala Tyr Gly Gly Gly
            20                  25

<210> SEQ ID NO 14
<211> LENGTH: 25
<212> TYPE: PRT
<213> ORGANISM: Artificial Sequence
<220> FEATURE:
<223> OTHER INFORMATION: IgG binding peptide, 2H1

<400> SEQUENCE: 14

Ser Trp Arg Arg Arg Gly Ser Ser Tyr Asp Pro Arg Thr Gly Thr Trp
1               5                   10                  15

Arg Ser Ser Ile Ala Tyr Gly Gly Gly
            20                  25

<210> SEQ ID NO 15
<211> LENGTH: 25
<212> TYPE: PRT
<213> ORGANISM: Artificial Sequence
<220> FEATURE:
<223> OTHER INFORMATION: IgG binding peptide, 2F2

<400> SEQUENCE: 15

Thr Gly Arg Gly Arg Ser Ala Arg Tyr Asp Pro Arg Thr Gly Thr Trp
1               5                   10                  15

Arg Ser Ser Ile Ala Tyr Gly Gly Gly
            20                  25

<210> SEQ ID NO 16
<211> LENGTH: 25
<212> TYPE: PRT
<213> ORGANISM: Artificial Sequence
<220> FEATURE:
<223> OTHER INFORMATION: IgG binding peptide, 2F4

<400> SEQUENCE: 16

His Trp Val Asn Gly Arg Ser Gly Tyr Asp Pro Arg Thr Gly Thr Trp
1               5                   10                  15
```

```
Arg Ser Ser Ile Ala Tyr Gly Gly Gly
            20                  25

<210> SEQ ID NO 17
<211> LENGTH: 25
<212> TYPE: PRT
<213> ORGANISM: Artificial Sequence
<220> FEATURE:
<223> OTHER INFORMATION: IgG binding peptide, 2F6

<400> SEQUENCE: 17

Glu Arg Trp Ile Thr Trp Ser Gly Tyr Asp Pro Arg Thr Gly Thr Trp
1               5                   10                  15

Arg Ser Ser Ile Ala Tyr Gly Gly Gly
            20                  25

<210> SEQ ID NO 18
<211> LENGTH: 25
<212> TYPE: PRT
<213> ORGANISM: Artificial Sequence
<220> FEATURE:
<223> OTHER INFORMATION: IgG binding peptide, 2F7

<400> SEQUENCE: 18

Gly Ser Val Val Arg Trp Arg Gly Tyr Asp Pro Arg Thr Gly Thr Trp
1               5                   10                  15

Arg Ser Ser Ile Ala Tyr Gly Gly Gly
            20                  25

<210> SEQ ID NO 19
<211> LENGTH: 25
<212> TYPE: PRT
<213> ORGANISM: Artificial Sequence
<220> FEATURE:
<223> OTHER INFORMATION: IgG binding peptide, 2F9

<400> SEQUENCE: 19

Gly Ala Val Tyr Arg Arg Ser Phe Tyr Asp Pro Arg Thr Gly Thr Trp
1               5                   10                  15

Arg Ser Ser Ile Ala Tyr Arg Gly Gly
            20                  25

<210> SEQ ID NO 20
<211> LENGTH: 24
<212> TYPE: PRT
<213> ORGANISM: Artificial Sequence
<220> FEATURE:
<223> OTHER INFORMATION: IgG binding peptide
<220> FEATURE:
<221> NAME/KEY: misc_feature
<222> LOCATION: (9)..(16)
<223> OTHER INFORMATION: Xaa can be any naturally occurring amino acid

<400> SEQUENCE: 20

Gly Val Val Arg Gln Trp Ser Gly Xaa Xaa Xaa Xaa Xaa Xaa Xaa Xaa
1               5                   10                  15

Arg Ser Ser Ile Ala Tyr Gly Gly
            20

<210> SEQ ID NO 21
<211> LENGTH: 25
<212> TYPE: PRT
<213> ORGANISM: Artificial Sequence
<220> FEATURE:
<223> OTHER INFORMATION: IgG binding peptide, 2A1Gly
```

-continued

```
<400> SEQUENCE: 21

Gly Val Val Arg Gln Trp Ser Gly Gly Gly Ser Gly Gly Gly Gly
1               5                   10                  15

Arg Ser Ser Ile Ala Tyr Gly Gly Gly
            20                  25

<210> SEQ ID NO 22
<211> LENGTH: 9
<212> TYPE: PRT
<213> ORGANISM: Artificial Sequence
<220> FEATURE:
<223> OTHER INFORMATION: IgG binding peptide, RSS

<400> SEQUENCE: 22

Arg Ser Ser Ile Ala Tyr Gly Gly Gly
1               5

<210> SEQ ID NO 23
<211> LENGTH: 29
<212> TYPE: PRT
<213> ORGANISM: Artificial Sequence
<220> FEATURE:
<223> OTHER INFORMATION: IgG binding peptide
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid

<400> SEQUENCE: 23

Asp Ala Ala Trp His Leu Gly Glu Leu Val Trp Ala Thr Tyr Tyr Asp
1               5                   10                  15

Pro Glu Thr Gly Thr Trp Xaa Pro Asp Trp Xaa Xaa Met
            20                  25

<210> SEQ ID NO 24
<211> LENGTH: 32
<212> TYPE: PRT
<213> ORGANISM: Artificial Sequence
<220> FEATURE:
<223> OTHER INFORMATION: IgG binding peptide, pep14

<400> SEQUENCE: 24

Asp Ala Ala Trp His Leu Gly Glu Leu Val Trp Ala Thr Tyr Tyr Asp
1               5                   10                  15

Pro Glu Thr Gly Thr Trp Gln Pro Asp Trp Leu Tyr Met Thr Thr Arg
            20                  25                  30

<210> SEQ ID NO 25
<211> LENGTH: 32
<212> TYPE: PRT
<213> ORGANISM: Artificial Sequence
<220> FEATURE:
<223> OTHER INFORMATION: IgG binding peptide, pep11

<400> SEQUENCE: 25

Asp Ala Ala Trp His Leu Gly Glu Leu Val Trp Ala Thr Tyr Tyr Asp
1               5                   10                  15

Pro Glu Thr Gly Thr Trp Ala Pro Asp Trp Arg Leu Met Gln Gly Gln
            20                  25                  30

<210> SEQ ID NO 26
```

```
<211> LENGTH: 32
<212> TYPE: PRT
<213> ORGANISM: Artificial Sequence
<220> FEATURE:
<223> OTHER INFORMATION: IgG binding peptide, pep21

<400> SEQUENCE: 26

Asp Ala Ala Trp His Leu Gly Glu Leu Val Trp Ala Thr Tyr Tyr Asp
1               5                   10                  15

Pro Glu Thr Gly Thr Trp Leu Pro Asp Trp Gln Thr Met Ala Gln Lys
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: IgG binding peptide, pep24

<400> SEQUENCE: 27

Asp Ala Ala Trp His Leu Gly Glu Leu Val Trp Ala Thr Tyr Tyr Asp
1               5                   10                  15

Pro Glu Thr Gly Thr Trp Glu Pro Asp Trp Gln Arg Met Leu Gly Gln
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: IgG binding peptide, pep3

<400> SEQUENCE: 28

Asp Ala Ala Trp His Leu Gly Glu Leu Val Trp Ala Thr Tyr Tyr Asp
1               5                   10                  15

Pro Glu Thr Gly Thr Trp Gln Pro Asp Trp Arg Ala Met Ser Gly Arg
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: IgG binding peptide, pep9

<400> SEQUENCE: 29

Asp Ala Ala Trp His Leu Gly Glu Leu Val Trp Ala Thr Tyr Tyr Asp
1               5                   10                  15

Pro Glu Thr Gly Thr Trp Arg Pro Asp Trp Lys Trp Met Ser Thr His
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: IgG binding peptide, pep7

<400> SEQUENCE: 30

Asp Ala Ala Trp His Leu Gly Glu Leu Val Trp Ala Thr Tyr Tyr Asp
1               5                   10                  15

Pro Glu Thr Gly Thr Trp Glu Pro Asp Trp Lys Leu Met Gln Arg Pro
            20                  25                  30
```

```
<210> SEQ ID NO 31
<211> LENGTH: 32
<212> TYPE: PRT
<213> ORGANISM: Artificial Sequence
<220> FEATURE:
<223> OTHER INFORMATION: IgG binding peptide, pep25

<400> SEQUENCE: 31

Asp Ala Ala Trp His Leu Gly Glu Leu Val Trp Ala Thr Tyr Tyr Asp
1               5                   10                  15

Pro Glu Thr Gly Thr Trp Gln Pro Asp Trp Asp Ile Met Ala Gly His
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: IgG binding peptide, pep27

<400> SEQUENCE: 32

Asp Ala Ala Trp His Leu Gly Glu Leu Val Trp Ala Thr Tyr Tyr Asp
1               5                   10                  15

Pro Glu Thr Gly Thr Trp Leu Pro Asp Trp Asp Val Met Val Arg Gln
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: IgG binding peptide, pep31

<400> SEQUENCE: 33

Asp Ala Ala Trp His Leu Gly Glu Leu Val Trp Ala Thr Tyr Tyr Asp
1               5                   10                  15

Pro Glu Thr Gly Thr Trp Val Pro Asp Trp Glu Arg Met Lys Gln His
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: IgG binding peptide, pep1

<400> SEQUENCE: 34

Asp Ala Ala Trp His Leu Gly Glu Leu Val Trp Ala Thr Tyr Tyr Asp
1               5                   10                  15

Pro Glu Thr Gly Thr Trp Glu Pro Asp Trp Ser Lys Met Arg Pro Gln
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: IgG binding peptide, pep2

<400> SEQUENCE: 35

Asp Ala Ala Trp His Leu Gly Glu Leu Val Trp Ala Thr Tyr Tyr Asp
1               5                   10                  15

Pro Glu Thr Gly Thr Trp Arg Pro Asp Trp Ala Val Met Ala Thr Pro
            20                  25                  30
```

```
<210> SEQ ID NO 36
<211> LENGTH: 32
<212> TYPE: PRT
<213> ORGANISM: Artificial Sequence
<220> FEATURE:
<223> OTHER INFORMATION: IgG binding peptide, pep3

<400> SEQUENCE: 36

Asp Ala Ala Trp His Leu Gly Glu Leu Val Trp Ala Thr Tyr Tyr Asp
1               5                   10                  15

Pro Glu Thr Gly Thr Trp Lys Pro Asp Trp Arg Met Met Gly Val Pro
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: IgG binding peptide, pep4

<400> SEQUENCE: 37

Asp Ala Ala Trp His Leu Gly Glu Leu Val Trp Ala Thr Tyr Tyr Asp
1               5                   10                  15

Pro Glu Thr Gly Thr Trp Leu Pro Asp Trp Asp Tyr Met Ser Ser Lys
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: IgG binding peptide, pep5

<400> SEQUENCE: 38

Asp Ala Ala Trp His Leu Gly Glu Leu Val Trp Ala Thr Tyr Tyr Asp
1               5                   10                  15

Pro Glu Thr Gly Thr Trp Met Pro Asp Trp Asp Arg Met Leu Arg Arg
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: IgG binding peptide, pep6

<400> SEQUENCE: 39

Asp Ala Ala Trp His Leu Gly Glu Leu Val Trp Ala Thr Tyr Tyr Asp
1               5                   10                  15

Pro Glu Thr Gly Thr Trp Thr Pro Asp Trp Asn Ala Met Ser Gln Arg
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: IgG binding peptide, pep10

<400> SEQUENCE: 40

Asp Ala Ala Trp His Leu Gly Glu Leu Val Trp Ala Thr Tyr Tyr Asp
1               5                   10                  15

Pro Glu Thr Gly Thr Trp Gln Pro Asp Trp Lys Arg Met Thr Ser Arg
            20                  25                  30
```

<210> SEQ ID NO 41
<211> LENGTH: 32
<212> TYPE: PRT
<213> ORGANISM: Artificial Sequence
<220> FEATURE:
<223> OTHER INFORMATION: IgG binding peptide, pep12

<400> SEQUENCE: 41

Asp Ala Ala Trp His Leu Gly Glu Leu Val Trp Ala Thr Tyr Tyr Asp
1               5                   10                  15

Pro Glu Thr Gly Thr Trp Gln Pro Asp Trp Gly Arg Met Asn Ser Lys
            20                  25                  30

<210> SEQ ID NO 42
<211> LENGTH: 39
<212> TYPE: PRT
<213> ORGANISM: Artificial Sequence
<220> FEATURE:
<223> OTHER INFORMATION: IgG binding peptide, pep29

<400> SEQUENCE: 42

Asp Ala Ala Trp His Leu Gly Glu Leu Val Trp Ala Thr Tyr Tyr Asp
1               5                   10                  15

Pro Glu Thr Gly Thr Trp Ala Pro Asp Trp Asn Arg Met Arg Asp Phe
            20                  25                  30

Asn Arg Ser Phe Arg Glu Val
            35

<210> SEQ ID NO 43
<211> LENGTH: 32
<212> TYPE: PRT
<213> ORGANISM: Artificial Sequence
<220> FEATURE:
<223> OTHER INFORMATION: IgG binding peptide, pep15

<400> SEQUENCE: 43

Asp Ala Ala Trp His Leu Gly Glu Leu Val Trp Ala Thr Tyr Tyr Asp
1               5                   10                  15

Pro Glu Thr Gly Thr Trp Val Pro Asp Trp Asp Ala Met Ser Ser Arg
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: IgG binding peptide, pep16

<400> SEQUENCE: 44

Asp Ala Ala Trp His Leu Gly Glu Leu Val Trp Ala Thr Tyr Tyr Asp
1               5                   10                  15

Pro Glu Thr Gly Thr Trp Ile Pro Asp Trp Thr Arg Met Gln Thr Trp
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: IgG binding peptide, pep17

<400> SEQUENCE: 45

Asp Ala Ala Trp His Leu Gly Glu Leu Val Trp Ala Thr Tyr Tyr Asp

```
              1               5                  10                  15
Pro Glu Thr Gly Thr Trp Lys Pro Asp Trp Gln Arg Met Lys Leu His
                  20                  25                  30
```

<210> SEQ ID NO 46
<211> LENGTH: 32
<212> TYPE: PRT
<213> ORGANISM: Artificial Sequence
<220> FEATURE:
<223> OTHER INFORMATION: IgG binding peptide, pep18

<400> SEQUENCE: 46

```
Asp Ala Ala Trp His Leu Gly Glu Leu Val Trp Ala Thr Tyr Tyr Asp
1               5                  10                  15

Pro Glu Thr Gly Thr Trp Leu Pro Asp Trp Ser Gln Met Arg Pro Gln
                  20                  25                  30
```

<210> SEQ ID NO 47
<211> LENGTH: 32
<212> TYPE: PRT
<213> ORGANISM: Artificial Sequence
<220> FEATURE:
<223> OTHER INFORMATION: IgG binding peptide, pep19

<400> SEQUENCE: 47

```
Asp Ala Ala Trp His Leu Gly Glu Leu Val Trp Ala Thr Tyr Tyr Asp
1               5                  10                  15

Pro Glu Thr Gly Thr Trp Leu Pro Asp Trp Asp Thr Met Thr Pro Arg
                  20                  25                  30
```

<210> SEQ ID NO 48
<211> LENGTH: 32
<212> TYPE: PRT
<213> ORGANISM: Artificial Sequence
<220> FEATURE:
<223> OTHER INFORMATION: IgG binding peptide, pep20

<400> SEQUENCE: 48

```
Asp Ala Ala Trp His Leu Gly Glu Leu Val Trp Ala Thr Tyr Tyr Asp
1               5                  10                  15

Pro Glu Thr Gly Thr Trp Gln Pro Asp Trp Ser Val Met Lys Ser Leu
                  20                  25                  30
```

<210> SEQ ID NO 49
<211> LENGTH: 40
<212> TYPE: PRT
<213> ORGANISM: Artificial Sequence, pep22
<220> FEATURE:
<223> OTHER INFORMATION: IgG binding peptide

<400> SEQUENCE: 49

```
Asp Ala Ala Trp His Leu Gly Glu Leu Val Trp Ala Thr Tyr Tyr Asp
1               5                  10                  15

Pro Glu Thr Gly Thr Trp Val Pro Asp Trp Asp Thr Met His Ala Ala
                  20                  25                  30

Ile Asn Arg Ser Phe Arg Glu Val
            35                  40
```

<210> SEQ ID NO 50
<211> LENGTH: 32
<212> TYPE: PRT
<213> ORGANISM: Artificial Sequence
<220> FEATURE:
<223> OTHER INFORMATION: IgG binding peptide, pep23

```
<400> SEQUENCE: 50

Asp Ala Ala Trp His Leu Gly Glu Leu Val Trp Ala Thr Tyr Tyr Asp
1               5                   10                  15

Pro Glu Thr Gly Thr Trp Ile Pro Asp Trp Arg Ala Met Ser Gln Phe
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: IgG binding peptide, pep26

<400> SEQUENCE: 51

Asp Ala Ala Trp His Leu Gly Glu Leu Val Trp Ala Thr Tyr Tyr Asp
1               5                   10                  15

Pro Glu Thr Gly Thr Trp Leu Pro Asp Trp Asn Leu Met Gly Gln His
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: IgG binding peptide, pep28

<400> SEQUENCE: 52

Asp Ala Ala Trp His Leu Gly Glu Leu Val Trp Ala Thr Tyr Tyr Asp
1               5                   10                  15

Pro Glu Thr Gly Thr Trp Arg Pro Asp Trp Ala Arg Met Glu Pro Met
            20                  25                  30

<210> SEQ ID NO 53
<211> LENGTH: 40
<212> TYPE: PRT
<213> ORGANISM: Artificial Sequence
<220> FEATURE:
<223> OTHER INFORMATION: IgG binding peptide, pep29

<400> SEQUENCE: 53

Asp Ala Ala Trp His Leu Gly Glu Leu Val Trp Ala Thr Tyr Tyr Asp
1               5                   10                  15

Pro Glu Thr Gly Thr Trp Lys Pro Asp Trp Gln Val Met Ser Pro Val
            20                  25                  30

Ser Asn Arg Ser Phe Arg Glu Val
        35                  40

<210> SEQ ID NO 54
<211> LENGTH: 32
<212> TYPE: PRT
<213> ORGANISM: Artificial Sequence
<220> FEATURE:
<223> OTHER INFORMATION: IgG binding peptide, pep30

<400> SEQUENCE: 54

Asp Ala Ala Trp His Leu Gly Glu Leu Val Trp Ala Thr Tyr Tyr Asp
1               5                   10                  15

Pro Glu Thr Gly Thr Trp Gln Pro Asp Trp Glu Ile Met Arg Pro Phe
            20                  25                  30

<210> SEQ ID NO 55
<211> LENGTH: 31
```

```
<212> TYPE: PRT
<213> ORGANISM: Artificial Sequence
<220> FEATURE:
<223> OTHER INFORMATION: IgG binding peptide, pep11_2

<400> SEQUENCE: 55

Glu Ala Trp His Leu Gly Glu Leu Val Trp Ala Thr Tyr Tyr Asp Pro
1               5                   10                  15

Glu Thr Gly Thr Trp Arg Pro Asp Trp Ser Arg Met Ser Gly Arg
            20                  25                  30

<210> SEQ ID NO 56
<211> LENGTH: 44
<212> TYPE: PRT
<213> ORGANISM: Artificial Sequence
<220> FEATURE:
<223> OTHER INFORMATION: IgG binding peptide
<220> FEATURE:
<221> NAME/KEY: misc_feature
<222> LOCATION: (1)..(1)
<223> OTHER INFORMATION: Xaa is Arg, Gly, or Ser
<220> FEATURE:
<221> NAME/KEY: misc_feature
<222> LOCATION: (2)..(2)
<223> OTHER INFORMATION: Xaa is Ala, Gly, or Val
<220> FEATURE:
<221> NAME/KEY: misc_feature
<222> LOCATION: (3)..(3)
<223> OTHER INFORMATION: Xaa can be any naturally occurring amino acid

<400> SEQUENCE: 56

Xaa Xaa Xaa Tyr Asp Pro Glu Thr Gly Thr Trp Tyr Asp Ala Ala Trp
1               5                   10                  15

His Leu Gly Glu Leu Val Trp Ala Thr Tyr Tyr Asp Pro Glu Thr Gly
            20                  25                  30

Thr Trp Glu Pro Asp Trp Gln Arg Met Leu Gly Gln
        35                  40

<210> SEQ ID NO 57
<211> LENGTH: 54
<212> TYPE: PRT
<213> ORGANISM: Artificial Sequence
<220> FEATURE:
<223> OTHER INFORMATION: IgG binding peptide, p17

<400> SEQUENCE: 57

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30

Trp Ala Thr Tyr Tyr Asp Pro Glu Thr Gly Thr Trp Glu Pro Asp Trp
        35                  40                  45

Gln Arg Met Leu Gly Gln
    50

<210> SEQ ID NO 58
<211> LENGTH: 51
<212> TYPE: PRT
<213> ORGANISM: Artificial Sequence
<220> FEATURE:
<223> OTHER INFORMATION: IgG binding peptide, p6

<400> SEQUENCE: 58

Val Ile Ser Leu Gly Ser Asp Arg Gly Val Tyr Asp Pro Glu Thr Gly
1               5                   10                  15
```

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 59
<211> LENGTH: 51
<212> TYPE: PRT
<213> ORGANISM: Artificial Sequence
<220> FEATURE:
<223> OTHER INFORMATION: IgG binding peptide, p12

<400> SEQUENCE: 59

Ile Met Ser Val Asp Gly Ser Ser Ala Arg Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 60
<211> LENGTH: 51
<212> TYPE: PRT
<213> ORGANISM: Artificial Sequence
<220> FEATURE:
<223> OTHER INFORMATION: IgG binding peptide, p16

<400> SEQUENCE: 60

Val Asp Leu Arg Ala His Gly Gly Ala Val Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 61
<211> LENGTH: 51
<212> TYPE: PRT
<213> ORGANISM: Artificial Sequence
<220> FEATURE:
<223> OTHER INFORMATION: IgG binding peptide, p19

<400> SEQUENCE: 61

Trp Ser Arg Phe Ser Ser Arg Ser Val Ala Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 62
<211> LENGTH: 51
<212> TYPE: PRT

```
<213> ORGANISM: Artificial Sequence
<220> FEATURE:
<223> OTHER INFORMATION: IgG binding peptide, p36

<400> SEQUENCE: 62

Gly Asn Pro Ser Asp Ser Ala Ser Ala Trp Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 63
<211> LENGTH: 51
<212> TYPE: PRT
<213> ORGANISM: Artificial Sequence
<220> FEATURE:
<223> OTHER INFORMATION: IgG binding peptide, p2_2

<400> SEQUENCE: 63

Ser Asn Phe Val Arg Ser Pro Ser Ala Trp Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 64
<211> LENGTH: 51
<212> TYPE: PRT
<213> ORGANISM: Artificial Sequence
<220> FEATURE:
<223> OTHER INFORMATION: IgG binding peptide, p4

<400> SEQUENCE: 64

Ile Pro Tyr Gly Phe Pro Gly Arg Gly Glu Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 65
<211> LENGTH: 51
<212> TYPE: PRT
<213> ORGANISM: Artificial Sequence
<220> FEATURE:
<223> OTHER INFORMATION: IgG binding peptide, p5

<400> SEQUENCE: 65

Gly Pro Tyr Asn Ile Pro Asp Ser Ala Val Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
```

-continued

```
                35                  40                  45

Leu Gly Gln
    50

<210> SEQ ID NO 66
<211> LENGTH: 51
<212> TYPE: PRT
<213> ORGANISM: Artificial Sequence
<220> FEATURE:
<223> OTHER INFORMATION: IgG binding peptide, p13

<400> SEQUENCE: 66

Trp Pro Leu Asn Ala Pro Ser Ser Ala Phe Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 67
<211> LENGTH: 51
<212> TYPE: PRT
<213> ORGANISM: Artificial Sequence
<220> FEATURE:
<223> OTHER INFORMATION: IgG binding peptide, p14

<400> SEQUENCE: 67

Val Pro Pro Arg Phe Ser Ser Ser Ala Gln Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 68
<211> LENGTH: 51
<212> TYPE: PRT
<213> ORGANISM: Artificial Sequence
<220> FEATURE:
<223> OTHER INFORMATION: IgG binding peptide, p15_2

<400> SEQUENCE: 68

Phe Leu Val Gly Leu His Ala Gly Ala Val Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 69
<211> LENGTH: 51
<212> TYPE: PRT
<213> ORGANISM: Artificial Sequence
<220> FEATURE:
<223> OTHER INFORMATION: IgG binding peptide, p20
```

-continued

<400> SEQUENCE: 69

Val Val Arg Val Asp His Ser Ser Ala Val Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 70
<211> LENGTH: 51
<212> TYPE: PRT
<213> ORGANISM: Artificial Sequence
<220> FEATURE:
<223> OTHER INFORMATION: IgG binding peptide, p26

<400> SEQUENCE: 70

Trp Met Glu Phe Tyr Pro Gly Arg Gly Val Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 71
<211> LENGTH: 51
<212> TYPE: PRT
<213> ORGANISM: Artificial Sequence
<220> FEATURE:
<223> OTHER INFORMATION: IgG binding peptide, p27

<400> SEQUENCE: 71

Asp Gly Val Gly Pro Gly Ser Arg Gly Val Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 72
<211> LENGTH: 51
<212> TYPE: PRT
<213> ORGANISM: Artificial Sequence
<220> FEATURE:
<223> OTHER INFORMATION: IgG binding peptide, p28

<400> SEQUENCE: 72

Phe Val Ser Ser Leu Pro Asn Ser Ala Met Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 73
<211> LENGTH: 51
<212> TYPE: PRT
<213> ORGANISM: Artificial Sequence
<220> FEATURE:
<223> OTHER INFORMATION: IgG binding peptide

<400> SEQUENCE: 73

Gly Arg Ala Phe Ser Gly Ser Arg Arg Trp Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Ala Pro Asp Trp Arg Leu Met
        35                  40                  45

Gln Gly Gln
    50

<210> SEQ ID NO 74
<211> LENGTH: 51
<212> TYPE: PRT
<213> ORGANISM: Artificial Sequence
<220> FEATURE:
<223> OTHER INFORMATION: IgG binding peptide, p2

<400> SEQUENCE: 74

Val Met Ala Thr Glu Val Val Arg Gly Val Tyr Asp Pro Glu Thr Gly
1               5                   10                  15

Thr Trp Tyr Asp Ala Thr Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 75
<211> LENGTH: 51
<212> TYPE: PRT
<213> ORGANISM: Artificial Sequence
<220> FEATURE:
<223> OTHER INFORMATION: IgG binding peptide, p15

<400> SEQUENCE: 75

Met Met Val Arg Pro Pro Arg Leu Gly Val Tyr Asp Pro Glu Pro Gly
1               5                   10                  15

Thr Trp Tyr Asp Ala Thr Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 76
<211> LENGTH: 51
<212> TYPE: PRT
<213> ORGANISM: Artificial Sequence
<220> FEATURE:
<223> OTHER INFORMATION: IgG binding peptide, p24

<400> SEQUENCE: 76

Glu Arg His Leu Val Ser Asp Tyr Leu His Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 77
<211> LENGTH: 51
<212> TYPE: PRT
<213> ORGANISM: Artificial Sequence
<220> FEATURE:
<223> OTHER INFORMATION: IgG binding peptide, p25

<400> SEQUENCE: 77

Phe Ser Asp Leu Asp Ser Phe Gly Val Ser Tyr Asp Pro Glu Thr Gly
1               5                   10                  15

Thr Trp Tyr Asp Ala Ala Trp His Arg Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 78
<211> LENGTH: 51
<212> TYPE: PRT
<213> ORGANISM: Artificial Sequence
<220> FEATURE:
<223> OTHER INFORMATION: IgG binding peptide, p34

<400> SEQUENCE: 78

Leu Phe Asp Asn Lys Leu Lys His Ala Ser Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 79
<211> LENGTH: 51
<212> TYPE: PRT
<213> ORGANISM: Artificial Sequence
<220> FEATURE:
<223> OTHER INFORMATION: IgG binding peptide, p24_2

<400> SEQUENCE: 79

Gly Ser Cys Lys Phe Ser Ser Ser Cys His Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 80
<211> LENGTH: 51

<212> TYPE: PRT
<213> ORGANISM: Artificial Sequence
<220> FEATURE:
<223> OTHER INFORMATION: IgG binding peptide, p25_2

<400> SEQUENCE: 80

Leu Ile Pro Pro Gly Gly Ile Ser Pro Trp Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 81
<211> LENGTH: 51
<212> TYPE: PRT
<213> ORGANISM: Artificial Sequence
<220> FEATURE:
<223> OTHER INFORMATION: IgG binding peptide, p31

<400> SEQUENCE: 81

Leu Asn Asp Phe Leu Thr Pro Thr Ala Trp Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Leu Pro Asp Trp Gln Thr Met
        35                  40                  45

Ala Gln Lys
    50

<210> SEQ ID NO 82
<211> LENGTH: 182
<212> TYPE: PRT
<213> ORGANISM: Artificial Sequence
<220> FEATURE:
<223> OTHER INFORMATION: thioredoxin fusion protein, H6_trx

<400> SEQUENCE: 82

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Pro Pro Thr
            115                 120                 125

Pro Thr Pro Ser Ser Gly Ser Gly His His His His His Ser Ala
    130                 135                 140

Ala Leu Glu Val Leu Phe Gln Gly Pro Gly Tyr Gln Asp Pro Asn Ser

```
                145                 150                 155                 160
Gly Gly Gly Gly Ser Tyr Asp Pro Arg Thr Gly Thr Trp Arg Ser Ser
                    165                 170                 175

Ile Ala Tyr Gly Gly Gly
            180

<210> SEQ ID NO 83
<211> LENGTH: 190
<212> TYPE: PRT
<213> ORGANISM: Artificial Sequence
<220> FEATURE:
<223> OTHER INFORMATION: thioredoxin fusion protein, 2A1_trx

<400> SEQUENCE: 83

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Gly Val Val Arg Gln Trp Ser Gly Tyr Asp Pro
                165                 170                 175

Arg Thr Gly Thr Trp Arg Ser Ser Ile Ala Tyr Gly Gly Gly
            180                 185                 190

<210> SEQ ID NO 84
<211> LENGTH: 190
<212> TYPE: PRT
<213> ORGANISM: Artificial Sequence
<220> FEATURE:
<223> OTHER INFORMATION: thioredoxin fusion protein, 2A4 _trx

<400> SEQUENCE: 84

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80
```

```
Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His Ser Ala
    130                 135                 140

Ala Leu Glu Val Leu Phe Gln Gly Pro Gly Tyr Gln Asp Pro Asn Ser
145                 150                 155                 160

Gly Gly Gly Gly Ser Ala Gly Ser Arg Arg Ala His Gly Tyr Asp Pro
                165                 170                 175

Arg Thr Gly Thr Trp Arg Ser Ser Ile Ala Tyr Gly Gly Gly
            180                 185                 190

<210> SEQ ID NO 85
<211> LENGTH: 190
<212> TYPE: PRT
<213> ORGANISM: Artificial Sequence
<220> FEATURE:
<223> OTHER INFORMATION: thioredoxin fusion protein, 2F12_trx

<400> SEQUENCE: 85

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His Ser Ala
    130                 135                 140

Ala Leu Glu Val Leu Phe Gln Gly Pro Gly Tyr Gln Asp Pro Asn Ser
145                 150                 155                 160

Gly Gly Gly Gly Ser Ala Ser Val Arg Ser Trp Ser Ser Tyr Asp Pro
                165                 170                 175

Arg Thr Gly Thr Trp Arg Ser Ser Ile Ala Tyr Gly Gly Gly
            180                 185                 190

<210> SEQ ID NO 86
<211> LENGTH: 205
<212> TYPE: PRT
<213> ORGANISM: Artificial Sequence
<220> FEATURE:
<223> OTHER INFORMATION: thioredoxin fusion protein, p17_trx

<400> SEQUENCE: 86

Met Ser Asp Lys Ile Ile His Leu Thr Asp Asp Ser Phe Asp Thr Asp
1               5                   10                  15
```

-continued

```
Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
            85                  90                  95

Lys Gly Gln Leu Lys Glu Phe Leu Asp Ala Asn Leu Ala Gly Ser Gly
        100                 105                 110

Ser Gly His Thr Ser Gly Gly Gly Ser Asn Asn Asn Pro Pro Thr
    115                 120                 125

Pro Thr Pro Ser Ser Gly Ser Gly His His His His His His Ser Ala
130                 135                 140

Ala Leu Glu Val Leu Phe Gln Gly Pro Gly Ile Ser Ala Phe Ser Pro
145                 150                 155                 160

Gly Arg Gly Val Tyr Asp Pro Glu Thr Gly Thr Trp Tyr Asp Ala Ala
                165                 170                 175

Trp His Leu Gly Glu Leu Val Trp Ala Thr Tyr Tyr Asp Pro Glu Thr
            180                 185                 190

Gly Thr Trp Glu Pro Asp Trp Gln Arg Met Leu Gly Gln
        195                 200                 205

<210> SEQ ID NO 87
<211> LENGTH: 197
<212> TYPE: PRT
<213> ORGANISM: Artificial Sequence
<220> FEATURE:
<223> OTHER INFORMATION: thioredoxin fusion protein, pep14_trx

<400> SEQUENCE: 87

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
            85                  90                  95

Lys Gly Gln Leu Lys Glu Phe Leu Asp Ala Asn Leu Ala Gly Ser Gly
        100                 105                 110

Ser Gly His Thr Ser Gly Gly Gly Ser Asn Asn Asn Pro Pro Thr
    115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Asp Ala Ala Trp His Leu Gly Glu Leu Val Trp
                165                 170                 175
```

```
Ala Thr Tyr Tyr Asp Pro Glu Thr Gly Thr Trp Gln Pro Asp Trp Leu
            180                 185                 190

Tyr Met Thr Thr Arg
        195

<210> SEQ ID NO 88
<211> LENGTH: 197
<212> TYPE: PRT
<213> ORGANISM: Artificial Sequence
<220> FEATURE:
<223> OTHER INFORMATION: thioredoxin fusion protein, pep21_trx

<400> SEQUENCE: 88

Met Ser Asp Lys Ile Ile His Leu Thr Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His His Ser Ala
    130                 135                 140

Ala Leu Glu Val Leu Phe Gln Gly Pro Gly Tyr Gln Asp Pro Asn Ser
145                 150                 155                 160

Gly Gly Gly Gly Ser Asp Ala Ala Trp His Leu Gly Glu Leu Val Trp
                165                 170                 175

Ala Thr Tyr Tyr Asp Pro Glu Thr Gly Thr Trp Leu Pro Asp Trp Gln
            180                 185                 190

Thr Met Ala Gln Lys
        195

<210> SEQ ID NO 89
<211> LENGTH: 197
<212> TYPE: PRT
<213> ORGANISM: Artificial Sequence
<220> FEATURE:
<223> OTHER INFORMATION: thioredoxin fusion protein, pep24_trx

<400> SEQUENCE: 89

Met Ser Asp Lys Ile Ile His Leu Thr Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
```

```
                65                  70                  75                  80
Leu Phe Lys Asn Gly Glu Val Ala Ala Thr Lys Val Gly Ala Leu Ser
                85                  90                  95
Lys Gly Gln Leu Lys Glu Phe Leu Asp Ala Asn Leu Ala Gly Ser Gly
                100                 105                 110
Ser Gly His Thr Ser Gly Gly Gly Ser Asn Asn Asn Pro Pro Thr
                115                 120                 125
Pro Thr Pro Ser Ser Gly Ser Gly His His His His His Ser Ala
            130                 135                 140
Ala Leu Glu Val Leu Phe Gln Gly Pro Gly Tyr Gln Asp Pro Asn Ser
145                 150                 155                 160
Gly Gly Gly Gly Ser Asp Ala Ala Trp His Leu Gly Glu Leu Val Trp
                165                 170                 175
Ala Thr Tyr Tyr Asp Pro Glu Thr Gly Thr Trp Glu Pro Asp Trp Gln
                180                 185                 190
Arg Met Leu Gly Gln
            195

<210> SEQ ID NO 90
<211> LENGTH: 197
<212> TYPE: PRT
<213> ORGANISM: Artificial Sequence
<220> FEATURE:
<223> OTHER INFORMATION: thioredoxin fusion protein, pep3_trx

<400> SEQUENCE: 90

Met Ser Asp Lys Ile Ile His Leu Thr Asp Ser Phe Asp Thr Asp
1               5                   10                  15
Val Leu Lys Ala Asp Gly Ala Ile Leu Val Asp Phe Trp Ala Glu Trp
                20                  25                  30
Cys Gly Pro Cys Lys Met Ile Ala Pro Ile Leu Asp Glu Ile Ala Asp
            35                  40                  45
Glu Tyr Gln Gly Lys Leu Thr Val Ala Lys Leu Asn Ile Asp Gln Asn
        50                  55                  60
Pro Gly Thr Ala Pro Lys Tyr Gly Ile Arg Gly Ile Pro Thr Leu Leu
65                  70                  75                  80
Leu Phe Lys Asn Gly Glu Val Ala Ala Thr Lys Val Gly Ala Leu Ser
                85                  90                  95
Lys Gly Gln Leu Lys Glu Phe Leu Asp Ala Asn Leu Ala Gly Ser Gly
                100                 105                 110
Ser Gly His Thr Ser Gly Gly Gly Ser Asn Asn Asn Pro Pro Thr
            115                 120                 125
Pro Thr Pro Ser Ser Gly Ser Gly His His His His His Ser Ala
        130                 135                 140
Ala Leu Glu Val Leu Phe Gln Gly Pro Gly Tyr Gln Asp Pro Asn Ser
145                 150                 155                 160
Gly Gly Gly Gly Ser Asp Ala Ala Trp His Leu Gly Glu Leu Val Trp
                165                 170                 175
Ala Thr Tyr Tyr Asp Pro Glu Thr Gly Thr Trp Gln Pro Asp Trp Arg
                180                 185                 190
Ala Met Ser Gly Arg
            195

<210> SEQ ID NO 91
<211> LENGTH: 197
<212> TYPE: PRT
```

<213> ORGANISM: Artificial Sequence
<220> FEATURE:
<223> OTHER INFORMATION: thioredoxin fusion protein, pep9_trx

<400> SEQUENCE: 91

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Asp Ala Ala Trp His Leu Gly Glu Leu Val Trp
                165                 170                 175

Ala Thr Tyr Tyr Asp Pro Glu Thr Gly Thr Trp Arg Pro Asp Trp Lys
            180                 185                 190

Trp Met Ser Thr His
            195

<210> SEQ ID NO 92
<211> LENGTH: 197
<212> TYPE: PRT
<213> ORGANISM: Artificial Sequence
<220> FEATURE:
<223> OTHER INFORMATION: thioredoxin fusion protein, pep7_trx

<400> SEQUENCE: 92

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His Ser Ala
        130                 135                 140

Ala Leu Glu Val Leu Phe Gln Gly Pro Gly Tyr Gln Asp Pro Asn Ser
145                 150                 155                 160

Gly Gly Gly Gly Ser Asp Ala Ala Trp His Leu Gly Glu Leu Val Trp
                165                 170                 175

Ala Thr Tyr Tyr Asp Pro Glu Thr Gly Thr Trp Glu Pro Asp Trp Lys
            180                 185                 190

Leu Met Gln Arg Pro
        195

<210> SEQ ID NO 93
<211> LENGTH: 197
<212> TYPE: PRT
<213> ORGANISM: Artificial Sequence
<220> FEATURE:
<223> OTHER INFORMATION: thioredoxin fusion protein, pep25_trx

<400> SEQUENCE: 93

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His Ser Ala
        130                 135                 140

Ala Leu Glu Val Leu Phe Gln Gly Pro Gly Tyr Gln Asp Pro Asn Ser
145                 150                 155                 160

Gly Gly Gly Gly Ser Asp Ala Ala Trp His Leu Gly Glu Leu Val Trp
                165                 170                 175

Ala Thr Tyr Tyr Asp Pro Glu Thr Gly Thr Trp Gln Pro Asp Trp Asp
            180                 185                 190

Ile Met Ala Gly His
        195

<210> SEQ ID NO 94
<211> LENGTH: 197
<212> TYPE: PRT
<213> ORGANISM: Artificial Sequence
<220> FEATURE:
<223> OTHER INFORMATION: thioredoxin fusion protein, pep27_trx

<400> SEQUENCE: 94

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

```
Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
 50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Asp Ala Ala Trp His Leu Gly Glu Leu Val Trp
                165                 170                 175

Ala Thr Tyr Tyr Asp Pro Glu Thr Gly Thr Trp Leu Pro Asp Trp Asp
            180                 185                 190

Val Met Val Arg Gln
            195

<210> SEQ ID NO 95
<211> LENGTH: 197
<212> TYPE: PRT
<213> ORGANISM: Artificial Sequence
<220> FEATURE:
<223> OTHER INFORMATION: thioredoxin fusion protein, pep31_trx

<400> SEQUENCE: 95

Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
 50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Asp Ala Ala Trp His Leu Gly Glu Leu Val Trp
                165                 170                 175

Ala Thr Tyr Tyr Asp Pro Glu Thr Gly Thr Trp Val Pro Asp Trp Glu
            180                 185                 190
```

-continued

```
Arg Met Lys Gln His
        195

<210> SEQ ID NO 96
<211> LENGTH: 216
<212> TYPE: PRT
<213> ORGANISM: Artificial Sequence
<220> FEATURE:
<223> OTHER INFORMATION: thioredoxin fusion protein

<400> SEQUENCE: 96

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Gly Arg Ala Phe Ser Gly Ser Arg Arg Trp Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Ala Pro
        195                 200                 205

Asp Trp Arg Leu Met Gln Gly Gln
    210                 215

<210> SEQ ID NO 97
<211> LENGTH: 216
<212> TYPE: PRT
<213> ORGANISM: Artificial Sequence
<220> FEATURE:
<223> OTHER INFORMATION: thioredoxin fusion protein, p2_trx

<400> SEQUENCE: 97

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
```

```
            65                  70                  75                  80
        Leu Phe Lys Asn Gly Glu Val Ala Ala Thr Lys Val Gly Ala Leu Ser
                        85                  90                  95

Lys Gly Gln Leu Lys Glu Phe Leu Asp Ala Asn Leu Ala Gly Ser Gly
                       100                 105                 110

Ser Gly His Thr Ser Gly Gly Gly Ser Asn Asn Asn Pro Pro Thr
                       115                 120                 125

Pro Thr Pro Ser Ser Gly Ser Gly His His His His His Ser Ala
        130                 135                 140

Ala Leu Glu Val Leu Phe Gln Gly Pro Gly Tyr Gln Asp Pro Asn Ser
        145                 150                 155                 160

Gly Gly Gly Gly Ser Val Met Ala Thr Glu Val Arg Gly Val Tyr
                       165                 170                 175

Asp Pro Glu Thr Gly Thr Trp Tyr Asp Ala Thr Trp His Leu Gly Glu
                       180                 185                 190

Leu Val Trp Ala Thr Tyr Tyr Asp Pro Glu Thr Gly Thr Trp Glu Pro
                       195                 200                 205

Asp Trp Gln Arg Met Leu Gly Gln
        210                 215

<210> SEQ ID NO 98
<211> LENGTH: 216
<212> TYPE: PRT
<213> ORGANISM: Artificial Sequence
<220> FEATURE:
<223> OTHER INFORMATION: thioredoxin fusion protein, p6_trx

<400> SEQUENCE: 98

Met Ser Asp Lys Ile Ile His Leu Thr Asp Asp Ser Phe Asp Thr Asp
        1               5                   10                  15

Val Leu Lys Ala Asp Gly Ala Ile Leu Val Asp Phe Trp Ala Glu Trp
                        20                  25                  30

Cys Gly Pro Cys Lys Met Ile Ala Pro Ile Leu Asp Glu Ile Ala Asp
                        35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
        65                  70                  75                  80

Leu Phe Lys Asn Gly Glu Val Ala Ala Thr Lys Val Gly Ala Leu Ser
                        85                  90                  95

Lys Gly Gln Leu Lys Glu Phe Leu Asp Ala Asn Leu Ala Gly Ser Gly
                       100                 105                 110

Ser Gly His Thr Ser Gly Gly Gly Ser Asn Asn Asn Pro Pro Thr
                       115                 120                 125

Pro Thr Pro Ser Ser Gly Ser Gly His His His His His Ser Ala
        130                 135                 140

Ala Leu Glu Val Leu Phe Gln Gly Pro Gly Tyr Gln Asp Pro Asn Ser
        145                 150                 155                 160

Gly Gly Gly Gly Ser Val Ile Ser Leu Gly Ser Asp Arg Gly Val Tyr
                       165                 170                 175

Asp Pro Glu Thr Gly Thr Trp Tyr Asp Ala Ala Trp His Leu Gly Glu
                       180                 185                 190

Leu Val Trp Ala Thr Tyr Tyr Asp Pro Glu Thr Gly Thr Trp Glu Pro
                       195                 200                 205

Asp Trp Gln Arg Met Leu Gly Gln
```

```
            210                 215

<210> SEQ ID NO 99
<211> LENGTH: 216
<212> TYPE: PRT
<213> ORGANISM: Artificial Sequence
<220> FEATURE:
<223> OTHER INFORMATION: thioredoxin fusion protein, p12_trx

<400> SEQUENCE: 99

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Ile Met Ser Val Asp Gly Ser Ser Ala Arg Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
        195                 200                 205

Asp Trp Gln Arg Met Leu Gly Gln
    210                 215

<210> SEQ ID NO 100
<211> LENGTH: 216
<212> TYPE: PRT
<213> ORGANISM: Artificial Sequence
<220> FEATURE:
<223> OTHER INFORMATION: thioredoxin fusion protein, p15_trx

<400> SEQUENCE: 100

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80
```

```
Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His Ser Ala
        130                 135                 140

Ala Leu Glu Val Leu Phe Gln Gly Pro Gly Tyr Gln Asp Pro Asn Ser
145                 150                 155                 160

Gly Gly Gly Gly Ser Met Met Val Arg Pro Pro Arg Leu Gly Val Tyr
                165                 170                 175

Asp Pro Glu Pro Gly Thr Trp Tyr Asp Ala Thr Trp His Leu Gly Glu
            180                 185                 190

Leu Val Trp Ala Thr Tyr Tyr Asp Pro Glu Thr Gly Thr Trp Glu Pro
            195                 200                 205

Asp Trp Gln Arg Met Leu Gly Gln
        210                 215

<210> SEQ ID NO 101
<211> LENGTH: 216
<212> TYPE: PRT
<213> ORGANISM: Artificial Sequence
<220> FEATURE:
<223> OTHER INFORMATION: thioredoxin fusion protein, p16_trx

<400> SEQUENCE: 101

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His Ser Ala
        130                 135                 140

Ala Leu Glu Val Leu Phe Gln Gly Pro Gly Tyr Gln Asp Pro Asn Ser
145                 150                 155                 160

Gly Gly Gly Gly Ser Val Asp Leu Arg Ala His Gly Gly Ala Val Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
            195                 200                 205

Asp Trp Gln Arg Met Leu Gly Gln
        210                 215
```

```
<210> SEQ ID NO 102
<211> LENGTH: 216
<212> TYPE: PRT
<213> ORGANISM: Artificial Sequence
<220> FEATURE:
<223> OTHER INFORMATION: thioredoxin fusion protein, p19_trx

<400> SEQUENCE: 102

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Trp Ser Arg Phe Ser Arg Ser Val Ala Tyr
                165                 170                 175

Asp Pro Glu Thr Gly Thr Trp Tyr Asp Ala Ala Trp His Leu Gly Glu
                180                 185                 190

Leu Val Trp Ala Thr Tyr Tyr Asp Pro Glu Thr Gly Thr Trp Glu Pro
            195                 200                 205

Asp Trp Gln Arg Met Leu Gly Gln
        210                 215

<210> SEQ ID NO 103
<211> LENGTH: 216
<212> TYPE: PRT
<213> ORGANISM: Artificial Sequence
<220> FEATURE:
<223> OTHER INFORMATION: thioredoxin fusion protein, p24_trx

<400> SEQUENCE: 103

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95
```

```
Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Glu Arg His Leu Val Ser Asp Tyr Leu His Tyr
                165                 170                 175

Asp Pro Glu Thr Gly Thr Trp Tyr Asp Ala Ala Trp His Leu Gly Glu
                180                 185                 190

Leu Val Trp Ala Thr Tyr Tyr Asp Pro Glu Thr Gly Thr Trp Glu Pro
                195                 200                 205

Asp Trp Gln Arg Met Leu Gly Gln
        210                 215

<210> SEQ ID NO 104
<211> LENGTH: 216
<212> TYPE: PRT
<213> ORGANISM: Artificial Sequence
<220> FEATURE:
<223> OTHER INFORMATION: thioredoxin fusion protein, p25_trx

<400> SEQUENCE: 104

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Phe Ser Asp Leu Asp Ser Phe Gly Val Ser Tyr
                165                 170                 175

Asp Pro Glu Thr Gly Thr Trp Tyr Asp Ala Ala Trp His Arg Gly Glu
                180                 185                 190

Leu Val Trp Ala Thr Tyr Tyr Asp Pro Glu Thr Gly Thr Trp Glu Pro
                195                 200                 205

Asp Trp Gln Arg Met Leu Gly Gln
        210                 215

<210> SEQ ID NO 105
```

<211> LENGTH: 216
<212> TYPE: PRT
<213> ORGANISM: Artificial Sequence
<220> FEATURE:
<223> OTHER INFORMATION: thioredoxin fusion protein, p34_trx

<400> SEQUENCE: 105

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Leu Phe Asp Asn Lys Leu Lys His Ala Ser Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
        195                 200                 205

Asp Trp Gln Arg Met Leu Gly Gln
    210                 215

<210> SEQ ID NO 106
<211> LENGTH: 216
<212> TYPE: PRT
<213> ORGANISM: Artificial Sequence
<220> FEATURE:
<223> OTHER INFORMATION: thioredoxin fusion protein, p36_trx

<400> SEQUENCE: 106

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly

```
                100             105             110
Ser Gly His Thr Ser Gly Gly Gly Ser Asn Asn Pro Pro Thr
            115             120             125
Pro Thr Pro Ser Ser Gly Ser Gly His His His His His Ser Ala
        130             135             140
Ala Leu Glu Val Leu Phe Gln Gly Pro Gly Tyr Gln Asp Pro Asn Ser
145             150             155             160
Gly Gly Gly Gly Ser Gly Asn Pro Ser Asp Ser Ala Ser Ala Trp Tyr
            165             170             175
Asp Pro Glu Thr Gly Thr Trp Tyr Asp Ala Ala Trp His Leu Gly Glu
        180             185             190
Leu Val Trp Ala Thr Tyr Tyr Asp Pro Glu Thr Gly Thr Trp Glu Pro
        195             200             205
Asp Trp Gln Arg Met Leu Gly Gln
        210             215

<210> SEQ ID NO 107
<211> LENGTH: 216
<212> TYPE: PRT
<213> ORGANISM: Artificial Sequence
<220> FEATURE:
<223> OTHER INFORMATION: thioredoxin fusion protein, p2_2_trx

<400> SEQUENCE: 107

Met Ser Asp Lys Ile Ile His Leu Thr Asp Asp Ser Phe Asp Thr Asp
1               5                   10                  15
Val Leu Lys Ala Asp Gly Ala Ile Leu Val Asp Phe Trp Ala Glu Trp
            20                  25                  30
Cys Gly Pro Cys Lys Met Ile Ala Pro Ile Leu Asp Glu Ile Ala Asp
        35                  40                  45
Glu Tyr Gln Gly Lys Leu Thr Val Ala Lys Leu Asn Ile Asp Gln Asn
    50                  55                  60
Pro Gly Thr Ala Pro Lys Tyr Gly Ile Arg Gly Ile Pro Thr Leu Leu
65                  70                  75                  80
Leu Phe Lys Asn Gly Glu Val Ala Ala Thr Lys Val Gly Ala Leu Ser
            85                  90                  95
Lys Gly Gln Leu Lys Glu Phe Leu Asp Ala Asn Leu Ala Gly Ser Gly
        100             105             110
Ser Gly His Thr Ser Gly Gly Gly Ser Asn Asn Asn Pro Pro Thr
            115             120             125
Pro Thr Pro Ser Ser Gly Ser Gly His His His His His His Ser Ala
        130             135             140
Ala Leu Glu Val Leu Phe Gln Gly Pro Gly Tyr Gln Asp Pro Asn Ser
145             150             155             160
Gly Gly Gly Gly Ser Ser Asn Phe Val Arg Ser Pro Ser Ala Trp Tyr
            165             170             175
Asp Pro Glu Thr Gly Thr Trp Tyr Asp Ala Ala Trp His Leu Gly Glu
        180             185             190
Leu Val Trp Ala Thr Tyr Tyr Asp Pro Glu Thr Gly Thr Trp Glu Pro
        195             200             205
Asp Trp Gln Arg Met Leu Gly Gln
        210             215

<210> SEQ ID NO 108
<211> LENGTH: 216
<212> TYPE: PRT
```

<213> ORGANISM: Artificial Sequence
<220> FEATURE:
<223> OTHER INFORMATION: thioredoxin fusion protein, p4_trx

<400> SEQUENCE: 108

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
                115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Ile Pro Tyr Gly Phe Pro Gly Arg Gly Glu Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
            195                 200                 205

Asp Trp Gln Arg Met Leu Gly Gln
210                 215
```

<210> SEQ ID NO 109
<211> LENGTH: 216
<212> TYPE: PRT
<213> ORGANISM: Artificial Sequence
<220> FEATURE:
<223> OTHER INFORMATION: thioredoxin fusion protein, p5_trx

<400> SEQUENCE: 109

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110
```

Ser Gly His Thr Ser Gly Gly Gly Ser Asn Asn Asn Pro Pro Thr
        115                 120                 125

Pro Thr Pro Ser Ser Gly Ser Gly His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Gly Pro Tyr Asn Ile Pro Asp Ser Ala Val Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
        195                 200                 205

Asp Trp Gln Arg Met Leu Gly Gln
    210                 215

<210> SEQ ID NO 110
<211> LENGTH: 216
<212> TYPE: PRT
<213> ORGANISM: Artificial Sequence
<220> FEATURE:
<223> OTHER INFORMATION: thioredoxin fusion protein, p13_trx

<400> SEQUENCE: 110

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Trp Pro Leu Asn Ala Pro Ser Ser Ala Phe Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
        195                 200                 205

Asp Trp Gln Arg Met Leu Gly Gln
    210                 215

<210> SEQ ID NO 111
<211> LENGTH: 216
<212> TYPE: PRT
<213> ORGANISM: Artificial Sequence
<220> FEATURE:

<223> OTHER INFORMATION: thioredoxin fusion protein, p14_trx

<400> SEQUENCE: 111

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His His Ser Ala
    130                 135                 140

Ala Leu Glu Val Leu Phe Gln Gly Pro Gly Tyr Gln Asp Pro Asn Ser
145                 150                 155                 160

Gly Gly Gly Gly Ser Val Pro Pro Arg Phe Ser Ser Ala Gln Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
            195                 200                 205

Asp Trp Gln Arg Met Leu Gly Gln
    210                 215

<210> SEQ ID NO 112
<211> LENGTH: 216
<212> TYPE: PRT
<213> ORGANISM: Artificial Sequence
<220> FEATURE:
<223> OTHER INFORMATION: thioredoxin fusion protein, p15_2_trx

<400> SEQUENCE: 112

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

```
Pro Thr Pro Ser Ser Gly Ser Gly His His His His His Ser Ala
        130                 135                 140

Ala Leu Glu Val Leu Phe Gln Gly Pro Gly Tyr Gln Asp Pro Asn Ser
145                 150                 155                 160

Gly Gly Gly Gly Ser Phe Leu Val Gly Leu His Ala Gly Ala Val Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
        195                 200                 205

Asp Trp Gln Arg Met Leu Gly Gln
        210                 215
```

<210> SEQ ID NO 113
<211> LENGTH: 216
<212> TYPE: PRT
<213> ORGANISM: Artificial Sequence
<220> FEATURE:
<223> OTHER INFORMATION: thioredoxin fusion protein, p20_trx

<400> SEQUENCE: 113

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His Ser Ala
        130                 135                 140

Ala Leu Glu Val Leu Phe Gln Gly Pro Gly Tyr Gln Asp Pro Asn Ser
145                 150                 155                 160

Gly Gly Gly Gly Ser Val Val Arg Val Asp His Ser Ser Ala Val Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
        195                 200                 205

Asp Trp Gln Arg Met Leu Gly Gln
        210                 215
```

<210> SEQ ID NO 114
<211> LENGTH: 216
<212> TYPE: PRT
<213> ORGANISM: Artificial Sequence
<220> FEATURE:
<223> OTHER INFORMATION: thioredoxin fusion protein, p24_2_trx -continued

<400> SEQUENCE: 114

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
            85                  90                  95

Lys Gly Gln Leu Lys Glu Phe Leu Asp Ala Asn Leu Ala Gly Ser Gly
        100                 105                 110

Ser Gly His Thr Ser Gly Gly Gly Ser Asn Asn Asn Pro Pro Thr
    115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Gly Ser Cys Lys Phe Ser Ser Cys His Tyr
            165                 170                 175

Asp Pro Glu Thr Gly Thr Trp Tyr Asp Ala Ala Trp His Leu Gly Glu
        180                 185                 190

Leu Val Trp Ala Thr Tyr Tyr Asp Pro Glu Thr Gly Thr Trp Glu Pro
    195                 200                 205

Asp Trp Gln Arg Met Leu Gly Gln
210                 215

<210> SEQ ID NO 115
<211> LENGTH: 216
<212> TYPE: PRT
<213> ORGANISM: Artificial Sequence
<220> FEATURE:
<223> OTHER INFORMATION: thioredoxin fusion protein, p25_2_trx

<400> SEQUENCE: 115

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
            85                  90                  95

Lys Gly Gln Leu Lys Glu Phe Leu Asp Ala Asn Leu Ala Gly Ser Gly
        100                 105                 110

Ser Gly His Thr Ser Gly Gly Gly Ser Asn Asn Asn Pro Pro Thr
    115                 120                 125

Pro Thr Pro Ser Ser Gly Ser Gly His His His His His His Ser Ala

```
                130                 135                 140
Ala Leu Glu Val Leu Phe Gln Gly Pro Gly Tyr Gln Asp Pro Asn Ser
145                 150                 155                 160

Gly Gly Gly Gly Ser Leu Ile Pro Pro Gly Gly Ile Ser Pro Trp Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
        195                 200                 205

Asp Trp Gln Arg Met Leu Gly Gln
    210                 215

<210> SEQ ID NO 116
<211> LENGTH: 216
<212> TYPE: PRT
<213> ORGANISM: Artificial Sequence
<220> FEATURE:
<223> OTHER INFORMATION: thioredoxin fusion protein, p26_trx

<400> SEQUENCE: 116

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Trp Met Glu Phe Tyr Pro Gly Arg Gly Val Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
        195                 200                 205

Asp Trp Gln Arg Met Leu Gly Gln
    210                 215

<210> SEQ ID NO 117
<211> LENGTH: 216
<212> TYPE: PRT
<213> ORGANISM: Artificial Sequence
<220> FEATURE:
<223> OTHER INFORMATION: thioredoxin fusion protein, p27_trx

<400> SEQUENCE: 117
```

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His Ser Ala
    130                 135                 140

Ala Leu Glu Val Leu Phe Gln Gly Pro Gly Tyr Gln Asp Pro Asn Ser
145                 150                 155                 160

Gly Gly Gly Gly Ser Asp Gly Val Pro Gly Ser Arg Gly Val Tyr
            165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
            195                 200                 205

Asp Trp Gln Arg Met Leu Gly Gln
210                 215
```

<210> SEQ ID NO 118
<211> LENGTH: 216
<212> TYPE: PRT
<213> ORGANISM: Artificial Sequence
<220> FEATURE:
<223> OTHER INFORMATION: thioredoxin fusion protein, p28_trx

<400> SEQUENCE: 118

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His Ser Ala
    130                 135                 140
```

Ala Leu Glu Val Leu Phe Gln Gly Pro Gly Tyr Gln Asp Pro Asn Ser
145                 150                 155                 160

Gly Gly Gly Gly Ser Phe Val Ser Ser Leu Pro Asn Ser Ala Met Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
        195                 200                 205

Asp Trp Gln Arg Met Leu Gly Gln
    210                 215

<210> SEQ ID NO 119
<211> LENGTH: 216
<212> TYPE: PRT
<213> ORGANISM: Artificial Sequence
<220> FEATURE:
<223> OTHER INFORMATION: thioredoxin fusion protein, p31_trx

<400> SEQUENCE: 119

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His His Ser Ala
    130                 135                 140

Ala Leu Glu Val Leu Phe Gln Gly Pro Gly Tyr Gln Asp Pro Asn Ser
145                 150                 155                 160

Gly Gly Gly Gly Ser Leu Asn Asp Phe Leu Thr Pro Thr Ala Trp Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Leu Pro
        195                 200                 205

Asp Trp Gln Thr Met Ala Gln Lys
    210                 215

<210> SEQ ID NO 120
<211> LENGTH: 546
<212> TYPE: DNA
<213> ORGANISM: Artificial Sequence
<220> FEATURE:
<223> OTHER INFORMATION: Oligo DNA

<400> SEQUENCE: 120
atgagcgata aaattattca cctgactgac gacagttttg acacggatgt actcaaagcg      60

```
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg gtaccagga tccgaattct    480 ggcggtggtg gcagctatga tccgcgtacc ggcacctggc gttcttctat tgcttatggt    540
gggggt                                                              546

<210> SEQ ID NO 121
<211> LENGTH: 570
<212> TYPE: DNA
<213> ORGANISM: Artificial Sequence
<220> FEATURE:
<223> OTHER INFORMATION: Oligo DNA

<400> SEQUENCE: 121
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg gtaccagga tccgaattct    480 ggcggtggtg gcagcgggt tgttaggcag tggagtgggt atgatccgcg taccggcacc    540
tggcgttctt ctattgctta tggtggggt                                     570

<210> SEQ ID NO 122
<211> LENGTH: 570
<212> TYPE: DNA
<213> ORGANISM: Artificial Sequence
<220> FEATURE:
<223> OTHER INFORMATION: Oligo DNA

<400> SEQUENCE: 122
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg gtaccagga tccgaattct    480 ggcggtggtg gcagcgcggg gtcgcggcgt gcacatgggt atgatccgcg taccggcacc    540
tggcgttctt ctattgctta tggtggggt                                     570
```

<210> SEQ ID NO 123
<211> LENGTH: 570
<212> TYPE: DNA
<213> ORGANISM: Artificial Sequence
<220> FEATURE:
<223> OTHER INFORMATION: Oligo DNA

<400> SEQUENCE: 123

| | | | | | |
|---|---|---|---|---|---|
| atgagcgata | aaattattca | cctgactgac | gacagttttg | acacggatgt | actcaaagcg | 60 |
| gacggggcga | tcctcgtcga | tttctgggca | gagtggtgcg | gtccgtgcaa | aatgatcgcc | 120 |
| ccgattctgg | atgaaatcgc | tgacgaatat | cagggcaaac | tgaccgttgc | aaaactgaac | 180 |
| atcgatcaaa | accctggcac | tgcgccgaaa | tatggcatcc | gtggtatccc | gactctgctg | 240 |
| ctgttcaaaa | acggtgaagt | ggcggcaacc | aaagtgggtg | cactgtctaa | aggtcagttg | 300 |
| aaagagttcc | tcgacgctaa | cctggccggt | tctggttctg | gccatactag | tggtggtggc | 360 |
| ggttctaata | caatcctcc | tactcctact | ccatctagtg | gttctggtca | tcaccatcac | 420 |
| catcactccg | cggctcttga | agtcctcttt | cagggacccg | ggtaccagga | tccgaattct | 480 |
| ggcggtggtg | gcagcgcttc | ggtgcggagt | tggtcgagtt | atgatccgcg | taccggcacc | 540 |
| tggcgttctt | ctattgctta | tggtggaggt | | | | 570 |

<210> SEQ ID NO 124
<211> LENGTH: 618
<212> TYPE: DNA
<213> ORGANISM: Artificial Sequence
<220> FEATURE:
<223> OTHER INFORMATION: Oligo DNA

<400> SEQUENCE: 124

| | | | | | |
|---|---|---|---|---|---|
| atgagcgata | aaattattca | cctgactgac | gacagttttg | acacggatgt | actcaaagcg | 60 |
| gacggggcga | tcctcgtcga | tttctgggca | gagtggtgcg | gtccgtgcaa | aatgatcgcc | 120 |
| ccgattctgg | atgaaatcgc | tgacgaatat | cagggcaaac | tgaccgttgc | aaaactgaac | 180 |
| atcgatcaaa | accctggcac | tgcgccgaaa | tatggcatcc | gtggtatccc | gactctgctg | 240 |
| ctgttcaaaa | acggtgaagt | ggcggcaacc | aaagtgggtg | cactgtctaa | aggtcagttg | 300 |
| aaagagttcc | tcgacgctaa | cctggccggt | tctggttctg | gccatactag | tggtggtggc | 360 |
| ggttctaata | caatcctcc | tactcctact | ccatctagtg | gttctggtca | tcaccatcac | 420 |
| catcactccg | cggctcttga | agtcctcttt | cagggacccg | gcattagtgc | gttttctccg | 480 |
| gggcgtgggg | tgtacgaccc | cgagacgggc | acgtggtacg | atgcagcgtg | gcatctggga | 540 |
| gaactggtgt | gggcaaccta | ttatgatccg | gaaaccggga | cctgggagcc | tgattggcag | 600 |
| aggatgctgg | ggcagtag | | | | | 618 |

<210> SEQ ID NO 125
<211> LENGTH: 591
<212> TYPE: DNA
<213> ORGANISM: Artificial Sequence
<220> FEATURE:
<223> OTHER INFORMATION: Oligo DNA

<400> SEQUENCE: 125

| | | | | | |
|---|---|---|---|---|---|
| atgagcgata | aaattattca | cctgactgac | gacagttttg | acacggatgt | actcaaagcg | 60 |
| gacggggcga | tcctcgtcga | tttctgggca | gagtggtgcg | gtccgtgcaa | aatgatcgcc | 120 |
| ccgattctgg | atgaaatcgc | tgacgaatat | cagggcaaac | tgaccgttgc | aaaactgaac | 180 |
| atcgatcaaa | accctggcac | tgcgccgaaa | tatggcatcc | gtggtatccc | gactctgctg | 240 |

```
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagcgatgc agcgtggcat ctgggcgaac tggtgtgggc aacctattat    540
gatccggaaa ccggcacctg gcagccggat tggttgtata tgactactcg g              591
```

<210> SEQ ID NO 126
<211> LENGTH: 591
<212> TYPE: DNA
<213> ORGANISM: Artificial Sequence
<220> FEATURE:
<223> OTHER INFORMATION: Oligo DNA

<400> SEQUENCE: 126

```
atgagcgata aaattattca cctgactgac gacagttttg acacggatgt actcaaagcg    60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagcgatgc agcgtggcat ctgggagaac tggtgtgggc aacctattat    540
gatccggaaa ccggcacctg gcttcctgat tggcagacga tggcgcagaa g              591
```

<210> SEQ ID NO 127
<211> LENGTH: 591
<212> TYPE: DNA
<213> ORGANISM: Artificial Sequence
<220> FEATURE:
<223> OTHER INFORMATION: Oligo DNA

<400> SEQUENCE: 127

```
atgagcgata aaattattca cctgactgac gacagttttg acacggatgt actcaaagcg    60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagcgatgc agcgtggcat ctgggagaac tggtgtgggc aacctattat    540
gatccggaaa ccggcacctg ggagcctgat tggcagagga tgctggggca g              591
```

<210> SEQ ID NO 128
<211> LENGTH: 591
<212> TYPE: DNA
<213> ORGANISM: Artificial Sequence
<220> FEATURE:
<223> OTHER INFORMATION: Oligo DNA

<400> SEQUENCE: 128

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gtaccagga tccgaattct   480
ggcggtggtg gcagcgatgc agcgtggcat ctgggcgaac tggtgtgggc aacctattat   540
gatccggaaa ccggcacctg caaccggat tggcgtgcga tgtcggggcg t            591
```

<210> SEQ ID NO 129
<211> LENGTH: 591
<212> TYPE: DNA
<213> ORGANISM: Artificial Sequence
<220> FEATURE:
<223> OTHER INFORMATION: Oligo DNA

<400> SEQUENCE: 129

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gtaccagga tccgaattct   480
ggcggtggtg gcagcgatgc agcgtggcat ctgggcgaac tggtgtgggc aacctattat   540
gatccggaaa ccggcacctg gcgtcctgat tggaagtgga tgagtactca t            591
```

<210> SEQ ID NO 130
<211> LENGTH: 591
<212> TYPE: DNA
<213> ORGANISM: Artificial Sequence
<220> FEATURE:
<223> OTHER INFORMATION: Oligo DNA

<400> SEQUENCE: 130

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gtaccagga tccgaattct   480
```

| | |
|---|---|
| ggcggtggtg gcagcgatgc agcgtggcat ctgggagaac tggtgtgggc aacctattat | 540 |
| gatccggaaa ccggcacctg ggagcctgat tggaagctta tgcagcggcc t | 591 |

<210> SEQ ID NO 131
<211> LENGTH: 591
<212> TYPE: DNA
<213> ORGANISM: Artificial Sequence
<220> FEATURE:
<223> OTHER INFORMATION: Oligo DNA

<400> SEQUENCE: 131

| | |
|---|---|
| atgagcgata aaattattca cctgactgac gacagttttg acacggatgt actcaaagcg | 60 |
| gacggggcga tcctcgtcga tttctgggca gagtggtgcg gtccgtgcaa aatgatcgcc | 120 |
| ccgattctgg atgaaatcgc tgacgaatat cagggcaaac tgaccgttgc aaaactgaac | 180 |
| atcgatcaaa accctggcac tgcgccgaaa tatggcatcc gtggtatccc gactctgctg | 240 |
| ctgttcaaaa acggtgaagt ggcggcaacc aaagtgggtg cactgtctaa aggtcagttg | 300 |
| aaagagttcc tcgacgctaa cctggccggt tctggttctg gccatactag tggtggtggc | 360 |
| ggttctaata acaatcctcc tactcctact ccatctagtg gttctggtca tcaccatcac | 420 |
| catcactccg cggctcttga agtcctcttt cagggacccg ggtaccagga tccgaattct | 480 |
| ggcggtggtg gcagcgatgc agcgtggcat ctgggagaac tggtgtgggc aacctattat | 540 |
| gatccggaaa ccggcacctg gcagcctgat tgggatatta tggctgggca t | 591 |

<210> SEQ ID NO 132
<211> LENGTH: 591
<212> TYPE: DNA
<213> ORGANISM: Artificial Sequence
<220> FEATURE:
<223> OTHER INFORMATION: Oligo DNA

<400> SEQUENCE: 132

| | |
|---|---|
| atgagcgata aaattattca cctgactgac gacagttttg acacggatgt actcaaagcg | 60 |
| gacggggcga tcctcgtcga tttctgggca gagtggtgcg gtccgtgcaa aatgatcgcc | 120 |
| ccgattctgg atgaaatcgc tgacgaatat cagggcaaac tgaccgttgc aaaactgaac | 180 |
| atcgatcaaa accctggcac tgcgccgaaa tatggcatcc gtggtatccc gactctgctg | 240 |
| ctgttcaaaa acggtgaagt ggcggcaacc aaagtgggtg cactgtctaa aggtcagttg | 300 |
| aaagagttcc tcgacgctaa cctggccggt tctggttctg gccatactag tggtggtggc | 360 |
| ggttctaata acaatcctcc tactcctact ccatctagtg gttctggtca tcaccatcac | 420 |
| catcactccg cggctcttga agtcctcttt cagggacccg ggtaccagga tccgaattct | 480 |
| ggcggtggtg gcagcgatgc agcgtggcat ctgggagaac tggtgtgggc aacctattat | 540 |
| gatccggaaa ccggcacctg gctgcctgat tgggatgtga tggtgcggca g | 591 |

<210> SEQ ID NO 133
<211> LENGTH: 591
<212> TYPE: DNA
<213> ORGANISM: Artificial Sequence
<220> FEATURE:
<223> OTHER INFORMATION: Oligo DNA

<400> SEQUENCE: 133

| | |
|---|---|
| atgagcgata aaattattca cctgactgac gacagttttg acacggatgt actcaaagcg | 60 |
| gacggggcga tcctcgtcga tttctgggca gagtggtgcg gtccgtgcaa aatgatcgcc | 120 |
| ccgattctgg atgaaatcgc tgacgaatat cagggcaaac tgaccgttgc aaaactgaac | 180 |

```
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagcgatgc agcgtggcat ctgggagaac tggtgtgggc aacctattat    540
gatccggaaa ccggcacctg ggtgcctgat gggagcgga tgaagcagca t              591
```

```
<210> SEQ ID NO 134
<211> LENGTH: 648
<212> TYPE: DNA
<213> ORGANISM: Artificial Sequence
<220> FEATURE:
<223> OTHER INFORMATION: Oligo DNA

<400> SEQUENCE: 134
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagcgggag ggcgtttagt gggagtcgta ggtggtatga tccggaaacc    540
ggcacctggt atgatgcagc gtggcatctg ggcgaactgg tgtgggcaac ctattatgat    600
ccggaaaccg gcacctgggc tcctgattgg cggcttatgc agggtcag                  648
```

```
<210> SEQ ID NO 135
<211> LENGTH: 648
<212> TYPE: DNA
<213> ORGANISM: Artificial Sequence
<220> FEATURE:
<223> OTHER INFORMATION: Oligo DNA

<400> SEQUENCE: 135
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagcgtgat ggctactgag gttgttcggg gtgtttacga ccccgagacg    540
ggcacgtggt acgatgcaac gtggcatctg ggagaactgg tgtgggcaac ctattatgat    600
ccggaaaccg ggacctggga gcctgattgg cagaggatgc tggggcag                  648
```

<210> SEQ ID NO 136
<211> LENGTH: 648
<212> TYPE: DNA
<213> ORGANISM: Artificial Sequence
<220> FEATURE:
<223> OTHER INFORMATION: Oligo DNA

<400> SEQUENCE: 136

```
atgagcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccggt tctggttctg gccatactag tggtggtggc     360
ggttctaata acaatcctcc tactcctact ccatctagtg gttctggtca tcaccatcac     420
catcactccg cggctcttga agtcctcttt cagggacccg ggtaccagga tccgaattct     480
ggcggtggtg gcagcgttat ttctttgggt tcggatcgtg gtgtttacga ccccgagacg     540
ggcacgtggt acgatgcagc gtggcatctg ggagaactgg tgtgggcaac ctattatgat     600
ccggaaaccg ggacctggga gcctgattgg cagaggatgc tggggcag                  648
```

<210> SEQ ID NO 137
<211> LENGTH: 648
<212> TYPE: DNA
<213> ORGANISM: Artificial Sequence
<220> FEATURE:
<223> OTHER INFORMATION: Oligo DNA

<400> SEQUENCE: 137

```
atgagcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccggt tctggttctg gccatactag tggtggtggc     360
ggttctaata acaatcctcc tactcctact ccatctagtg gttctggtca tcaccatcac     420
catcactccg cggctcttga agtcctcttt cagggacccg ggtaccagga tccgaattct     480
ggcggtggtg gcagcattat gtctgttgat ggtagttctg cgcgttacga ccccgagacg     540
ggcacgtggt acgatgcagc gtggcatctg ggagaactgg tgtgggcaac ctattatgat     600
ccggaaaccg ggacctggga gcctgattgg cagaggatgc tggggcag                  648
```

<210> SEQ ID NO 138
<211> LENGTH: 648
<212> TYPE: DNA
<213> ORGANISM: Artificial Sequence
<220> FEATURE:
<223> OTHER INFORMATION: Oligo DNA

<400> SEQUENCE: 138

```
atgagcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
```

```
atcgatcaaa accctggcac tgcgccgaaa tatggcatcc gtggtatccc gactctgctg      240
ctgttcaaaa acggtgaagt ggcggcaacc aaagtgggtg cactgtctaa aggtcagttg      300
aaagagttcc tcgacgctaa cctggccggt tctggttctg gccatactag tggtggtggc      360
ggttctaata acaatcctcc tactcctact ccatctagtg gttctggtca tcaccatcac      420
catcactccg cggctcttga agtcctcttt cagggacccg ggtaccagga tccgaattct      480
ggcggtggtg gcagcatgat ggttaggccg cctaggcttg gtgtttacga ccccgagccg      540
ggcacgtggt acgatgcaac gtggcatctg ggagaactgg tgtgggcaac ctattatgat      600
ccggaaaccg ggacctggga gcctgattgg cagaggatgc tggggcag                  648

<210> SEQ ID NO 139
<211> LENGTH: 648
<212> TYPE: DNA
<213> ORGANISM: Artificial Sequence
<220> FEATURE:
<223> OTHER INFORMATION: Oligo DNA

<400> SEQUENCE: 139
atgagcgata aaattattca cctgactgac gacagttttg acacggatgt actcaaagcg       60
gacggggcga tcctcgtcga tttctgggca gagtggtgcg gtccgtgcaa aatgatcgcc      120
ccgattctgg atgaaatcgc tgacgaatat caggcaaaac tgaccgttgc aaaactgaac      180
atcgatcaaa accctggcac tgcgccgaaa tatggcatcc gtggtatccc gactctgctg      240
ctgttcaaaa acggtgaagt ggcggcaacc aaagtgggtg cactgtctaa aggtcagttg      300
aaagagttcc tcgacgctaa cctggccggt tctggttctg gccatactag tggtggtggc      360
ggttctaata acaatcctcc tactcctact ccatctagtg gttctggtca tcaccatcac      420
catcactccg cggctcttga agtcctcttt cagggacccg ggtaccagga tccgaattct      480
ggcggtggtg gcagcgttga tttgcgtgct catggtgggg cggtgtacga ccccgagacg      540
ggcacgtggt acgatgcagc gtggcatctg ggagaactgg tgtgggcaac ctattatgat      600
ccggaaaccg ggacctggga gcctgattgg cagaggatgc tggggcag                  648

<210> SEQ ID NO 140
<211> LENGTH: 648
<212> TYPE: DNA
<213> ORGANISM: Artificial Sequence
<220> FEATURE:
<223> OTHER INFORMATION: Oligo DNA

<400> SEQUENCE: 140
atgagcgata aaattattca cctgactgac gacagttttg acacggatgt actcaaagcg       60
gacggggcga tcctcgtcga tttctgggca gagtggtgcg gtccgtgcaa aatgatcgcc      120
ccgattctgg atgaaatcgc tgacgaatat caggcaaaac tgaccgttgc aaaactgaac      180
atcgatcaaa accctggcac tgcgccgaaa tatggcatcc gtggtatccc gactctgctg      240
ctgttcaaaa acggtgaagt ggcggcaacc aaagtgggtg cactgtctaa aggtcagttg      300
aaagagttcc tcgacgctaa cctggccggt tctggttctg gccatactag tggtggtggc      360
ggttctaata acaatcctcc tactcctact ccatctagtg gttctggtca tcaccatcac      420
catcactccg cggctcttga agtcctcttt cagggacccg ggtaccagga tccgaattct      480
ggcggtggtg gcagctggag taggtttagt agtcggtcgg ttgcttacga ccccgagacg      540
ggcacgtggt acgatgcagc gtggcatctg ggagaactgg tgtgggcaac ctattatgat      600
```

```
ccggaaaccg ggacctggga gcctgattgg cagaggatgc tggggcag          648
```

<210> SEQ ID NO 141
<211> LENGTH: 648
<212> TYPE: DNA
<213> ORGANISM: Artificial Sequence
<220> FEATURE:
<223> OTHER INFORMATION: Oligo DNA

<400> SEQUENCE: 141

```
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagcgagcg tcatcttgtt tcggattatt tgcattacga ccccgagacg    540
ggcacgtggt acgatgcagc gtggcatctg ggagaactgg tgtgggcaac ctattatgat    600
ccggaaaccg ggacctggga gcctgattgg cagaggatgc tggggcag              648
```

<210> SEQ ID NO 142
<211> LENGTH: 648
<212> TYPE: DNA
<213> ORGANISM: Artificial Sequence
<220> FEATURE:
<223> OTHER INFORMATION: Oligo DNA

<400> SEQUENCE: 142

```
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagcttttc ggatttggat agttttggtg tttcttacga ccccgagacg    540
ggcacgtggt acgatgcagc gtggcatcgg ggagaactgg tgtgggcaac ctattatgat    600
ccggaaaccg ggacctggga gcctgattgg cagaggatgc tggggcag              648
```

<210> SEQ ID NO 143
<211> LENGTH: 648
<212> TYPE: DNA
<213> ORGANISM: Artificial Sequence
<220> FEATURE:
<223> OTHER INFORMATION: Oligo DNA

<400> SEQUENCE: 143

```
atgagcgata aaattattca cctgactgac gacagttttg acacggatgt actcaaagcg     60
gacggggcga tcctcgtcga tttctgggca gagtggtgcg gtccgtgcaa aatgatcgcc    120
```

```
ccgattctgg atgaaatcgc tgacgaatat cagggcaaac tgaccgttgc aaaactgaac      180
atcgatcaaa accctggcac tgcgccgaaa tatggcatcc gtggtatccc gactctgctg      240
ctgttcaaaa acggtgaagt ggcggcaacc aaagtgggtg cactgtctaa aggtcagttg      300
aaagagttcc tcgacgctaa cctggccggt tctggttctg gccatactag tggtggtggc      360
ggttctaata acaatcctcc tactcctact ccatctagtg gttctggtca tcaccatcac      420
catcactccg cggctcttga agtcctcttt cagggacccg gtaccagga tccgaattct      480 ggcggtggtg gcagccttttt tgataataag ttgaagcatg cttcttacga ccccgagacg      540
ggcacgtggt acgatgcagc gtggcatctg ggagaactgg tgtgggcaac ctattatgat      600
ccggaaaccg ggacctggga gcctgattgg cagaggatgc tggggcag                  648
```

<210> SEQ ID NO 144
<211> LENGTH: 648
<212> TYPE: DNA
<213> ORGANISM: Artificial Sequence
<220> FEATURE:
<223> OTHER INFORMATION: Oligo DNA

<400> SEQUENCE: 144

```
atgagcgata aaattattca cctgactgac gacagttttg acacggatgt actcaaagcg       60
gacggggcga tcctcgtcga tttctgggca gagtggtgcg gtccgtgcaa aatgatcgcc      120
ccgattctgg atgaaatcgc tgacgaatat cagggcaaac tgaccgttgc aaaactgaac      180
atcgatcaaa accctggcac tgcgccgaaa tatggcatcc gtggtatccc gactctgctg      240
ctgttcaaaa acggtgaagt ggcggcaacc aaagtgggtg cactgtctaa aggtcagttg      300
aaagagttcc tcgacgctaa cctggccggt tctggttctg gccatactag tggtggtggc      360
ggttctaata acaatcctcc tactcctact ccatctagtg gttctggtca tcaccatcac      420
catcactccg cggctcttga agtcctcttt cagggacccg gtaccagga tccgaattct      480 ggcggtggtg gcagcggtaa tccgtctgat tcggctagtc gtggtacga ccccgagacg      540 ggcacgtggt acgatgcagc gtggcatctg ggagaactgg tgtgggcaac ctattatgat      600
ccggaaaccg ggacctggga gcctgattgg cagaggatgc tggggcag                  648
```

<210> SEQ ID NO 145
<211> LENGTH: 648
<212> TYPE: DNA
<213> ORGANISM: Artificial Sequence
<220> FEATURE:
<223> OTHER INFORMATION: Oligo DNA

<400> SEQUENCE: 145

```
atgagcgata aaattattca cctgactgac gacagttttg acacggatgt actcaaagcg       60
gacggggcga tcctcgtcga tttctgggca gagtggtgcg gtccgtgcaa aatgatcgcc      120
ccgattctgg atgaaatcgc tgacgaatat cagggcaaac tgaccgttgc aaaactgaac      180
atcgatcaaa accctggcac tgcgccgaaa tatggcatcc gtggtatccc gactctgctg      240
ctgttcaaaa acggtgaagt ggcggcaacc aaagtgggtg cactgtctaa aggtcagttg      300
aaagagttcc tcgacgctaa cctggccggt tctggttctg gccatactag tggtggtggc      360
ggttctaata acaatcctcc tactcctact ccatctagtg gttctggtca tcaccatcac      420
catcactccg cggctcttga agtcctcttt cagggacccg gtaccagga tccgaattct      480 ggcggtggtg gcagctctaa ttttgtgcgt agtccttcgg cttggtacga ccccgagacg      540
```

<210> SEQ ID NO 146
<211> LENGTH: 648
<212> TYPE: DNA
<213> ORGANISM: Artificial Sequence
<220> FEATURE:
<223> OTHER INFORMATION: Oligo DNA

<400> SEQUENCE: 146

```
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg gtaccagga tccgaattct    480
ggcggtggtg gcagcattcc ttatgggttt ccggggcgtg gtgagtacga ccccgagacg    540
ggcacgtggt acgatgcagc gtggcatctg ggagaactgg tgtgggcaac ctattatgat    600
ccggaaaccg ggacctggga gcctgattgg cagaggatgc tggggcag                 648
```

<210> SEQ ID NO 147
<211> LENGTH: 648
<212> TYPE: DNA
<213> ORGANISM: Artificial Sequence
<220> FEATURE:
<223> OTHER INFORMATION: Oligo DNA

<400> SEQUENCE: 147

```
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg gtaccagga tccgaattct    480
ggcggtggtg gcagcggtcc ttataatatt cctgattcgg cggtttacga ccccgagacg    540
ggcacgtggt acgatgcagc gtggcatctg ggagaactgg tgtgggcaac ctattatgat    600
ccggaaaccg ggacctggga gcctgattgg cagaggatgc tggggcag                 648
```

<210> SEQ ID NO 148
<211> LENGTH: 648
<212> TYPE: DNA
<213> ORGANISM: Artificial Sequence
<220> FEATURE:
<223> OTHER INFORMATION: Oligo DNA

<400> SEQUENCE: 148

```
atgagcgata aaattattca cctgactgac gacagttttg acacggatgt actcaaagcg     60
```

```
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata caatcctcc  tactcctact ccatctagtg gttctggtca tcaccatcac    420
catcactccg cggctcttga agtcctcttt cagggacccg ggtaccagga tccgaattct    480
ggcggtggtg gcagctggcc gttgaatgct ccgtcttctg cttttacga ccccgagacg     540 ggcacgtggt acgatgcagc gtggcatctg ggagaactgg tgtgggcaac ctattatgat    600
ccggaaaccg ggacctggga gcctgattgg cagaggatgc tggggcag               648
```

<210> SEQ ID NO 149
<211> LENGTH: 648
<212> TYPE: DNA
<213> ORGANISM: Artificial Sequence
<220> FEATURE:
<223> OTHER INFORMATION: Oligo DNA

<400> SEQUENCE: 149

```
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata caatcctcc  tactcctact ccatctagtg gttctggtca tcaccatcac    420
catcactccg cggctcttga agtcctcttt cagggacccg ggtaccagga tccgaattct    480
ggcggtggtg gcagcgttcc tcctcgtttt tcttcttctg ctcagtacga ccccgagacg    540
ggcacgtggt acgatgcagc gtggcatctg ggagaactgg tgtgggcaac ctattatgat    600
ccggaaaccg ggacctggga gcctgattgg cagaggatgc tggggcag                648
```

<210> SEQ ID NO 150
<211> LENGTH: 648
<212> TYPE: DNA
<213> ORGANISM: Artificial Sequence
<220> FEATURE:
<223> OTHER INFORMATION: Oligo DNA

<400> SEQUENCE: 150

```
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata caatcctcc  tactcctact ccatctagtg gttctggtca tcaccatcac    420
catcactccg cggctcttga agtcctcttt cagggacccg ggtaccagga tccgaattct    480
```

```
ggcggtggtg gcagctttct ggtttgggctt catgctggtg cggtttacga ccccgagacg    540
ggcacgtggt acgatgcagc gtggcatctg ggagaactgg tgtgggcaac ctattatgat    600
ccggaaaccg ggacctggga gcctgattgg cagaggatgc tggggcag                 648
```

<210> SEQ ID NO 151
<211> LENGTH: 648
<212> TYPE: DNA
<213> ORGANISM: Artificial Sequence
<220> FEATURE:
<223> OTHER INFORMATION: Oligo DNA

<400> SEQUENCE: 151

```
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagcgttgt gagggttgat catagttctg ctgtttacga ccccgagacg    540
ggcacgtggt acgatgcagc gtggcatctg ggagaactgg tgtgggcaac ctattatgat    600
ccggaaaccg ggacctggga gcctgattgg cagaggatgc tggggcag                 648
```

<210> SEQ ID NO 152
<211> LENGTH: 648
<212> TYPE: DNA
<213> ORGANISM: Artificial Sequence
<220> FEATURE:
<223> OTHER INFORMATION: Oligo DNA

<400> SEQUENCE: 152

```
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagcggttc ttgtaagttt tcttctagtt gtcattacga ccccgagacg    540
ggcacgtggt acgatgcagc gtggcatctg ggagaactgg tgtgggcaac ctattatgat    600
ccggaaaccg ggacctggga gcctgattgg cagaggatgc tggggcag                 648
```

<210> SEQ ID NO 153
<211> LENGTH: 648
<212> TYPE: DNA
<213> ORGANISM: Artificial Sequence
<220> FEATURE:
<223> OTHER INFORMATION: Oligo DNA

<400> SEQUENCE: 153

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gtaccagga tccgaattct   480 ggcggtggtg gcagccttat tcctcctggg ggtattagtc cttggtacga ccccgagacg   540
ggcacgtggt acgatgcagc gtggcatctg ggagaactgg tgtgggcaac ctattatgat   600
ccggaaaccg ggacctggga gcctgattgg cagaggatgc tggggcag                648
```

<210> SEQ ID NO 154
<211> LENGTH: 648
<212> TYPE: DNA
<213> ORGANISM: Artificial Sequence
<220> FEATURE:
<223> OTHER INFORMATION: Oligo DNA

<400> SEQUENCE: 154

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gtaccagga tccgaattct   480 ggcggtggtg gcagctggat ggagttttat cctgggcgtg gtgtttacga ccccgagacg   540
ggcacgtggt acgatgcagc gtggcatctg ggagaactgg tgtgggcaac ctattatgat   600
ccggaaaccg ggacctggga gcctgattgg cagaggatgc tggggcag                648
```

<210> SEQ ID NO 155
<211> LENGTH: 648
<212> TYPE: DNA
<213> ORGANISM: Artificial Sequence
<220> FEATURE:
<223> OTHER INFORMATION: Oligo DNA

<400> SEQUENCE: 155

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
```

```
catcactccg cggctcttga agtcctcttt cagggacccg ggtaccagga tccgaattct    480
ggcggtggtg gcagcgatgg tgttggtccg ggtagtcgtg gggtttacga ccccgagacg    540
ggcacgtggt acgatgcagc gtggcatctg ggagaactgg tgtgggcaac ctattatgat    600
ccggaaaccg ggacctggga gcctgattgg cagaggatgc tggggcag                 648
```

<210> SEQ ID NO 156
<211> LENGTH: 648
<212> TYPE: DNA
<213> ORGANISM: Artificial Sequence
<220> FEATURE:
<223> OTHER INFORMATION: Oligo DNA

<400> SEQUENCE: 156

```
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagctttgt tagttctttg cctaatagtg cgatgtacga ccccgagacg    540
ggcacgtggt acgatgcagc gtggcatctg ggagaactgg tgtgggcaac ctattatgat    600
ccggaaaccg ggacctggga gcctgattgg cagaggatgc tggggcag                 648
```

<210> SEQ ID NO 157
<211> LENGTH: 648
<212> TYPE: DNA
<213> ORGANISM: Artificial Sequence
<220> FEATURE:
<223> OTHER INFORMATION: Oligo DNA

<400> SEQUENCE: 157

```
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg ggtaccagga tccgaattct    480
ggcggtggtg gcagccttaa tgattttctt actccgacgg cttggtacga ccccgagacg    540
ggcacgtggt acgatgcagc gtggcatctg ggagaactgg tgtgggcaac ctattatgat    600
ccggaaaccg ggacctggct tcctgattgg cagacgatgg cgcagaag                 648
```

<210> SEQ ID NO 158
<211> LENGTH: 25
<212> TYPE: PRT
<213> ORGANISM: Artificial Sequence
<220> FEATURE:
<223> OTHER INFORMATION: IgG binding peptide, 2A1_Q5R -continued

<400> SEQUENCE: 158

Gly Val Val Arg Arg Trp Ser Gly Tyr Asp Pro Arg Thr Gly Thr Trp
1               5                   10                  15

Arg Ser Ser Ile Ala Tyr Gly Gly Gly
            20                  25

<210> SEQ ID NO 159
<211> LENGTH: 25
<212> TYPE: PRT
<213> ORGANISM: Artificial Sequence
<220> FEATURE:
<223> OTHER INFORMATION: IgG binding peptide, 2A1_W6A

<400> SEQUENCE: 159

Gly Val Val Arg Gln Ala Ser Gly Tyr Asp Pro Arg Thr Gly Thr Trp
1               5                   10                  15

Arg Ser Ser Ile Ala Tyr Gly Gly Gly
            20                  25

<210> SEQ ID NO 160
<211> LENGTH: 25
<212> TYPE: PRT
<213> ORGANISM: Artificial Sequence
<220> FEATURE:
<223> OTHER INFORMATION: IgG binding peptide, 2A1_S7A

<400> SEQUENCE: 160

Gly Val Val Arg Gln Trp Ala Gly Tyr Asp Pro Arg Thr Gly Thr Trp
1               5                   10                  15

Arg Ser Ser Ile Ala Tyr Gly Gly Gly
            20                  25

<210> SEQ ID NO 161
<211> LENGTH: 25
<212> TYPE: PRT
<213> ORGANISM: Artificial Sequence
<220> FEATURE:
<223> OTHER INFORMATION: IgG binding peptide, 2A1_R17A

<400> SEQUENCE: 161

Gly Val Val Arg Gln Trp Ser Gly Tyr Asp Pro Arg Thr Gly Thr Trp
1               5                   10                  15

Ala Ser Ser Ile Ala Tyr Gly Gly Gly
            20                  25

<210> SEQ ID NO 162
<211> LENGTH: 25
<212> TYPE: PRT
<213> ORGANISM: Artificial Sequence
<220> FEATURE:
<223> OTHER INFORMATION: IgG binding peptide, 2A1_S18A

<400> SEQUENCE: 162

Gly Val Val Arg Gln Trp Ser Gly Tyr Asp Pro Arg Thr Gly Thr Trp
1               5                   10                  15

Arg Ala Ser Ile Ala Tyr Gly Gly Gly
            20                  25

<210> SEQ ID NO 163
<211> LENGTH: 25
<212> TYPE: PRT
<213> ORGANISM: Artificial Sequence
<220> FEATURE:

<223> OTHER INFORMATION: IgG binding peptide, 2A1_S19A

<400> SEQUENCE: 163

Gly Val Val Arg Gln Trp Ser Gly Tyr Asp Pro Arg Thr Gly Thr Trp
1               5                   10                  15

Arg Ser Ala Ile Ala Tyr Gly Gly Gly
            20                  25

<210> SEQ ID NO 164
<211> LENGTH: 25
<212> TYPE: PRT
<213> ORGANISM: Artificial Sequence
<220> FEATURE:
<223> OTHER INFORMATION: IgG binding peptide, 2A1 I20A

<400> SEQUENCE: 164

Gly Val Val Arg Gln Trp Ser Gly Tyr Asp Pro Arg Thr Gly Thr Trp
1               5                   10                  15

Arg Ser Ser Ala Ala Tyr Gly Gly Gly
            20                  25

<210> SEQ ID NO 165
<211> LENGTH: 13
<212> TYPE: PRT
<213> ORGANISM: Artificial Sequence
<220> FEATURE:
<223> OTHER INFORMATION: IgG binding peptide, Fc-III

<400> SEQUENCE: 165

Asp Cys Ala Trp His Leu Gly Glu Leu Val Trp Cys Thr
1               5                   10

<210> SEQ ID NO 166
<211> LENGTH: 16
<212> TYPE: PRT
<213> ORGANISM: Artificial Sequence
<220> FEATURE:
<223> OTHER INFORMATION: IgG binding peptide
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be any amino acid

<400> SEQUENCE: 166

Arg Thr Xaa Arg Thr Xaa Arg Thr Xaa Arg Thr Xaa Lys Lys Lys Gly
1               5                   10                  15

<210> SEQ ID NO 167
<211> LENGTH: 10
<212> TYPE: PRT
<213> ORGANISM: Artificial Sequence
<220> FEATURE:
<223> OTHER INFORMATION: IgG binding peptide
<220> FEATURE:
<221> NAME/KEY: MISC_FEATURE
<222> LOCATION: (2)..(8)
<223> OTHER INFORMATION: Xaa can be any amino acid

```
<400> SEQUENCE: 167

Cys Xaa Xaa Xaa Cys Xaa Xaa Xaa Lys Gly
1               5                   10

<210> SEQ ID NO 168
<211> LENGTH: 17
<212> TYPE: PRT
<213> ORGANISM: Artificial Sequence
<220> FEATURE:
<223> OTHER INFORMATION: IgG binding peptide library
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (9)..(16)
<223> OTHER INFORMATION: Xaa can be any amino acid

<400> SEQUENCE: 168

Tyr Asp Pro Xaa Thr Gly Thr Trp Xaa Xaa Xaa Xaa Xaa Xaa Xaa
1               5                   10                  15

Gly

<210> SEQ ID NO 169
<211> LENGTH: 5
<212> TYPE: PRT
<213> ORGANISM: Artificial Sequence
<220> FEATURE:
<223> OTHER INFORMATION: glycine linker

<400> SEQUENCE: 169

Gly Gly Gly Gly Ser
1               5

<210> SEQ ID NO 170
<211> LENGTH: 25
<212> TYPE: PRT
<213> ORGANISM: Artificial Sequence
<220> FEATURE:
<223> OTHER INFORMATION: IgG binding peptide library
<220> FEATURE:
<221> NAME/KEY: MISC_FEATURE
<222> LOCATION: (1)..(10)
<223> OTHER INFORMATION: Xaa can be any amino acid

<400> SEQUENCE: 170

Xaa Xaa Xaa Xaa Xaa Xaa Xaa Xaa Tyr Asp Pro Arg Thr Gly Thr Trp
1               5                   10                  15

Arg Ser Ser Ile Ala Tyr Gly Gly Gly
            20                  25

<210> SEQ ID NO 171
<211> LENGTH: 32
<212> TYPE: PRT
<213> ORGANISM: Artificial Sequence
<220> FEATURE:
<223> OTHER INFORMATION: IgG binding peptide library
<220> FEATURE:
<221> NAME/KEY: MISC_FEATURE
<222> LOCATION: (23)..(32)
<223> OTHER INFORMATION: Xaa can be any amino acid

<400> SEQUENCE: 171

Asp Ala Ala Trp His Leu Gly Glu Leu Val Trp Ala Thr Tyr Tyr Asp
1               5                   10                  15
```

Pro Glu Thr Gly Thr Trp Xaa Xaa Xaa Xaa Xaa Xaa Xaa Xaa
            20                  25                  30

<210> SEQ ID NO 172
<211> LENGTH: 51
<212> TYPE: PRT
<213> ORGANISM: Artificial Sequence
<220> FEATURE:
<223> OTHER INFORMATION: IgG binding peptide library
<220> FEATURE:
<221> NAME/KEY: MISC_FEATURE
<222> LOCATION: (1)..(10)
<223> OTHER INFORMATION: Xaa can be any amino acid

<400> SEQUENCE: 172

Xaa Xaa Xaa Xaa Xaa Xaa Xaa Xaa Xaa Xaa Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Leu Pro Asp Trp Gln Thr Met
        35                  40                  45

Ala Gln Lys
    50

<210> SEQ ID NO 173
<211> LENGTH: 51
<212> TYPE: PRT
<213> ORGANISM: Artificial Sequence
<220> FEATURE:
<223> OTHER INFORMATION: IgG binding peptide library
<220> FEATURE:
<221> NAME/KEY: MISC_FEATURE
<222> LOCATION: (1)..(10)
<223> OTHER INFORMATION: Xaa can be any amino acid

<400> SEQUENCE: 173

Xaa Xaa Xaa Xaa Xaa Xaa Xaa Xaa Xaa Xaa Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 174
<211> LENGTH: 54
<212> TYPE: PRT
<213> ORGANISM: Artificial Sequence
<220> FEATURE:
<223> OTHER INFORMATION: IgG binding peptide, p17_P46A

<400> SEQUENCE: 174

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30

Trp Ala Thr Tyr Tyr Asp Pro Glu Thr Gly Thr Trp Glu Ala Asp Trp
        35                  40                  45

Gln Arg Met Leu Gly Gln
    50

<210> SEQ ID NO 175

```
<211> LENGTH: 54
<212> TYPE: PRT
<213> ORGANISM: Artificial Sequence
<220> FEATURE:
<223> OTHER INFORMATION: IgG binding peptide, p17_D47A

<400> SEQUENCE: 175

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30

Trp Ala Thr Tyr Tyr Asp Pro Glu Thr Gly Thr Trp Glu Pro Ala Trp
        35                  40                  45

Gln Arg Met Leu Gly Gln
    50

<210> SEQ ID NO 176
<211> LENGTH: 54
<212> TYPE: PRT
<213> ORGANISM: Artificial Sequence
<220> FEATURE:
<223> OTHER INFORMATION: IgG binding peptide, p17_W48A

<400> SEQUENCE: 176

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30

Trp Ala Thr Tyr Tyr Asp Pro Glu Thr Gly Thr Trp Glu Pro Asp Ala
        35                  40                  45

Gln Arg Met Leu Gly Gln
    50

<210> SEQ ID NO 177
<211> LENGTH: 54
<212> TYPE: PRT
<213> ORGANISM: Artificial Sequence
<220> FEATURE:
<223> OTHER INFORMATION: IgG binding peptide, p17_R50A

<400> SEQUENCE: 177

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30

Trp Ala Thr Tyr Tyr Asp Pro Glu Thr Gly Thr Trp Glu Pro Asp Trp
        35                  40                  45

Gln Ala Met Leu Gly Gln
    50

<210> SEQ ID NO 178
<211> LENGTH: 54
<212> TYPE: PRT
<213> ORGANISM: Artificial Sequence
<220> FEATURE:
<223> OTHER INFORMATION: IgG binding peptide, p17_M51A

<400> SEQUENCE: 178

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30
```

Trp Ala Thr Tyr Tyr Asp Pro Glu Thr Gly Thr Trp Glu Pro Asp Trp
        35                  40                  45

Gln Arg Ala Leu Gly Gln
    50

<210> SEQ ID NO 179
<211> LENGTH: 618
<212> TYPE: DNA
<213> ORGANISM: Artificial Sequence
<220> FEATURE:
<223> OTHER INFORMATION: oligo DNA

<400> SEQUENCE: 179

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gcattagtgc gttttctccg   480
gggcgtgggg tgtacgaccc cgagacgggc acgtggtacg atgcagcgtg gcatctggga   540
gaactggtgt gggcaaccta ttatgatccg gaaaccggga cctgggaggc tgattggcag   600
aggatgctgg ggcagtag                                                 618
```

<210> SEQ ID NO 180
<211> LENGTH: 618
<212> TYPE: DNA
<213> ORGANISM: Artificial Sequence
<220> FEATURE:
<223> OTHER INFORMATION: oligo DNA

<400> SEQUENCE: 180

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gcattagtgc gttttctccg   480
gggcgtgggg tgtacgaccc cgagacgggc acgtggtacg atgcagcgtg gcatctggga   540
gaactggtgt gggcaaccta ttatgatccg gaaaccggga cctgggagcc tgcttggcag   600
aggatgctgg ggcagtag                                                 618
```

<210> SEQ ID NO 181
<211> LENGTH: 618
<212> TYPE: DNA
<213> ORGANISM: Artificial Sequence
<220> FEATURE:
<223> OTHER INFORMATION: oligo DNA

<400> SEQUENCE: 181

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gcattagtgc gttttctccg   480
gggcgtgggg tgtacgaccc cgagacgggc acgtggtacg atgcagcgtg gcatctggga   540
gaactggtgt gggcaaccta ttatgatccg gaaaccggga cctgggagcc tgatgcgcag   600
aggatgctgg ggcagtag                                                618
```

<210> SEQ ID NO 182
<211> LENGTH: 618
<212> TYPE: DNA
<213> ORGANISM: Artificial Sequence
<220> FEATURE:
<223> OTHER INFORMATION: oligo DNA

<400> SEQUENCE: 182

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gcattagtgc gttttctccg   480
gggcgtgggg tgtacgaccc cgagacgggc acgtggtacg atgcagcgtg gcatctggga   540
gaactggtgt gggcaaccta ttatgatccg gaaaccggga cctgggagcc tgattggcag   600
gcgatgctgg ggcagtag                                                618
```

<210> SEQ ID NO 183
<211> LENGTH: 618
<212> TYPE: DNA
<213> ORGANISM: Artificial Sequence
<220> FEATURE:
<223> OTHER INFORMATION: oligo DNA

<400> SEQUENCE: 183

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
```

```
catcactccg cggctcttga agtcctcttt cagggacccg gcattagtgc gttttctccg    480
gggcgtgggg tgtacgaccc cgagacgggc acgtggtacg atgcagcgtg gcatctggga    540
gaactggtgt gggcaaccta ttatgatccg gaaaccggga cctgggagcc tgattggcag    600
agggcgctgg ggcagtag                                                  618
```

ANTIBODY-BINDING PEPTIDE

CROSS REFERENCE TO RELATED APPLICATIONS

This application is a National Stage of International Application No. PCT/JP2013/007583 filed Dec. 25, 2013, claiming priority based on Japanese Patent Application No. 2013-013217 filed Jan. 28, 2013, the contents of all of which are incorporated herein by reference in their entirety.

TECHNICAL FIELD

The present invention relates to a peptide exhibiting binding activity to an Fc region of immunoglobulin G, and a method for detecting, purifying, immobilizing or removing an antibody, immunoglobulin G or a protein containing an Fc region of immunoglobulin G by using the peptide.

BACKGROUND ART

So-called antibody drugs using monoclonal antibodies for therapy have annual sales of beyond $30 billion and belong to the largest segment in the biotechnology-based pharmaceutical products as well as the most rapidly growing segment in the entire pharmaceutical industry. Up to the present, 23 types of full-size monoclonal antibodies and three types of monoclonal antibody fragments have been launched. Some of them have already become blockbusters having annual sales of beyond $1 billion. The number of monoclonal antibodies as drug candidates whose clinical trials have been initiated during the period from 1995 to 2007 has increased three times or more and still further increased (Non Patent Literature 1).

With a growth and development of such an antibody drug market, research and development have been accelerated with a view to designing and improving a molecule having a binding property to an antibody, immunoglobulin G or a protein containing an Fc region of immunoglobulin G (hereinafter, also referred to as antibodies and others). This is because such a molecule is useful for research and production of antibodies and others, in particular, expected to have a great demand in affinity chromatography used in a recovery/purification step of a process for producing antibody drugs. This is also because protein A, which is derived from *Staphylococcus* and frequently used presently for recovering and purifying antibodies and others, is recognized as being insufficient in view of stability and production cost. At present, various research and development approaches are made for obtaining molecules capable of binding to antibodies and others (Non Patent Literature 2). One of them is development of antibody-binding peptides. Some of examples are as follows.

Suzuki et al., identified a plurality of polypeptides exhibiting binding activity to an Fc region of human IgG by using a phage library displaying 7-residue or 12-residue linear peptides on filamentous bacteriophage M13 and the presence or absence of a binding property to Fc region of human IgG was determined by Enzyme Linked Immuno-Sorbent Assay (ELISA) (Patent Literature 1). They extracted a common sequence from the sequences identified and a peptide was prepared from the common sequence. The binding activity of the peptide not only to human IgG but also to an Fc region of IgG derived from a horse, sheep, rabbit, guinea pig, goat, cat, dog, cow, pig and mouse, was checked by ELISA.

DeLano et al., obtained a plurality of 20-residue cyclic peptides, which bind to human IgG competitively with protein A derived from yellow *Staphylococcus*, by using a phage library displaying a cyclic peptide, which is cyclized via a disulfide bond and represented by $Xaa_i$ Cys $Xaa_j$ Cys $Xaa_k$ (where i, j and k are integers satisfying the expression: i+j+k=18), on filamentous bacteriophage M13. They further extracted a common sequence from these peptides and cyclic peptide Fc-III of 13 residues (Asp Cys Ala Trp His Leu Gly Glu Leu Val Trp Cys Thr) (SEQ ID NO: 165) was prepared. They found that cyclic peptide Fc-III shows a competitive inhibitory capacity of $K_i$=100 nM in the competitive reaction with protein A. They disclosed that the in-vivo Fab half-life period can be improved by combining a Fab fragment (which is an antigen binding site of IgG) with Fc-III to make a fusion protein, in an experiment using rabbits (Patent Literature 2 and Non Patent Literature 3). Dias et al., further prepared FcBP-2 by further introducing cyclization into cyclic peptide Fc-III by use of D-form and L-form Pro residue and succeeded in enhancing its binding property (Fc-III equilibrium dissociation constant, $K_D$=185 nM) to IgG up to $K_D$=2 nM (Non Patent Literature 4).

Fassina et al., screened a library of a synthesized tetrapolypeptide represented by (Arg Thr Xaa)$_4$ Lys$_2$ Lys Gly (SEQ ID NO: 166) having a branched structure ascribed to a Lys residue and prepared peptide TG19318, which competitively works with protein A (Non Patent Literature 5). They showed that TG19318 has a binding property of $K_D$=300 nM to rabbit IgG, and further that IgG contained in the sera of human, bovine, horse, pig, mouse, rat, goat and sheep can be purified by affinity chromatography prepared by immobilizing TG19318 (Non Patent Literature 6).

Ehrlich et al., isolated a peptide exhibiting a binding property to a pFc' fragment, which is obtained by digesting humanized IgG with pepsin, by using a phage library displaying 7-residue or 12-residue linear peptide on filamentous bacteriophage M13, in the same manner as in Suzuki et al. (Non Patent Literature 7).

Krook et al., prepared a peptide exhibiting a binding property to an Fc region of human IgG by using a phage library displaying 10 residue-long linear peptides on filamentous bacteriophage M13. They confirmed by ELISA that this peptide exhibits a strong binding property to IgG molecules derived from human and pig (Non Patent Literature 8).

Verdoliva et al., screened a library of a synthetic peptide represented by (Cys Xaa$_3$)$_2$ Lys Gly (SEQ ID NO: 167), into which a branched structure ascribed to a Lys residue and cyclization ascribed to a Cys residue are introduced, for a mouse monoclonal IgG, and prepared peptide FcRM exhibiting a binding property to a site near a hinge region. They further constructed affinity chromatography using immobilized FcRM, and reported on purification of IgG molecules derived from a mouse and a human (Non Patent Literature 9).

Sakamoto et al., prepared a peptide exhibiting a binding property to an Fc region of human IgG by using a phage library displaying a cyclic peptide represented by Cys Xaa$_{7-10}$ Cys on T7 bacteriophage (Non Patent Literature 10). The peptide they prepared is different from the aforementioned IgG-binding peptides so far prepared since the peptide recognizes not a natural structure of an Fc region but a non-native structure of the Fc region produced by an acid treatment. Ito et al., disclosed that if this peptide is used, the content of a non-native structure produced by an acid treatment and contained in human antibody drugs, immunoglobulin preparations and IgG reagents can be checked (Patent Literature 3).

As described in the above, a plurality of antibody-binding peptides have been developed; however, molecular diversity of them may not be sufficient. This is because antibodies are used in a wide variety of needs in various industrial fields besides the aforementioned therapeutic applications, and molecular properties required for an antibody-binding molecule are not the same. In detecting, purifying, immobilizing or removing antibodies and others, antibody-binding molecules having properties suitable for individual situations must be used. To describe more specifically, antibody-binding molecules having appropriate properties are required in consideration of the sites of the antibodies and others to which an antibody-binding molecule binds, the specificity of an antibody-binding molecule to the binding site, the binding affinity of an antibody-binding molecule, association/dissociation control by changing conditions of e.g., a solution, whether or not an antibody-binding molecule binds to antibodies of a plurality of animal species or a specific animal species alone, properties such as solubility and stability and possibility of a large-scale production. In the case of a peptide, for example, whether a peptide contains a non-native amino acid residue or is constituted only of natural amino acid residues, whether a peptide has a linear, cyclic or branched chemical structure, whether a peptide forms a stable three-dimensional structure in a solution and whether a peptide can be used under a reductive environment are the items to be considered when adaptability of the peptide is determined.

Usually, the function of a short-chain polypeptide is enhanced by stabilization through cyclization via e.g., an intramolecular disulfide crosslinkage; however, a complicated chemical reaction is required for cyclization. In addition, a short-chain polypeptide does not exhibit a binding function, for example, under a reductive condition where a disulfide crosslinkage is not easily formed. As the reductive condition where a disulfide crosslinkage is not easily formed, for example, (1) cytoplasmic environment and (2) environment where a reducing agent is added in order to convert the thiol group of a cysteine residue of a target IgG or an Fc region to a free radical for e.g., chemical modification, are conceived.

With the growth of the antibody drug market, it has recently been strongly desired to further improve separation/purification techniques and analysis techniques of antibody molecules.

As to the analysis techniques, it has been desired to develop the following three techniques: (1) analysis technique for heterogeneity of a molecule caused by post-translational modification including sugar chain addition; (2) analysis technique for heterogeneity of an antibody molecule caused by conformational change; and (3) analysis technique for heterogeneity of a molecule caused by formation of associates or aggregates (Non Patent Literature 11). It has been reported that when an antibody molecule receives various physical or chemical stresses, a non-native structure (different from a general natural structure) called an alternatively folded state (AFS) is formed. It is suggested that such a non-native structure not only reduces the effect of a drug but also induces immunogenicity, causing a risk of a side effect. For the reason, an analysis technique for finding an antibody having a non-native structure is desired (Non Patent Literature 12).

Examples of a technique for analyzing the shape or conformation of a protein molecule include X-ray crystal structural analysis, nuclear magnetic resonance, electron microscopic analysis, analytical ultracentrifugation, isoelectric point electrophoresis, dynamic light scattering, circular dichroism spectroscopy and liquid chromatography; these methods all fail to satisfy both atomic-level accuracy and throughput. To describe more specifically, for example, the X-ray crystal structural analysis and nuclear magnetic resonance can provide conformational data with an atomic-level accuracy; however, several months are required for analysis. In contrast, in the dynamic light scattering and liquid chromatography, measurement is completed in several minutes; however, a small molecular change and slight contamination cannot be detected. In the circumstances, it has been desired to develop a simple technique satisfying not only an atomic-level accuracy but also throughput.

In the meantime, as the separation/purification technique, an affinity chromatography technique using a molecule having a specific affinity for an antibody as a ligand is presently indispensable (Non Patent Literature 13). At present, the ligand for use in affinity chromatography, a bacteria-derived natural protein such as protein A and protein G are used. These proteins have satisfactory affinity for antibodies; however, low stability and high production cost are drawbacks of them.

CITATION LIST

Patent Literature

Patent Literature 1: Japanese Patent Laid-Open No. 2004-187563
Patent Literature 2: International Publication No. WO/2001/045746
Patent Literature 3: International Publication No. WO/2008/054030

Non Patent Literature

Non Patent Literature 1: "Preclinical Development of Monoclonal Antibodies and Related Biologicals: Emerging technologies and new therapeutic candidates", pp. 16-20. Business Insights Ltd. (2010)
Non Patent Literature 2: Shinya Honda, "Purification Process of Antibody Drug—Protein A Affinity Chromatography,"<CMC study/application and acquisition of equivalency in bio/antibody drug/generic drug>, p. 149-172, Science & Technology (2011)
Non Patent Literature 3: DeLano W L, Ultsch M H, de Vos A M and Wells J A. (2000) Convergent solutions to binding at a protein-protein interface. Science 287(5456) 1279-1283
Non Patent Literature 4: Dias R L, Fasan R, Moehle K, Renard A, Obrecht D and Robinson J A. (2006) Protein ligand design: from phage display to synthetic protein epitope mimetics in human antibody Fc-binding peptidomimetics. J Am Chem Soc. 128(8) 2726-2732
Non Patent Literature 5: Fassina G, Verdoliva A, Odierna M R, Ruvo M and Cassini G. (1996) Protein A mimetic peptide ligand for affinity purification of antibodies. J Mol. Recognit. 9(5-6) 564-569
Non Patent Literature 6: Fassina G, Verdoliva A, Palombo G, Ruvo M and Cassani G. (1998) Immunoglobulin specificity of TG19318: a novel synthetic ligand for antibody affinity purification. J Mol Recognit. 11(1-6) 128-133
Non Patent Literature 7: Ehrlich G K and Bailon P. (1998) Identification of peptides that bind to the constant region of a humanized IgG1 monoclonal antibody using phage display. J Mol Recognit. 11(1-6) 121-125
Non Patent Literature 8: Krook M, Mosbach K, Ramstrom O. (1998) Novel peptides binding to the Fc-portion of immunoglobulins obtained from a combinatorial phage display peptide library. J Immunol Methods. 221(1-2) 151-157
Non Patent Literature 9: Verdoliva A, Marasco D, De Capua A, Saporito A, Bellofiore P, Manfredi V, Fattorusso R, Pedone C and Ruvo M. (2005) A new ligand for immunoglobulin g subdomains by screening of a synthetic peptide library. Chembiochem. 6(7) 1242-1253
Non Patent Literature 10: Sakamoto K, Ito Y, Hatanaka T, Soni P B, Mori T and Sugimura K. (2009) Discovery and characterization of a peptide motif that specifically recognizes a non-native conformation of human IgG induced by acidic pH conditions. J Biol Chem. 284(15) 9986-9993
Non Patent Literature 11: Berkowitz S A, Engen J R, Mazzeo J R, Jones G B. (2012) Analytical tools for characterizing biopharmaceuticals and the implications for biosimilars. Nat Rev Drug Discov., 11(7), 527-540
Non Patent Literature 12: Rosenberg A S. (2006) Effects of protein aggregates an immunologic perspective. AAPS J., 8(3), E501-507
Non Patent Literature 13: Shinya Honda et al., "Development and Market of Antibody Drug," CMC Publishing Co., Ltd. (2012)
Non Patent Literature 14: Hober S, Nord K and Linhult M. (2007) Protein A chromatography for antibody purification. J Chromatogr B Analyt Technol Biomed Life Sci. 848(1) 40-47
Non Patent Literature 15: Kanno S, Yanagida Y, Haruyama T, Kobatake E and Aizawa M. (2000) Assembling of engineered IgG-binding protein on gold surface for highly oriented antibody immobilization. J Biotechnol. 76(2-3) 207-214
Non Patent Literature 16: Buchner J, Renner M, Lilie H, Hinz H J, Jaenicke R, Kiefhabel T and Rudolph R. (1991) Alternatively folded states of an immunoglobulin. Biochemistry. 30(28) 6922-6929
Non Patent Literature 17: Thies M J, Kammermeier R, Richter K and Buchner J. (2001) The alternatively folded state of the antibody C(H)3 domain. J. Mol. Biol. 309(5) 1077-1085
Non Patent Literature 18: Feige M J, Simpson E R, Herold E M, Bepperling A, Heger K and Buchner J. (2010) Dissecting the alternatively folded state of the antibody Fab fragment. J. Mol. Biol. 399(5) 719-730
Non Patent Literature 19: Folding of Protein, Second Edition, R. H. Pain, Springer-Verlag GmbH
Non Patent Literature 20: Kanmert D, Brorsson A C, Jonsson B H and Enander K. (2011) Thermal induction of an alternatively folded state in human IgG-Fc. Chemistry. 50(6) 981-988
Non Patent Literature 21: Luo Q, Joubert M K, Stevenson R, Ketchem R R, Narhi L O and Wypych J. Chemical modifications in therapeutic protein aggregates generated under different stress conditions. (2011) J. Biol. Chem. 2011 286(28) 25134-25144
Non Patent Literature 22: Joubert M K, Hokom M, Eakin C, Zhou L, Deshpande M, Baker M P, Goletz T J, Kerwin B A, Chirmule N, Narhi L O and Jawa V. (2012) Highly aggregated antibody therapeutics can enhance the in vitro innate and late-stage T-cell immune responses. J. Biol. Chem. 287(30) 25266-25279
Non Patent Literature 23: Yoshitake S, Yamada Y, Ishikawa E and Masseyeff R. (1979) Conjugation of glucose oxidase from *Aspergillus niger* and rabbit antibodies using N-hydroxysuccinimide ester of N-(4-carboxycyclohexyl-methyl)-maleimide. Eur. J. Biochem. 101(2) 395-399
Non Patent Literature 24: Tairo Oshima, Koichi Suzuki, Yoshiaki Fujii, Takashi Muramatsu, Post Sequence Protein Experimental Method 3, Tokyo Kagaku Dojin
Non Patent Literature 25: Brymora A, Valova V A and Robinson P J. (2004) Protein-protein interactions identified by pull-down experiments and mass spectrometry. Curr Protoc Cell Biol. 17 Unit 17.5
Non Patent Literature 26: Wittig I and Schagger H. (2009) Native electrophoretic techniques to identify protein-protein interactions. Proteomics. 9(23) 5214-23
Non Patent Literature 27: Park S H and Raines R T. (2004) Fluorescence polarization assay to quantify protein-protein interactions. Methods Mol Biol. 261 161-166
Non Patent Literature 28: Braisted A C and Wells J A. (1996) Minimizing a binding domain from protein A. Proc Natl Acad Sci USA. 93(12) 5688-5692
Non Patent Literature 29: Watanabe H, Matsumaru H, Ooishi A, Feng Y, Odahara T, Suto K and Honda S. Optimizing pH response of affinity between protein G and IgG Fc: how electrostatic modulations affect protein-protein interactions. (2009) J Biol Chem. 284(18) 12373-12383
Non Patent Literature 30: Bio-pharmaceutical Handbook, edited by the Bio-Virus Safety Committee, the Parental Drug Association Japan Chapter, Jiho Inc.

SUMMARY OF INVENTION

Technical Problem

An object of the present invention is to provide a novel polypeptide, which has binding activity to an Fc region of immunoglobulin G and can be favorably used in detecting, purifying, immobilizing or removing an antibody, immunoglobulin G or a protein containing an Fc region of immunoglobulin G, and to increase the molecular diversity of an antibody-binding polypeptide available in industries.

Solution to Problem

The present inventors have conducted intensive studies with a view to attaining the above object. As a result, they found that short polypeptides having predetermined amino acid sequence patterns have high binding activity to human IgG antibodies. In addition, they found that these polypeptides, when they bind to a human IgG antibody, dissociate at a low rate and easily maintain the binding state. They further found that some of these polypeptides bind only to a non-native structure of a human IgG antibody obtained by an acid treatment or a reduction treatment. The present invention was accomplished based on these findings. Note that, in the specification, the terms of "peptide," "polypeptide" and "protein" will be interchangeably used.

More specifically, the present invention includes the followings.

[1] A polypeptide exhibiting binding activity to an Fc region of immunoglobulin G, wherein the polypeptide is a polypeptide consisting of an amino acid sequence represented by the following formula 1:

(SEQ ID NO: 1)
Y-D-P-x-T-G-T-W-R-S-x-[IL]  (1)

where x represents any amino acid residue; and amino acid residues within the square brackets indicate that any one of the amino acid residues is selected,
or a polypeptide consisting of an amino acid sequence having addition of one or several amino acid residues in the amino acid sequence (represented by formula 1);

[2] The polypeptide according to [1], consisting of an amino acid sequence represented by any one of SEQ ID NOs: 2 to 6:

```
                                          (SEQ ID NO: 2)
YDPRTGTWRSSIAYGGG (SEQ ID NO: 3)
YDPGTGTWRSYLRFGGG (SEQ ID NO: 4)
YDPYTGTWRSSIWVLSG (SEQ ID NO: 5)
YDPGTGTWRSWLSFNVG (SEQ ID NO: 6)
YDPWTGTWRSFIWGGGG.
```

[3] A polypeptide exhibiting binding activity to an Fc region of immunoglobulin G, wherein the polypeptide consists of an amino acid sequence obtained by addition, deletion, substitution or insertion of one or several amino acid residues in the amino acid sequence represented by any one of SEQ ID NOs: 2 to 6;

[4] The polypeptide according to [3], consisting of an amino acid sequence represented by any one of SEQ ID NOs: 7 to 9:

```
                                          (SEQ ID NO: 7)
YDPRTGTWLLYASRLLG (SEQ ID NO: 8)
YDPVTGTWTSSIASWMG (SEQ ID NO: 9)
YDPRTGTWRRSSLSYSG.
```

[5] A polypeptide exhibiting binding activity to an Fc region of immunoglobulin G, wherein the polypeptide is a polypeptide consisting of an amino acid sequence represented by the following formula 2:

```
                                          (SEQ ID NO: 10)
R-[QRS]-x-x-[GS]-Y-D-P-R-T-G-T-W-R-S-S-I-A-Y-G-G
``` where x represents any amino acid residue; and amino acid residues within the square brackets indicate that any one of the amino acid residues is selected,
or a polypeptide consisting of an amino acid sequence having addition of one or several amino acid residues in the amino acid sequence represented by formula 2;

[6] The polypeptide according to [5], consisting of an amino acid sequence represented by any one of SEQ ID NOs: 11 to 14:

```
                                          (SEQ ID NO: 11)
GVVRQWSGYDPRTGTWRSSIAYGGG (SEQ ID NO: 12)
AGSRRAHGYDPRTGTWRSSIAYGGG
```

```
                                          (SEQ ID NO: 13)
ASVRSWSSYDPRTGTWRSSIAYGGG (SEQ ID NO: 14)
SWRRRGSSYDPRTGTWRSSIAYGGG.
```

[7] A polypeptide exhibiting binding activity to an Fc region of immunoglobulin G, wherein the polypeptide consists of an amino acid sequence obtained by addition, deletion, substitution or insertion of one or several amino acid residues in the amino acid sequence represented by any one of SEQ ID NOs: 11 to 14;

[8] The polypeptide according to [7], consisting of an amino acid sequence represented by any one of SEQ ID NOs: 15 to 19 and 158 to 164:

```
                                          (SEQ ID NO: 15)
TGRGRSARYDPRTGTWRSSIAYGGG (SEQ ID NO: 16)
HWVNGRSGYDPRTGTWRSSIAYGGG (SEQ ID NO: 17)
ERWITWSGYDPRTGTWRSSIAYGGG (SEQ ID NO: 18)
GSVVRWRGYDPRTGTWRSSIAYGGG (SEQ ID NO: 19)
GAVYRRSFYDPRTGTWRSSIAYRGG (SEQ ID NO: 158)
GVVRRWSGYDPRTGTWRSSIAYGGG (SEQ ID NO: 159)
GVVRQAQSGYDPRTGTWRSSIAYGGG (SEQ ID NO: 160)
GVVRQWAGYDPRTGTWRSSIAYGGG (SEQ ID NO: 161)
GVVRQWSGYDPRTGTWASSIAYGGG (SEQ ID NO: 162)
GVVRQWSGYDPRTGTWRASIAYGGG (SEQ ID NO: 163)
GVVRQWSGYDPRTGTWRSAIAYGGG (SEQ ID NO: 164)
GVVRQWSGYDPRTGTWRSSAAYGGG.
```

[9] A polypeptide exhibiting binding activity to an Fc region of immunoglobulin G, wherein the polypeptide is a polypeptide consisting of an amino acid sequence represented by the following formula 3:

```
                                          (SEQ ID NO: 20)
G-V-V-R-Q-W-S-G-x-x-x-x-x-x-x-x-R-S-S-I-A-Y-G-G
``` where x represents any amino acid residue, or a polypeptide consisting of an amino acid sequence having addition of one or several amino acid residues in the amino acid sequence represented by formula 3;

[10] The polypeptide according to [9], consisting of an amino acid sequence represented by SEQ ID NO: 21:

```
                                          (SEQ ID NO: 21)
GVVRQWSGGGGSGGGGRSSIAYGGG.
```

[11] A polypeptide exhibiting binding activity to an Fc region of immunoglobulin G, wherein the polypeptide consists of an amino acid sequence represented by SEQ ID NO: 22:

```
                                        (SEQ ID NO: 22)
RSSIAYGGG.
```

[12] A polypeptide exhibiting binding activity to an Fc region of immunoglobulin G, wherein the polypeptide is a polypeptide consisting of an amino acid sequence represented by the following formula 4:

```
                                        (SEQ ID NO: 23)
D-A-A-W-H-L-G-E-L-V-W-A-T-Y-Y-D-P-E-T-G-T-W-x-P-D-
W-x-x-M  (4)
``` where x represents any amino acid residue, or a polypeptide consisting of an amino acid sequence having addition of one or several amino acid residues in the amino acid sequence represented by formula 4;

[13] The polypeptide according to [12], consisting of an amino acid sequence represented by any one of SEQ ID NOs: 24 to 54:

```
                                        (SEQ ID NO: 24)
DAAWHLGELVWATYYDPETGTWQPDWLYMTTR (SEQ ID NO: 25)
DAAWHLGELVWATYYDPETGTWAPDWRLMQGQ (SEQ ID NO: 26)
DAAWHLGELVWATYYDPETGTWLPDWQTMAQK (SEQ ID NO: 27)
DAAWHLGELVWATYYDPETGTWEPDWQRMLGQ (SEQ ID NO: 28)
DAAWHLGELVWATYYDPETGTWQPDWRAMSGR (SEQ ID NO: 29)
DAAWHLGELVWATYYDPETGTWRPDWKWMSTH (SEQ ID NO: 30)
DAAWHLGELVWATYYDPETGTWEPDWKLMQRP (SEQ ID NO: 31)
DAAWHLGELVWATYYDPETGTWQPDWDIMAGH (SEQ ID NO: 32)
DAAWHLGELVWATYYDPETGTWLPDWDVMVRQ (SEQ ID NO: 33)
DAAWHLGELVWATYYDPETGTWVPDWERMKQH (SEQ ID NO: 34)
DAAWHLGELVWATYYDPETGTWEPDWSKMRPQ (SEQ ID NO: 35)
DAAWHLGELVWATYYDPETGTWRPDWAVMATP (SEQ ID NO: 36)
DAAWHLGELVWATYYDPETGTWKPDWRMMGVP (SEQ ID NO: 37)
DAAWHLGELVWATYYDPETGTWLPDWDYMSSK (SEQ ID NO: 38)
DAAWHLGELVWATYYDPETGTWMPDWDRMLRR (SEQ ID NO: 39)
DAAWHLGELVWATYYDPETGTWTPDWNAMSQR (SEQ ID NO: 40)
DAAWHLGELVWATYYDPETGTWQPDWKRMTSR (SEQ ID NO: 41)
DAAWHLGELVWATYYDPETGTWQPDWGRMNSK (SEQ ID NO: 42)
DAAWHLGELVWATYYDPETGTWAPDWNRMRDFNRSFREV (SEQ ID NO: 43)
DAAWHLGELVWATYYDPETGTWVPDWDAMSSR (SEQ ID NO: 44)
DAAWHLGELVWATYYDPETGTWIPDWTRMQTW (SEQ ID NO: 45)
DAAWHLGELVWATYYDPETGTWKPDWQRMKLH (SEQ ID NO: 46)
DAAWHLGELVWATYYDPETGTWLPDWSQMRPQ (SEQ ID NO: 47)
DAAWHLGELVWATYYDPETGTWLPDWDTMTPR (SEQ ID NO: 48)
DAAWHLGELVWATYYDPETGTWQPDWSVMKSL (SEQ ID NO: 49)
DAAWHLGELVWATYYDPETGTWVPDWDTMHAAINRSFREV (SEQ ID NO: 50)
DAAWHLGELVWATYYDPETGTWIPDWRAMSQF (SEQ ID NO: 51)
DAAWHLGELVWATYYDPETGTWLPDWNLMGQH (SEQ ID NO: 52)
DAAWHLGELVWATYYDPETGTWRPDWARMEPM (SEQ ID NO: 53)
DAAWHLGELVWATYYDPETGTWKPDWQVMSPVSNRSFREV (SEQ ID NO: 54)
DAAWHLGELVWATYYDPETGTWQPDWEIMRPF.
```

[14] A polypeptide exhibiting binding activity to an Fc region of immunoglobulin G, wherein the polypeptide consists of an amino acid sequence obtained by addition, deletion, substitution or insertion of one or several amino acid residues in the amino acid sequence represented by any one of SEQ ID NOs: 24 to 54;

[15] The polypeptide according to [14], consisting of an amino acid sequence represented by SEQ ID NO: 55:

```
                                        (SEQ ID NO: 55)
EAWHLGELVWATYYDPETGTWRPDWSRMSGR.
```

[16] A polypeptide exhibiting binding activity to an Fc region of immunoglobulin G, wherein the polypeptide is a polypeptide consisting of an amino acid sequence represented by the following formula 5:

```
                                                (SEQ ID NO: 56)
[RSG]-[AGV]-x-Y-D-P-E-T-G-T-W-Y-D-A-A-W-H-L-G-E-L-

V-W-A-T-Y-Y-D-P-E-T-G-T-W-E-P-D-W-Q-R-M-L-G-Q (5)
``` where x represents any amino acid residue; and amino acid residues within the square brackets indicate that any one of the amino acid residues is selected.

where x represents any amino acid residue; and amino acid residues within the square brackets indicate that any one of the amino acid residues is selected, or a polypeptide consisting of an amino acid sequence having addition of one or several amino acid residues in the amino acid sequence represented by formula 5;

[17] The polypeptide according to [16], consisting of an amino acid sequence represented by any one of SEQ ID NOs: 57 to 72:

```
                                    (SEQ ID NO: 57)
GPGISAFSPGRGVYDPETGTWYDAAWHLGELVWATYYD
PETGTWEPDWQRMLGQ (SEQ ID NO: 58)
VISLGSDRGVYDPETGTWYDAAWHLGELVWATYYDPET
GTWEPDWQRMLGQ (SEQ ID NO: 59)
IMSVDGSSARYDPETGTWYDAAWHLGELVWATYYDPET
GTWEPDWQRMLGQ (SEQ ID NO: 60)
VDLRAHGGAVYDPETGTWYDAAWHLGELVWATYYDPET
GTWEPDWQRMLGQ (SEQ ID NO: 61)
WSRFSSRSVAYDPETGTWYDAAWHLGELVWATYYDPET
GTWEPDWQRMLGQ (SEQ ID NO: 62)
GNPSDSASAWYDPETGTWYDAAWHLGELVWATYYDPET
GTWEPDWQRMLGQ (SEQ ID NO: 63)
SNFVRSPSAWYDPETGTWYDAAWHLGELVWATYYDPET
GTWEPDWQRMLGQ (SEQ ID NO: 64)
IPYGFPGRGEYDPETGTWYDAAWHLGELVWATYYDPET
GTWEPDWQRMLGQ (SEQ ID NO: 65)
GPYNIPDSAVYDPETGTWYDAAWHLGELVWATYYDPET
GTWEPDWQRMLGQ (SEQ ID NO: 66)
WPLNAPSSAFYDPETGTWYDAAWHLGELVWATYYDPET
GTWEPDWQRMLGQ (SEQ ID NO: 67)
VPPRFSSSAQYDPETGTWYDAAWHLGELVWATYYDPET
GTWEPDWQRMLGQ (SEQ ID NO: 68)
FLVGLHAGAVYDPETGTWYDAAWHLGELVWATYYDPET
GTWEPDWQRMLGQ (SEQ ID NO: 69)
VVRVDHSSAVYDPETGTWYDAAWHLGELVWATYYDPET
GTWEPDWQRMLGQ (SEQ ID NO: 70)
WMEFYPGRGVYDPETGTWYDAAWHLGELVWATYYDPET
GTWEPDWQRMLGQ (SEQ ID NO: 71)
DGVGPGSRGVYDPETGTWYDAAWHLGELVWATYYDPET
GTWEPDWQRMLGQ (SEQ ID NO: 72)
FVSSLPNSAMYDPETGTWYDAAWHLGELVWATYYDPET
GTWEPDWQRMLGQ.
```

[18] A polypeptide exhibiting binding activity to an Fc region of immunoglobulin G, wherein the polypeptide consists of an amino acid sequence obtained by addition, deletion, substitution or insertion of one or several amino acid residues in the amino acid sequence represented by any one of SEQ ID NOs: 57 to 72;

[19] The polypeptide according to [18], consisting of an amino acid sequence represented by any one of SEQ ID NOs: 73 to 81 and 174 to 178:

```
                                    (SEQ ID NO: 73)
GRAFSGSRRWYDPETGTWYDAAWHLGELVWATYY
DPETGTWAPDWRLMQGQ (SEQ ID NO: 74)
VMATEVVRGVYDPETGTWYDATWHLGELVWATYY
DPETGTWEPDWQRMLGQ (SEQ ID NO: 75)
MMVRPPRLGVYDPEPGTWYDATWHLGELVWATYY
DPETGTWEPDWQRMLGQ (SEQ ID NO: 76)
ERHLVSDYLHYDPETGTWYDAAWHLGELVWATYY
DPETGTWEPDWQRMLGQ (SEQ ID NO: 77)
FSDLDSFGVSYDPETGTWYDAAWHRGELVWATYY
DPETGTWEPDWQRMLGQ (SEQ ID NO: 78)
LFDNKLKHASYDPETGTWYDAAWHLGELVWATYY
DPETGTWEPDWQRMLGQ (SEQ ID NO: 79)
GSCKFSSSCHYDPETGTWYDAAWHLGELVWATYY
DPETGTWEPDWQRMLGQ (SEQ ID NO: 80)
LIPPGGISPWYDPETGTWYDAAWHLGELVWATYY
DPETGTWEPDWQRMLGQ (SEQ ID NO: 81)
LNDFLTPTAWYDPETGTWYDAAWHLGELVWATYY
DPETGTWLPDWQTMAQK (SEQ ID NO: 174)
GPGISAFSPGRGVYDPETGTWYDAAWHLGELVWA
TYYDPETGTWEADWQRMLGQ (SEQ ID NO: 175)
GPGISAFSPGRGVYDPETGTWYDAAWHLGELVWA
TYYDPETGTWEPAWQRMLGQ
```

-continued

GPGISAFSPGRGVYDPETGTWYDAAWHLGELVWA   (SEQ ID NO: 176)

TYYDPETGTWEPDAQRMLGQ

GPGISAFSPGRGVYDPETGTWYDAAWHLGELVWA   (SEQ ID NO: 177)

TYYDPETGTWEPDWQAMLGQ

GPGISAFSPGRGVYDPETGTWYDAAWHLGELVWA   (SEQ ID NO: 178)

TYYDPETGTWEPDWQRALGQ.

[20] A polypeptide exhibiting binding activity to an Fc region of immunoglobulin G, wherein the polypeptide is a tandem polypeptide formed by linking a second polypeptide to an amino terminal or a carboxyl terminal or both terminals of the polypeptide according to any one of [1], [3], [5], [7], [9], [12], [14], [16] and [18];

[21] The polypeptide according to [20], which is a tandem polypeptide formed by linking a second polypeptide to an amino terminal or a carboxyl terminal or both terminals of the polypeptide of any one of SEQ ID NOs: 2 to 9, 11 to 19, 21, 22, 24 to 55, 57 to 81, 158 to 164 and 174 to 178;

[22] A protein exhibiting binding activity to an Fc region of immunoglobulin G, wherein the protein is a fusion protein formed by binding a protein to the amino terminal or carboxyl terminal or both terminals of the polypeptide according to any one of [1], [3], [5], [7], [9], [12], [14], [16] and [18];

[23] The protein according to [22], which is a fusion protein formed by binding a protein to the amino terminal or carboxyl terminal or both terminals of the polypeptide of any one of SEQ ID NOs: 2 to 9, 11 to 19, 21, 22, 24 to 55, 57 to 81, 158 to 164 and 174 to 178;

[24] The protein according to [22], consisting of an amino acid sequence represented by any one of SEQ ID NOs: 82 to 119;

[25] A nucleic acid encoding the polypeptide or protein according to any one of [1] to [24];

[26] The nucleic acid according to [25], consisting of a nucleotide sequence represented by any one of SEQ ID NOs: 120 to 157 and 179 to 183;

[27] A recombinant vector comprising the nucleic acid according to [25] or [26];

[28] A transformant comprising the recombinant vector according to [27] introduced therein;

[29] A recombinant phage or recombinant virus comprising the nucleic acid according to [25] or [26];

[30] A polypeptide or protein exhibiting binding activity to an Fc region of immunoglobulin G, wherein the polypeptide or protein is a modified polypeptide or modified protein formed by binding an organic compound or an inorganic compound or both of an organic compound and an inorganic compound to any one of the polypeptides according to [1], [3], [5], [7], [9], [12], [14], [16] and [18], the tandem polypeptide according to [20] and the fusion protein according to [22];

[31] A polypeptide or protein exhibiting binding activity to an Fc region of immunoglobulin G, wherein the polypeptide or protein is a modified polypeptide or modified protein formed by binding an organic compound or an inorganic compound or both of an organic compound and an inorganic compound to any one of the polypeptides according to SEQ ID NOs: 2 to 9, 11 to 19, 21, 22, 24 to 55, 57 to 81, 158 to 164 and 174 to 178 and the fusion proteins of SEQ ID NOs: 82 to 119;

[32] An immobilized polypeptide or immobilized protein, obtained by immobilizing the polypeptide according to any one of [1] to [21], the protein according to any one of [22] to [24] or the polypeptide or protein according to either one of [30] and [31] to a solid phase support insoluble in water;

[33] A kit for detecting, purifying, immobilizing or removing an antibody, immunoglobulin G or a protein containing an Fc region of immunoglobulin G, comprising at least one selected from the group consisting of the polypeptide according to any one of [1] to [21], the protein according to any one of Claims [22] to [24], the nucleic acid according to either one of [25] and [26], the recombinant vector according to [27], the transformant according to [28], the recombinant phage or recombinant virus according to [29], the polypeptide or protein according to either one of [30] and [31] and the immobilized polypeptide or immobilized protein according to [32];

[34] A method for detecting an antibody, immunoglobulin G or Fc region-containing protein having a non-native conformation, in a test sample, comprising the steps of:

(1) bringing the test sample into contact with the polypeptide according to any one of [1] to [21], the protein according to any one of [22] to [24], the transformant according to [28], the recombinant phage or recombinant virus according to [29], the polypeptide or protein according to either one of [30] and [31] or the immobilized polypeptide or immobilized protein according to [32], and (2) determining whether a bond is formed or not between the test sample and the polypeptide, protein, transformant, recombinant phage or recombinant virus, or immobilized polypeptide or immobilized protein;

[35] A method for purifying an antibody, immunoglobulin G or Fc region-containing protein having a non-native conformation, comprising the steps of:

(1) bringing a sample containing the antibody, immunoglobulin G or Fc region-containing protein having a non-native conformation into contact with the polypeptide according to any one of [1] to [21], the protein according to any one of [22] to [24], the transformant according to [28], the recombinant phage or recombinant virus according to [29], the polypeptide or protein according to either one of [30] and [31], or the immobilized polypeptide or immobilized protein according to [32] to thereby allow the antibody, immunoglobulin G or Fc region-containing protein having a non-native conformation to bind to the polypeptide, protein, transformant, recombinant phage or recombinant virus, or immobilized polypeptide or immobilized protein, and (2) recovering the antibody, immunoglobulin G or Fc region-containing protein having a non-native conformation and bound to the polypeptide, protein, transformant, recombinant phage or recombinant virus, or immobilized polypeptide or immobilized protein from the sample;

[36] A method for removing an antibody, immunoglobulin G or Fc region-containing protein having a non-native conformation, comprising the steps of:

(1) bringing a sample containing the antibody, immunoglobulin G or Fc region-containing protein having a non-native conformation into contact with the polypeptide according to any one of [1] to [21], the protein according to any one of [22] to [24], the transformant according to [28], the recombinant phage or recombinant virus according to [29], the polypeptide or protein according to either one of [30] and [31], or the immobilized polypeptide or immobilized protein according to [32] to thereby allow the antibody, immunoglobulin G or Fc region-containing protein having a non-native conformation to bind to the polypeptide, protein, transformant, recombinant phage or recombinant virus, or immobilized polypeptide or immobilized protein, and (2) removing the antibody, immunoglobulin G or Fc region-containing protein having a non-native conformation and bound to the polypeptide, protein, transformant, recombinant phage or recombinant virus, or immobilized polypeptide or immobilized protein from the sample; and

[37] The method according to any one of [34] to [36], carried out under a reductive environment.

Advantageous Effects of Invention

The polypeptides of the present invention have high binding activity to a human IgG antibody. In addition, when the polypeptides of the present invention bind to a human IgG antibody, they dissociate at a low rate. Furthermore, some of these polypeptides bind only to a non-native structure of a human IgG antibody obtained by an acid treatment or a reduction treatment and does not bind to a natural IgG antibody. Antibody immunoglobulin G (IgG) or a fusion protein obtained by adding an Fc region of IgG can be e.g., immobilized, detected, purified or removed by use of the IgG-binding polypeptide of the present invention.

Polypeptide 2A1 (SEQ ID NO: 11) having the amino acid sequence represented by SEQ ID NO: 10 as a common amino acid sequence, unlike from a general IgG-binding molecule, does not bind to natural IgG at all, and specifically binds to a non-native structure obtained by e.g., an acid treatment or a reduction treatment. This property can be used for immobilization, detection, purification or removal of IgG having a non-native structure. As described in Example 1, 4) described later, polypeptide 2A1 exhibits binding activity to an Fc region exposed to a reductive condition. Furthermore, as shown in Example 1, 8) described later, polypeptide 2A1 exhibits a high heat inactivation resistance.

Polypeptide p17 (SEQ ID NO: 57) having the amino acid sequence represented by SEQ ID NO: 56 as a common amino acid sequence can bind to an Fc region with an equilibrium dissociation constant of $K_D=1.6$ nM. This value exhibits extremely high binding activity as far as a linear polypeptide is concerned and is higher even if compared to a cyclic peptide, whose binding activity is generally higher than that of a linear polypeptide; more specifically, exhibits the binding activity of the highest rank beyond the value of cyclic peptide FcBP-2 ($K_D=2.2$ nM) (Dias et al., Non Patent Literature 4), which has been reported to have high binding activity. Such a polypeptide having high binding activity compared to conventional IgG-binding proteins and IgG-binding peptides can be favorably used for immobilization detection, purification or removal of IgG and an Fc region fusion protein.

Since the IgG-binding polypeptide of the present invention does not depend upon stabilization through cyclization, a complicated chemical reaction for cyclization is not required. In addition, the IgG-binding polypeptide can exhibit a binding function even under a condition such as a reductive condition where a disulfide crosslinkage is not easily formed.

Figure 1:
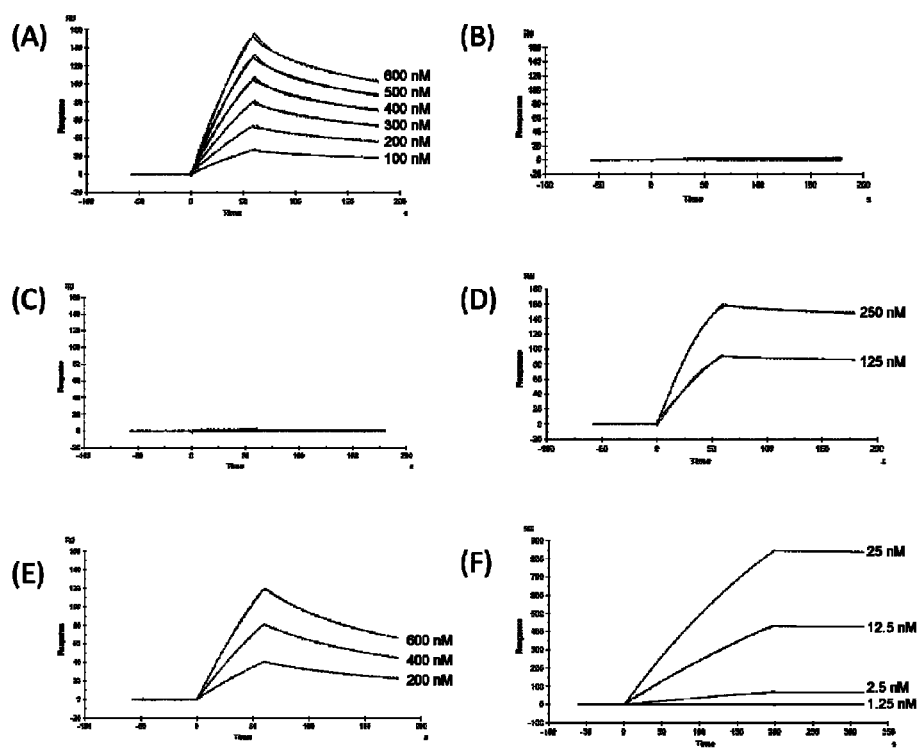
FIG. 1 (A) shows the results of binding activity of 2A1 to a human Fc region (Jackson ImmunoResearch Laboratories, Inc.) measured by surface plasmon resonance, more specifically, shows the binding curves of individual samples of the human Fc region (prepared by diluting human Fc region to have concentrations of 600, 500, 400, 300, 200 and 100 nM) to 2A1 immobilized to a sensor chip; (B) shows the results of binding activity of 2A1 to natural human monoclonal IgG measured by surface plasmon resonance; more specifically, shows the binding curves of individual samples of the natural IgG (prepared by diluting the natural IgG to have concentrations of 600, 500, 400, 300, 200 and 100 nM) to 2A1 immobilized to a sensor chip; (C) shows the results of binding activity of 2A1 to a natural human Fc region measured by surface plasmon resonance; more specifically, shows the binding curves of individual samples of the natural human Fc region (prepared by diluting the natural human Fc region to have concentrations of 600, 500, 400, 300, 200 and 100 nM) to 2A1 immobilized to a sensor chip; (D) shows the results of binding activity of 2A1 to acid-denatured human IgG measured by surface plasmon resonance; more specifically, shows the binding curves of individual samples of the acid-denatured human IgG (prepared by diluting the acid-denatured human IgG to have concentrations of 250 and 125 nM) to 2A1 immobilized to a sensor chip; (E) shows the results of binding activity of 2A1 to a human Fc region treated in a reductive condition measured by surface plasmon resonance; more specifically shows the binding curves of individual samples of the human Fc region treated in a reductive condition (prepared by diluting human Fc region treated in a reductive condition to have concentrations of 600, 400 and 200 nM) to 2A1 immobilized to a sensor chip; and (F) shows the results of binding activity of 2A1 to AFS human IgG measured by surface plasmon resonance; more specifically shows the binding curves of individual samples of the AFS human IgG (prepared by diluting the AFS human IgG to have concentrations of 25, 12.5, 2.5 and 1.25 nM) to 2A1 immobilized to a sensor chip.

The specification contains the content described in the specification of Japanese Patent Application No. 2013-13217 based on which the priority right of the present application was claimed.

DESCRIPTION OF EMBODIMENTS

The present invention relates to a polypeptide exhibiting binding activity to immunoglobulin G and an Fc region thereof and a method for detecting, immobilizing, purifying or removing immunoglobulin G and an Fc region thereof by use of the polypeptide.

A preferred embodiment of the polypeptide of the present invention is a polypeptide containing, as a common sequence, an amino acid sequence represented by SEQ ID NO: 1:

```
Y-D-P-x-T-G-T-W-R-S-x-[IL]
``` where x represents any amino acid residue; and amino acid residues within the square brackets indicate that any one of the amino acid residues is selected;
and more preferably, a polypeptide containing an amino acid sequence represented by any one of SEQ ID NOs: 2 to 6. The polypeptide of the present invention includes a polypeptide consisting of an amino acid sequence, which basically contains the common sequence (SEQ ID NO: 1) and may have addition, deletion, substitution or insertion of several amino acid residues (e.g., 1 to 6, preferably 1 to 3, more preferably 1 or 2) as long as the binding activity thereof to an Fc region of immunoglobulin G is not damaged, like polypeptides represented by any one of SEQ ID NOs: 7 to 9 in Example 1 described later. The number of amino acid residues in the polypeptide sequence is not limited as long as the above amino acid sequence is contained. As shown in Example 1, 6) described later, a recombinant phage displaying the polypeptide on the surface layer and obtained by transformation with a nucleic acid encoding the polypeptide also has the binding activity to an Fc region of immunoglobulin G. In short, the present invention includes a polypeptide having the above amino acid sequence, a fusion protein containing the polypeptide and a transformant having a nucleic acid encoding the polypeptide or the fusion protein.

Another preferred embodiment is a polypeptide containing, as a common sequence, an amino acid sequence represented by SEQ ID NO: 10:

```
R-[QRS]-x-x-[GS]-Y-D-P-R-T-G-T-W-R-S-S-I-A-Y-G-G
``` where x represents any amino acid residue; and amino acid residues within the square brackets indicate that any one of the amino acid residues is selected;
and more preferably, a polypeptide containing an amino acid sequence represented by any one of SEQ ID NOs: 11 to 14. The polypeptide of the present invention includes a polypeptide consisting of an amino acid sequence, which basically contains the common sequence (SEQ ID NO: 1) and may have addition, deletion, substitution or insertion of several amino acid residues (e.g., 1 to 10, preferably 1 to 6, more preferably 1 to 3) as long as the binding activity thereof to an Fc region of immunoglobulin G is not damaged, like a polypeptide represented by any one of SEQ ID NOs: 15 to 21 in Example 1 described later. The number of amino acid residues in the polypeptide sequence is not limited as long as the above amino acid sequence is contained. As shown in Example 1, 5) and 6) described later, the fusion protein having the polypeptide and also a recombinant phage displaying the polypeptide on the surface layer and obtained by transformation with a nucleic acid encoding the polypeptide have the binding activity. In short, the present invention includes a polypeptide having the above amino acid sequence, a fusion protein containing the polypeptide and a transformant having a nucleic acid encoding the polypeptide or the fusion protein.

Another preferred embodiment is a polypeptide containing, as a common sequence, an amino acid sequence represented by SEQ ID NO: 23:

```
D-A-A-W-H-L-G-E-L-V-W-A-T-Y-Y-D-P-E-T-G-T-W-x-P-D-
W-x-x-M
``` where x represents any amino acid residue;
and more preferably a polypeptide containing an amino acid sequence represented by any one of SEQ ID NOs: 24 to 54. The polypeptide of the present invention includes a polypeptide consisting of an amino acid sequence, which basically contains the common sequence (SEQ ID NO: 23) and may have addition, deletion, substitution or insertion of several amino acid residues (e.g., 1 to 10, preferably 1 to 6, more preferably 1 to 3) as long as the binding activity thereof to an Fc region of immunoglobulin G is not damaged, like a polypeptide represented by SEQ ID NO: 55 in Example 2 described later. The number of amino acid residues in the polypeptide sequence is not limited as long as the above amino acid sequence is contained. As shown in Example 2, 5) and 6) described later, the fusion protein having the polypeptide and also a recombinant phage displaying the polypeptide on the surface layer and obtained by transformation with a nucleic acid encoding the polypeptide have the binding activity. In short, the present invention includes a polypeptide having the above amino acid sequence, a fusion protein and a transformant having a nucleic acid encoding the polypeptide and/or the fusion protein.

Another preferred embodiment is a polypeptide containing, as a common sequence, an amino acid sequence represented by SEQ ID NO: 56:

[RSG]-[AGV]-x-Y-D-P-E-T-G-T-W-Y-D-A-A-W-H-L-G-E-L-
V-W-A-T-Y-Y-D-P-E-T-G-T-W-E-P-D-W-Q-R-M-L-G-Q where x represents any amino acid residue; and amino acid residues within the square brackets indicate that any one of the amino acid residues is selected;
and more preferably a polypeptide containing an amino acid sequence represented by any one of SEQ ID NOs: 57 to 72. The polypeptide of the present invention includes a polypeptide consisting of an amino acid sequence, which basically contains the common sequence (SEQ ID NO: 56) and may have addition, deletion, substitution or insertion of several amino acid residues (e.g., 1 to 10, preferably 1 to 6, more preferably 1 to 3) as long as the binding activity thereof to an Fc region of immunoglobulin G is not damaged, like a polypeptide represented by any one of SEQ ID NOs: 73 to 81 in Example 2 described later. The number of amino acid residues in the polypeptide sequence is not limited as long as the above amino acid sequence is contained. As shown in Example 2, 5) and 6) described later, the fusion protein having the polypeptide and also a recombinant phage displaying the polypeptide on the surface layer and obtained by transformation with a nucleic acid encoding the polypeptide have the binding activity. In short, the present invention includes a polypeptide having the above amino acid sequence exhibiting binding activity to an Fc region, a fusion protein and a transformant having a nucleic acid encoding the polypeptide and/or the fusion protein.

The polypeptide and protein of the present invention may have a label. More specifically, the present invention may include a modified polypeptide or modified protein prepared by binding an organic compound or an inorganic compound or both of an organic compound and inorganic compound to the above polypeptide or fusion protein as long as the binding activity to an Fc region of immunoglobulin G is not damaged. Owing to binding of the above organic compound and the like, immobilization, purification, detection or removal (which is an example of use of the present invention as described below) of an antibody, immunoglobulin G or a protein containing an Fc region of immunoglobulin G, can be efficiently performed. Preferred examples of the organic compound and the like to be used may include biotin, fluorescent organic compounds such as fluorescein, a stable isotope, a phosphoric acid group, an acyl group, an amide group, an ester group, an epoxy group, polyethylene glycol (PEG), a lipid, a sugar chain, and a nucleic acid; and fluorescent inorganic compounds such as a quantum dot; and colloidal gold (Basle E, Joubert N, Pucheault M, Protein chemical modification on endogenous amino acids. Chem Biol. 2010, 17(3), 213-27.); however, other compounds, as long as they are technically applicable, may not be excluded.

Use of the polypeptide of the present invention is not limited as long as the binding activity of the polypeptide molecule to an Fc region of immunoglobulin G is used. Generally, an artificially prepared immunoglobulin G-binding polypeptide or an immunoglobulin G-binding protein derived from a microorganism is used for immobilization, purification, detection or removal of an antibody, immunoglobulin G or a protein containing an Fc region of immunoglobulin G (Non Patent Literature 14, Non Patent Literature 15, Patent Literature 1, Patent Literature 3, Non Patent Literature 6 and Non Patent Literature 9). Accordingly, examples of use of the polypeptide of the present invention may include not only uses to which the above immunoglobulin G-binding molecule is actually applied but also all uses known to those skilled in the art, to which the present invention is technically applicable. In Examples described later, detection, purification and removal of immunoglobulin G are mentioned; however, other uses may not be excluded.

Of the polypeptides of the present invention, a polypeptide having an amino acid sequence represented by SEQ ID NO: 10 as the common amino acid sequence exhibits a specific binding activity to immunoglobulin G and an Fc region having a non-native structure, as shown in Example 1, 7) described later and thus can be used in immobilization, purification, detection or removal of immunoglobulin G and an Fc region having a non-native structure. The non-native structure used herein is a general term which refers to not a natural structure but a structure produced by e.g., an acid treatment, a heat treatment, a treatment with a chemical denaturant, a treatment with a reducing agent and physical impact such as shearing and stirring.

The acid treatment herein refers to a treatment in which a polypeptide is exposed to a condition of preferably pH 4.0 or less and more preferably pH 1.5 to 2.0. For example, it is reported that if immunoglobulin G is treated with a buffer (10 mM Glycine-HCl, 150 mM NaCl, pH 2.0), a non-native structure (which differs from a general natural structure) called alternatively folded state (AFS), is formed (Non Patent Literature 16, Non Patent Literature 17 and Non Patent Literature 18).

It is generally known that the conformation of a protein is changed not only by an acid treatment but also other chemical treatments or physical treatments. It is most generally known that a conformational change easily occurs by heat or a chemical denaturant such as guanidine hydrochloride (Non Patent Literature 19). More specifically, in an Fc region of immunoglobulin G, it is reported that AFS is formed by heat denaturation in the proximity of 75° C. (Non Patent Literature 20). As the other chemical treatments and physical treatments, a treatment with a reducing agent and physical impact such as shearing and stirring are widely known. The treatment with a reducing agent herein refers to a treatment by which disulfide bonds within a molecule or between molecules are wholly or partly cleaved, more specifically, refers to a treatment of adding a reducing agent (such as DTT, β-mercaptoethanol and 2-mercaptoethylamine) to cleave disulfide bonds. In Examples described later, a reduction treatment was performed with 50 mM 2-mercaptoethylamine for 90 minutes. However, the reagent causing reductive conditions is not limited to this. The physical impact such as stirring and shearing is not limited. For example, it is reported that oxidization of an amino acid residue and conformational change of a protein occur to aggregate the protein by rotating an immunoglobulin G solution by a stirrer at a rate of 700 rpm (Non Patent Literature 21 and Non Patent Literature 22). In Example 1, 7) described later, the measurement results of binding activity to immunoglobulin G and an Fc region treated with acid and/or heat, or a reducing agent and treated under the condition where AFS is formed with acid, are described. Of the non-native structures of immunoglobulin G and an Fc region, to which the polypeptide of the present invention is to be bound, non-native structures other than this are not excluded.

It is conceivable that the polypeptide according to the present invention can be used for immobilization, purification, detection or removal of immunoglobulin and an Fc region under e.g., a reductive condition. The immunoglobulin G-binding polypeptide of the present invention does not depend upon cyclization through disulfide crosslinkage and resultant functionalization/stabilization. Accordingly, the binding function can be exhibited even under reductive conditions where disulfide crosslinkage is not easily formed. The reductive conditions where disulfide crosslinkage is not easily formed are conceivably as follows: (1) a cytoplasmic environment, (2) an environment where a reducing agent is added in order to convert the thiol group of a cysteine residue of target immunoglobulin G or Fc region to a free radical for e.g., chemical modification. In Example 1, 7) described later, an Fc region was treated under a reductive condition using a reducing agent, i.e., 2-mercaptoethylamine (Thermo Scientific Pierce) and the reductive condition was maintained in the presence of a chelating agent, i.e., ethylenediaminetetraacetate (Non Patent Literature 23); however, other conditions are not excluded as long as disulfide crosslinkage is not formed.

In the present invention, the synthesis method for a polypeptide and the embodiment to be used are not limited. As a method for preparing a polypeptide whose amino acid sequence has been identified, various synthesis methods are reported including a synthesis method in an organic chemical manner, a method based on gene recombination (reference literature: Kenji Kangawa, Peptide and Drug Development, Medical Do) and an expression method of a polypeptide in the form of a fusion protein by linking to any protein (reference literature: Tatsuya Moriyama, Protein Purification and Know-how of Handling, YODOSHA Co., Ltd.). Likewise, a polypeptide whose amino acid sequence is specified can be easily prepared by applying an existing synthesis technology. In Examples described later, a preparation by synthesis in an organic chemical manner, a preparation by cellular expression of a fusion protein, a preparation of a desired polypeptide by cleavage of a fusion protein with protease and a preparation of a recombinant phase displaying a polypeptide on a surface layer by transformation with a nucleic acid encoding the polypeptide are disclosed. Other methods including the aforementioned techniques are not excluded.

The present invention also relates to a solid phase carrier to which the polypeptide of the present invention is to be immobilized. Examples of a preferred solid phase carrier herein may include, but are not limited to, resins such as a polystyrene and a polyester; bio-polymers such as dextran and agarose; and inorganic materials such as a metal and glass. These solid phase carrier may have any shape such as a particle, a plate, a film, a chip and a test tube. A polypeptide can be immobilized to these solid phase carriers by a covalent bonding method, a physical adsorption method, an ion bonding method or an intramolecular interaction method. In Examples described later, immobilization to a sensor chip of a surface plasmon resonance measurement apparatus by the covalent bonding method and immobilization to polymer particles used in an affinity chromatography column are mentioned; however, other support carriers and immobilization methods are not excluded, as described above. The polypeptide of the present invention and the molecules containing the polypeptide, such as a fusion protein can be favorably used for immobilization, purification or removal of immunoglobulin G and an Fc region by immobilizing them to a solid phase carrier. In Examples described later, it is stated that immunoglobulin G was purified by affinity chromatography using a column in which a fusion protein containing a polypeptide is immobilized, and that Fab was purified by removing an Fc region from a product obtained by digesting immunoglobulin G with an enzyme, papain. Form of a solid phase carrier and an immobilization method are not limited to this. Protein purification means known to those skilled in the art such as particles (e.g., magnetic particles) and filter membranes can be favorably used. As the target molecule to be purified, other than immunoglobulin G, a fusion protein produced by linking any protein (such as a cytokine and an enzyme) and an Fc region can be also used.

Examples of a method for measuring the binding activity of a polypeptide may include Enzyme Linked Immuno-Sorbent Assay (ELISA), a surface plasmon resonance method (SPR), isothermal titration calorimetry (ITC), quartz crystal microbalance (QCM) method, an atomic force microscopic (AFM) method (for these, see Non Patent Literature 24), a pull-down method (Non Patent Literature 25), an electrophoresis method (Non Patent Literature 26) and a fluorescence polarization measurement method (Non Patent Literature 27). In Examples described later, Enzyme Linked Immuno-Sorbent Assay and a surface plasmon resonance method are described as examples; however, other methods including the above techniques are not excluded.

An antibody, immunoglobulin G or Fc region-containing protein having a non-native conformation in a sample can be detected and separated (purified or removed) by use of the polypeptide and the fusion protein of the present invention.

A method for detecting an antibody, immunoglobulin G or Fc region-containing protein having a non-native conformation in a test sample may include the following steps of:

(1) bringing a test sample into contact with the polypeptide, protein, transformant, recombinant phage or recombinant virus of the present invention, or the polypeptide immobilized or the protein immobilized, and (2) determining whether a bond is formed or not between the test sample and the polypeptide, protein, transformant, recombinant phage or recombinant virus, or the polypeptide immobilized or the protein immobilized.

Examples of the method for use in the step of determining whether a bond is formed or not may include ELISA, SPR, ITC, a QCM method, an AFM method, a pull-down method, an electrophoresis method, a fluorescence polarization measurement method, a fluorescence resonance energy transfer method (FRET), column chromatography and immunochromatography. In Examples described later, a surface plasmon resonance method is disclosed as an example; however, other technically applicable methods including the aforementioned techniques are not excluded.

The method for purifying an antibody, immunoglobulin G or Fc region-containing protein having a non-native conformation may include the following steps of:

(1) bringing a sample containing an antibody, immunoglobulin G or Fc region-containing protein having a non-native conformation into contact with the polypeptide, protein, transformant, recombinant phage or recombinant virus of the present invention, or the polypeptide immobilized or the protein immobilized to allow the antibody, immunoglobulin G or Fc region-containing protein having a non-native conformation to bind to the polypeptide, protein, transformant, recombinant phage or recombinant virus, or the polypeptide immobilized or the protein immobilized, and (2) a step of recovering the antibody, immunoglobulin G or Fc region-containing protein having a non-native conformation bound to the polypeptide, protein, transformant, recombinant phage or recombinant virus, or the polypeptide immobilized or the protein immobilized from the sample.

Examples of the method for use in the recovering step from the sample may include affinity chromatography, an affinity beads method, an affinity filter method and an immunoprecipitation method. In Examples described later, affinity chromatography is used as an example; however, other technically applicable methods including the above techniques are not excluded.

The method for removing an antibody, immunoglobulin G or Fc region-containing protein having a non-native conformation may include the following steps of:

(1) bringing a sample containing an antibody, immunoglobulin G or Fc region-containing protein having a non-native conformation into contact with the polypeptide, protein, transformant, recombinant phage or recombinant virus of the present invention, or the polypeptide immobilized or the protein immobilized to allow the antibody, immunoglobulin G or Fc region-containing protein having a non-native conformation to bind to the polypeptide, protein, transformant, recombinant phage or recombinant virus, or the polypeptide immobilized or the protein immobilized, and (2) removing the antibody, immunoglobulin G or Fc region-containing protein having a non-native conformation bound to the polypeptide, protein, transformant, recombinant phage or recombinant virus, or the polypeptide immobilized or the protein immobilized from the sample.

Examples of the method for use in the removal step from the sample may include affinity chromatography, an affinity beads method, an affinity filter method and an immunoprecipitation method. In Examples described later, an affinity chromatography is used as an example; however, other technically applicable methods including the above techniques are not excluded.

The present invention will be more specifically described by way of Examples; however, the present invention is not limited by these Examples.

Example 1

In this Example, first, how to specify amino acid sequences of many polypeptides exhibiting antibody binding activity will be described and then examples of measuring binding activity of the following substances will be described:

a synthetic polypeptide consisting of amino acid sequences of SEQ ID NOs: 2 to 6 containing an amino acid sequence of SEQ ID NO: 1 as a common sequence; amino acid sequences of SEQ ID NOs: 11 to 14 containing an amino acid sequence of SEQ ID NO: 10 as a common sequence;

amino acid sequences of SEQ ID NOs: 7 to 9 and 15 to 21, which are obtained by addition, deletion, substitution or insertion of several amino acids to these amino acid sequences so as not to lose the binding activity to an Fc region of immunoglobulin G (IgG);

an amino acid sequence of SEQ ID NO: 22, which is a partial sequence of them, fusion proteins containing these amino acid sequences, or recombinant phages transformed by nucleic acids encoding these amino acid sequences.

1) Construction of Polypeptide Library and Selection of Fc Region of Human IgG

The amino acid sequence of a polypeptide exhibiting antibody binding activity was specified by a phage display method using T7 phage.

First, a phage library, which displays a polypeptide consisting of an amino acid sequence:

(SEQ ID NO: 168)
Tyr-Asp-Pro-Xaa-Thr-Gly-Thr-Trp-(Xaa)$_8$-Gly where Xaa represents any amino acid residue,
via a linker consisting of the amino acid sequence:

(SEQ ID NO: 169)
Gly-Gly-Gly-Gly-Ser on the C terminal of coat protein g10 of T7 phage, was constructed by use of T7Select10-3 Cloning Kit (Novagen). Construction was performed completely in accordance with the procedure instructed by the accompanying T7Select (registered trade mark) System Manual (Novagen).

Subsequently, using the T7 phage display library constructed, a phage bound to a target, i.e., an Fc region of human IgG was selected. First, with Streptavidin MagneSphere (registered trade mark) Paramagnetic Particles (Promega Corporation) (0.65 mL), which are avidin-immobilized magnetic beads, 20 μg of an Fc region of human IgG (Jackson ImmunoResearch Laboratories, Inc.) labeled with biotin was mixed and immobilized to the magnetic beads via an avidin-biotin bond. To this, a blocking agent, SuperBlock (registered trade mark) T20 (TBS) Blocking Buffer (Thermo SCIENTIFIC) was added and allowed to stand still for one hour to block magnetic beads having the Fc region immobilized thereto. With this Fc region-immobilized magnetic beads, 1 mL of a solution of the T7 phage display library ($5 \times 10^{12}$ plaque forming units) was allowed to be in contact for one hour to bind the phage displaying a polypeptide exhibiting binding activity to the Fc region to the Fc region-immobilized magnetic beads. Subsequently, a complex of the phage displaying a polypeptide and the Fc region-immobilized magnetic beads was recovered by magnetic separation using MagneSphere (registered trade mark) Technology Magnetic Separation Stand (Promega Corporation). To the complex thus recovered, 1 mL of SuperBlock (registered trade mark) T20 (TBS) Blocking Buffer (Thermo SCIENTIFIC) was added. The mixture was mixed for 10 minutes and again subjected to magnetic separation. The supernatant was removed to recover the complex. This washing operation was performed 10 times. After washing, to the complex recovered by magnetic separation, TBS-T buffer (1 mL) containing 1% (w/v) sodium dodecyl sulfate (SDS) was added. The resultant solution was mixed for 10 minutes to allow the phage displaying a polypeptide having binding activity to elute from the Fc region-immobilized magnetic beads. *Escherichia coli* BLT5403 strain (Novagen), which was previously cultured in a 200 mL LB medium until O.D.600 reached 1.0, was infected with the phage eluted and cultured while shaking for 4 hours. The culture solution was centrifuged at 5000×g for 20 minutes to recover the supernatant (of the medium) containing proliferated phages. To the supernatant, 20 mL of 5 M NaCl (Wako Pure Chemical Industries, Ltd.) and 35 mL of 50% polyethylene glycol (PEG) 8000 (Sigma-Aldrich Corporation) were added. The mixture was stirred at 4° C. for 12 hours and centrifuged at 14000×g for 20 minutes. The precipitate was suspended in 2 mL of TBS-T buffer (50 mM Tris-HCl, 150 mM NaCl, 0.01% (w/v) Tween 20 (registered trade mark) pH 7.4) and filtered by a 0.22 μm-diameter filter to remove aggregates. In this manner, a T7 phage solution was obtained. The aforementioned "step of bringing the library into contact with a target, i.e., an Fc region of human IgG, and a step of selecting a phage bound to the Fc region of human IgG and recovering the phage" were repeated five times to concentrate the phage displaying a polypeptide exhibiting binding activity.

2) Specification of Polypeptide Having Binding Activity by Binding Activity Test Based on ELISA and Sequence Analysis Next, we will describe an example where a molecule having binding activity was specified by ELISA and DNA analysis from phages concentrated.

The phages displaying a polypeptide exhibiting binding activity and concentrated in Example 1, 1) were allowed to form plaques in accordance with T7Select (registered trade mark) System Manual (Novagen). From each plaque, phages displaying a single polypeptide were isolated. To MICROTEST (registered trade mark) 96 (BECTON, DICKINSON AND COMPANY) serving as a 96-well plate, a culture solution (0.2 mL) of *Escherichia coli* BL5403 strain, which was previously cultured in LB medium until O.D.600 reached 1.0, was poured to infect with the *Escherichia coli* cells 96 types of phages isolated from the plaques and allowed to stand still at 37° C. for 12 hours to proliferate phages. The culture solution (10 μL) containing these phages was diluted in 90 μL of TBS buffer (50 mM Tris-HCl, 150 mM NaCl, pH 7.4). The dilution solution was poured to a MEDISORP 96 well microplate (Nunc) and allowed to stand still for one hour to allow the phages to physically adsorb to the plate. After the supernatant was removed, SuperBlock (registered trade mark) T20 (TBS) Blocking Buffer (Thermo SCIENTIFIC) (150 μL) was poured to the plate and allowed to stand still for one hour to block the surface of the plate. The plate was washed three times with TBS-T buffer. To the plate, TBS-T buffer (100 μL) containing an Fc region (Jackson ImmunoResearch Laboratories, Inc.) (0.2 μg/mL) labeled with horseradish peroxidase (HRP) was added and allowed to stand still for one hour. After the plate was washed three times with TBS-T buffer, ABTS One Component HRP Microwell Substrate (BioFX) (100 μL) was poured to the plate. Presence of binding property was detected through a light-emitting reaction. The absorbance at 415 nm was measured by a microplate absorbance reader Sunrise R (TECAN GROUP LTD.). With respect to top 16 types of phages having a high binding activity, the DNA sequence of the region encoding the polypeptide was analyzed by the dideoxy method using ABI PRISM (registered trade mark) 3100 (Applied BioSystems). As a result of the analysis, amino acid sequences represented by SEQ ID NOs: 2 to 9 were specified as the polypeptides having binding activity.

3) Construction of Polypeptide Extension Library and Selection of Fc Region of Human IgG For enhancing the function of the (polypeptide) molecule specified in Example 1, 2), an 8 residue long random sequence $(Xaa)_8$ was extended from the N terminal of the amino acid sequence (SEQ ID NO: 2). A library of the extended polypeptides was constructed and selection was made.

First, a library of phage, which displays a polypeptide consisting of an amino acid sequence:

(SEQ ID NO: 170)
$(Xaa)_8$-Tyr-Asp-Pro-Arg-Thr-Gly-Thr-Trp-Arg-Ser-

Ser-Ile-Ala-Tyr-Gly-Gly-Gly where Xaa represents any amino acid residue on the C terminal of coat protein g10 of T7 phage, via a linker consisting of an amino acid sequence:

(SEQ ID NO: 169)
Gly-Gly-Gly-Gly-Ser, was constructed by T7Select10-3 Cloning Kit (Novagen). Construction was performed completely in accordance with the procedure instructed by the accompanying T7Select (registered trade mark) System Manual (Novagen).

Using the phage library, the "step of bringing phages into contact with an Fc region and selecting phages bound to the region to recover the phages" was repeated six times in accordance with the procedure described in Example 1, 1) to concentrate phages displaying a polypeptide exhibiting binding activity to an Fc region. Subsequently, a molecule having binding activity was identified by ELISA from the concentrated phages in the same procedure as in Example 1, 2) and the DNA sequence was analyzed by the dideoxy method. As a result of the DNA sequence analysis, it was confirmed that amino acid sequences were converged on those represented by SEQ ID NOs: 11 to 19. Then, polypeptides containing the amino acid sequences of SEQ ID NOs: 11 to 19 were specified as the polypeptides having binding activity.

4) In this section, it will be stated as an example that the binding activity of polypeptides consisting of amino acid sequences represented by SEQ ID NOs: 2, 11, 21 and 22 (referred to as H6, 2A1, 2A1Gly and RSS, respectively) was measured by a surface plasmon resonance method.

The polypeptides previously synthesized in an organic chemical manner were purchased from bioSYNTHESIS. Biacore T100 (GE Healthcare) was used as a surface plasmon resonance measurement apparatus. The human Fc region manufactured by Jackson ImmunoResearch Laboratories, Inc. was immobilized to Sensor Chip CM5 (GE Healthcare) in accordance with an amine coupling method using an Amine Coupling Kit (GE Healthcare). Subsequently, polypeptide (H6) was diluted with HBS-T buffer (10 mM HEPES, 150 mM NaCl, 0.05% Tween 20 (registered trade mark), pH 7.4) to have a concentration of 50, 25 or 12.5 μM, polypeptide (2A1) to a concentration of 100, 80, 60, 40 or 20 nM, polypeptide (2A1Gly) to a concentration of 40, 30, 20, 10 or 5 μM, and polypeptide (RSS) to a concentration of 200, 100, 50, 25 or 12.5 μM. The binding activity of these polypeptides was measured at a reaction temperature of 25° C. The measurement data were processed by Biacore TOO Evaluation Software (GE Healthcare). As a result of calculation, H6, 2A1, 2A1Gly and RSS had binding activity values of $7.9 \times 10^{-5}$ (M), $2.2 \times 10^{-8}$ (M), $2.3 \times 10^{-5}$ (M) and $1.1 \times 10^{-4}$ (M), respectively in terms of equilibrium dissociation constant $K_D$ (Table 1A).

TABLE 1A

| Poly-peptide | Sequence | $K_D$ (nM) | SEQ ID NO: |
|---|---|---|---|
| H6 | YDPRTGTWRSSIAYGGG | 79000 | 2 |
| 2A1 | GVVRGWSGYDPRTGTWRSSIAYGGG | 22 | 11 |
| 2A1Gly | GVVRGWSGGGGSGGGGRSSIAYGGG | 23000 | 21 |
| RSS | RSSIAYGGG | 110000 | 22 |

TABLE 1B

| Fusion protein | $K_D$ (nM) | SEQ ID NO: |
|---|---|---|
| H6_trx | 180 | 82 |
| 2A1_trx | 42 | 83 |
| 2A4_trx | 200 | 84 |
| 2F12_trx | 68 | 85 |

5) In this section, it is stated as an example that thioredoxin fusion proteins containing amino acid sequences represented by SEQ ID NOs: 2 and 11 to 13 were prepared and the binding activity of the proteins was measured by a surface plasmon resonance method.

DNA molecules encoding the polypeptides of amino acid sequences 2 and 11 to 13 were amplified by a polymerase chain reaction (PCR). PCR was carried out using KOD DNA polymerase (TOYOBO) under reaction conditions according to the accompanying manual. The amplified DNA molecules were each digested with EcoRI and HindIII and introduced to a site of pET-48b (Invitrogen) digested with EcoRI/HindIII. In this way, expression vectors containing DNA molecules (SEQ ID NOs: 120 to 123), which encode fusion proteins obtained by ligating the corresponding polypeptides to the C terminal of thioredoxin (hereinafter, these fusion proteins of the polypeptides identified above and thioredoxin will be referred to as H6_trx, 2A1_trx, 2A4_trx and 2F12_trx (SEQ ID NOs: 82 to 85)) were constructed. The expression vectors thus constructed were used to transform Escherichia coli BL21 (DE3) strain (Novagen). Escherichia coli BL21 (DE3) strain was sub-cultured in 200 mL of 2×YT medium and cultured while shaking until $O.D._{600}$ reached about 0.8. Expression was induced by isopropyl β-D-1-thiogalactopyranoside (IPTG) of a final concentration of 1 mM and the Escherichia coli cells were cultured at 37° C. for 12 hours. Bacterial cells were collected by centrifugation at 5000×g for 20 minutes and suspended in buffer of 20 mM Tris-HCl 500 mM NaCl pH 7.4. The bacterial cells were ultrasonically ground by Astrason Model 53000 (Wakenyaku Co., Ltd.) and an intracellular soluble fraction was centrifugally collected at 14000×g for 20 minutes. The soluble fraction was purified by metal chelate affinity chromatography using Ni Sepharose (registered trade mark) 6 Fast Flow (GE Healthcare) to prepare a desired thioredoxin fusion protein.

Subsequently, the binding activity of the thioredoxin fusion protein prepared was measured by a surface plasmon resonance method. As a measurement apparatus, Biacore T100 (GE Healthcare) was used. The Fc region manufactured by Jackson ImmunoResearch Laboratories, Inc. was immobilized to Sensor Chip CM5 (GE Healthcare) by the amine coupling method in the same procedure as in Example 1, 4). Subsequently, the thioredoxin fusion proteins (H6_trx, 2A1_trx, 2A4_trx and 2F12_trx) prepared were each diluted with a HBS-T buffer to have a concentration of 600, 500, 400, 300, 200 or 100 nM and binding activity was measured at 25° C. Data were processed by Biacore TOO Evaluation Software (GE Healthcare). The equilibrium dissociation constants $K_D$ of H6_trx, 2A1_trx, 2A4_trx and 2F12_trx calculated were $1.8 \times 10^{-7}$ (M), $4.2 \times 10^{-8}$ (M), $2.0 \times 10^{-7}$ (M) and $6.8 \times 10^{-8}$ (M), respectively (Table 1 B).

6) In this section, it will be stated as an example that the binding activity of recombinant phages transformed by nucleic acids encoding the amino acid sequences represented by SEQ ID NOs: 2 to 9 and 11 to 19 was measured by Enzyme Linked Immuno-Sorbent Assay (ELISA).

DNA molecules encoding the amino acid sequences of SEQ ID NOs: 2 to 9 and 11 to 19 were amplified by a polymerase chain reaction (PCR). PCR was carried out using KOD DNA polymerase (TOYOBO) under reaction conditions according to the accompanying manual. The amplified DNA molecules were each digested with restriction enzymes EcoRI and HindIII and ligated to 3' terminal of g10 gene on T7 phage genomic DNA. Ligation to T7 phage genomic DNA was performed by use of a sample attached to T7Select10-3 Cloning Kit (Novagen) under the reaction conditions and in accordance with the procedure described in the accompanying T7Select (registered trade mark) System Manual. Using T7 phage genomic DNA ligated, T7 phage was packaged in a test tube by T7Select Packaging Kit (Novagen) under the reaction conditions in accordance with T7Select (registered trade mark) System Manual (Novagen). Subsequently, phage plaques were formed in accordance with T7Select (registered trade mark) System Manual (Novagen). From each of the plaques, a recombinant phage displaying the polypeptide was isolated. To MICROTEST (registered trade mark) 96 (BECTON, DICKINSON AND COMPANY), a culture solution (0.2 mL) of Escherichia coli BL5403 strain cultured in LB medium until $O.D._{600}$ reached 1.0 was poured to infect with the Escherichia coli cells each of the recombinant phages isolated from plaques and allowed to stand still at 37° C. for 12 hours to proliferate phages. The culture solution (10 μL) containing these phages was diluted in 90 μL of TBS buffer (50 mM Tris-HCl, 150 mM NaCl, pH 7.4) to prepare measurement samples.

The measurement samples were poured to MEDISORP 96 well microplate (Nunc) and allowed to stand still for one hour to allow the phage to physically adsorb to the plate. After the supernatant was removed, SuperBlock (registered trade mark) T20 (TBS) Blocking Buffer (Thermo SCIENTIFIC) (150 μL) was poured to the plate and allowed to stand still for one hour to block the surface of the plate. The plate was washed three times with TBS-T buffer (50 mM Tris-HCl, 150 mM NaCl, 0.1% Tween 20 (registered trade mark), pH 7.4). To the plate, TBS-T buffer (100 μL) containing an Fc region (Jackson ImmunoResearch Laboratories, Inc.) (0.2 μg/mL) labeled with horseradish peroxidase (HRP) was added and allowed to stand still for one hour. After the plate was washed three times with TBS-T buffer, ABTS One Component HRP Microwell Substrate (BioFX) (100 μL) was poured to the plate. Binding activity was detected through a color reaction. The absorbance at 415 nm ($O.D._{415}$) was measured by a microplate absorbance reader Sunrise R (TECAN GROUP LTD.). TBS-T buffer containing no phages was used as a negative control in a control experiment.

ELISA results of the recombinant phages displaying polypeptides containing amino acid sequences represented by SEQ ID NOs: 2 to 9 and the recombinant phages displaying polypeptides containing amino acid sequences represented by SEQ ID NOs: 11 to 19 are shown in Table 2A and Table 2B, respectively. Any one of the recombinant phages exhibited significant binding activity compared to the control.

TABLE 2A

| Polypeptide sequence | O.D. 415 | SEQ ID NO: |
|---|---|---|
| YDPRTGTWRSSIAYGGG | 0.251 | 2 |
| YDPGTGTWRSYLRFGGG | 0.278 | 3 |
| YDPYTGTWRSSIWVLSG | 0.165 | 4 |
| YDPGTGTWRSWLSFNVG | 0.155 | 5 |
| YDPWTGTWRSFIWGGGG | 0.149 | 6 |
| YDPRTGTWLLYASRLLG | 0.214 | 7 |
| YDPVTGTWTSSIASWMG | 0.223 | 8 |
| YDPRTGTWRRSSLSYSG | 0.193 | 9 |
| Control | 0.08 | |

TABLE 2B

| Polypeptide sequence | O.D. 415 | SEQ ID NO: |
|---|---|---|
| GVVRQWSGYDPRTGTWRSSIAYGGG | 0.282 | 11 |
| AGSRRAHGYDPRTGTWRSSIAYGGG | 0.267 | 12 |
| ASVRSWSSYDPRTGTWRSSIAYGGG | 0.54 | 13 |
| SWRRRGSSYDPRTGTWRSSIAYGGG | 0.282 | 14 |
| TGRGRSARYDPRTGTWRSSIAYGGG | 0.396 | 15 |
| HWVNGRSGYDPRTGTWRSSIAYGGG | 0.373 | 16 |
| ERWITWSGYDPRTGTWRSSIAYGGG | 0.368 | 17 |
| GSVVRWRGYDPRIGTWRSSIAYGGG | 0.36 | 18 |
| GAVYRRSFYDPRTGTWRSSIAYRGG | 0.353 | 19 |
| Control | 0.101 | |

7) In this section, an example is described in which a polypeptide (referred to as 2A1) consisting of an amino acid sequence represented by SEQ ID NO: 11, which is one of examples of an amino acid sequence represented by SEQ ID NO: 10, was confirmed to exhibit a specific binding activity to immunoglobulin G and an Fc region having a non-native structure. In this section, as an example of the non-native structure, such as an alternatively folded state (AFS), obtained by an acid treatment, described in the above section "Best Mode for Carrying Out the Invention," a non-native structure of immunoglobulin G or an Fc region obtained by an acid treatment or a treatment with a reducing agent was used. The binding activity to the non-native structure of immunoglobulin G or an Fc region was measured and compared to the binding activity to a natural structure.

The binding activity to a non-native structure was evaluated by a surface plasmon resonance method. 2A1 was immobilized to Sensor Chip CM5 by the amine coupling method and the binding activity to human IgG molecules or Fc regions treated under the plurality of conditions described below was measured. The following measurement samples were used.

(1) human Fc region manufactured by Jackson ImmunoResearch Laboratories, Inc.;

(2) human monoclonal IgG having a natural structure (no denaturation treatment was made);

(3) an Fc region prepared from the IgG of (2) (an Fc region was prepared by digesting IgG with papain in accordance with the instruction attached to Pierce (registered trade mark) Fab Preparation Kit (Thermo SCIENTIFIC), purified by affinity chromatography using MabSelect SuRe (GE Healthcare), HiTrap DEAE anion exchange chromatography (GE Healthcare) and gel filtration chromatography using Superdex 200 (GE Healthcare));

(4) acid-denatured IgG prepared by treating IgG of (2) with an acidic buffer (20 mM sodium acetate pH 4.5) at 50° C. for 10 days;

(5) an Fc region obtained by subjecting the Fc region of (3) to a reduction treatment with 50 mM 2-mercaptoethylamine (Thermo Scientific Pierce) at 37° C. for 90 minutes, and maintained under reductive conditions in the presence of 10 mM ethylene diamine tetraacetic acid; and (6) AFS IgG prepared by treating IgG of (2) under the conditions (10 mM Gly-HCl, 150 mM NaCl, pH 2.0) under which IgG is known to take AFS.

As a result of the surface plasmon resonance test, 2A1 binds to (1) human Fc region (FIG. 1A) purchased from Jackson ImmunoResearch Laboratories, Inc. and binds to neither (2) human IgG (FIG. 1B) having a natural structure nor (3) the Fc region (FIG. 1C) derived from the human IgG of (2). In contrast, 2A1 bound to (4) acid-denatured IgG (FIG. 1D) with $K_D=2.2\times10^9$ (M), (5) an Fc region (FIG. 1E) subjected to a reduction treatment with $K_D=1.0\times10^7$ (M) and (6) AFS IgG (FIG. 1F) with $K_D=5.0\times10^{-10}$ (M). From the above results, it was demonstrated that 2A1 consisting of the amino acid sequence of SEQ ID NO: 11 does not recognize the natural structure of an Fc region but specifically recognizes a non-native structure produced under various conditions.

8) In this section, it will be stated as an example that heat inactivation resistance of a polypeptide 2A1 represented by SEQ ID NO: 11 was evaluated. Polypeptide 2A1 was synthesized in an organic chemical manner was diluted with HBS-T buffer (10 mM HEPES, 150 mM NaCl, 0.05% Tween 20 (registered trade mark), pH 7.4) so as to have a concentration of 27 µM. The diluted solution was heated at 98° C. for 15 minutes. Samples treated with heat and not treated with heat were separately diluted with HBS-T buffer so as to obtain a concentration of 100, 50, 25 or 12.5 nM and evaluated for binding activity by surface plasmon resonance.

As the surface plasmon resonance measurement apparatus, Biacore T100 (GE Healthcare) was used. The human Fc region having a non-native structure used herein was prepared by dialyzing a natural human Fc region against an acid buffer (10 mM Gly-HCl, 150 mM NaCl, pH 2.0). The non-native human Fc region was immobilized to Sensor Chip CM5 (GE Healthcare) by the amine coupling method using Amine Coupling Kit (GE Healthcare) and subjected to binding-activity measurement performed at a reaction temperature of 25° C. The measurement data were processed by Biacore TOO Evaluation Software (GE Healthcare). As a result of calculation, the samples treated with heat and not treated with heat had binding activity values of 2.0×10−8 (M) and 2.2×10−8 (M), respectively in terms of equilibrium dissociation constant KD. The total amounts of binding response of them were the same. The above results demonstrate that the binding activity of polypeptide 2A1 is not irreversibly damaged by heat treatment and suggest that polypeptide 2A1 has high resistance against heat inactivation.

Example 2

In this Example, how to specify amino acid sequences of many polypeptides exhibiting binding activity to an antibody will be first described and then examples of measuring binding activity of the following samples will be described:
polypeptides consisting of
amino acid sequences of SEQ ID NOs: 24 to 54 containing the amino acid sequence of SEQ ID NO: 23 as a common sequence,
amino acid sequences of SEQ ID NOs: 57 to 72 containing the amino acid sequence of SEQ ID NO: 56 as a common sequence, and
amino acid sequences of SEQ ID NOs: 55 and 73 to 81 which may have addition, deletion, substitution or insertion of several amino acid residues in these amino acid sequences so as not to damage the binding activity to an Fc region of IgG; or
fusion proteins containing these amino acid sequences; or
recombinant phages transformed with nucleic acids encoding these amino acid sequences.

1) Construction of Polypeptide Library and Selection of Fc Region of Human IgG

The amino acid sequence of a polypeptide exhibiting antibody binding activity was specified by a phage display method using T7 phage.

First, a phage library, which displays a polypeptide consisting of an amino acid sequence:

```
                                         (SEQ ID NO: 171)
Asp-Ala-Ala-Trp-His-Leu-Gly-Glu-Leu-Val-

Trp-Ala-Thr-Tyr-Tyr-Asp-Pro-Glu-Thr-

Gly-Thr-Trp-(Xaa)10
``` where Xaa represents any amino acid residue,
via a linker consisting of the amino acid sequence:

```
                                         (SEQ ID NO: 169)
Gly-Gly-Gly-Gly-Ser
``` on the C terminal of coat protein g10 of T7 phage, was constructed by use of T7Select10-3 Cloning Kit (Novagen). Construction was performed completely in accordance with the procedure instructed by the accompanying T7Select (registered trade mark) System Manual (Novagen).

Next, a step of bringing the T7 phage display library constructed into contact with a target, i.e., an Fc region of human IgG, and a step of selecting a phage bound to the Fc region of human IgG and recovering the phage. The Fc region was prepared, in accordance with the instruction attached to Pierce (registered trade mark) Fab Preparation Kit (Thermo SCIENTIFIC Pierce), by digesting human monoclonal antibody IgG with papain, followed by purifying by affinity chromatography using MabSelect SuRe (GE Healthcare), HiTrap DEAE anion exchange chromatography (GE Healthcare) and gel filtration chromatography using Superdex 200 (GE Healthcare). To the Fc region thus prepared, biotin was chemically bound via an amino group by use of D-Biotinoyl-ε-Amino Caproic Acid N-Hydroxysuccinimide Ester (F. Hoffmann-La Roche Ltd.) in accordance with the accompanying instruction. Subsequently, in accordance with the same procedures as in Example 1, 1) and 2), a step of bringing the library into contact with the Fc region and selecting and recovering a phage bound to the library, a step of checking a phage displaying a polypeptide having binding activity by ELISA and DNA sequence analysis by the dideoxy method were performed. As a result, the amino acid sequences represented by SEQ ID NOs: 24 to 55 were specified as a polypeptide exhibiting binding activity.

2) Construction of Polypeptide Extension Library and Selection of Fc Region of Human IgG For enhancing the function of the polypeptide having binding activity specified in Example 2, 1), the N terminal of the polypeptide having each of two types of amino acid sequences (SEQ ID NO: 26 or 27) was extended and a phage library displaying the polypeptide was constructed. Selection was made by using the library. First, a phage library displaying a polypeptide consisting of the amino acid sequence:

```
                                         (SEQ ID NO: 172)
(Xaa)10-Tyr-Asp-Pro-Glu-Thr-Gly-Thr-Trp-

Tyr-Asp-Ala-Ala-Trp-His-Leu-Gly-Glu-Leu-

Val-Trp-Ala-Thr-Tyr-Tyr-Asp-Pro-Glu-

Thr-Gly-Thr-Trp-Leu-Pro-Asp-Trp-Gln-Thr-

Met-Ala-Gln-Lys, or,
                                         (SEQ ID NO: 173)
(Xaa)10-Tyr-Asp-Pro-Glu-Thr-Gly-Thr-Trp-

Tyr-Asp-Ala-Ala-Trp-His-Leu-Gly-Glu-Leu-Val-

Trp-Ala-Thr-Tyr-Tyr-Asp-Pro-Glu-Thr-Gly-

Thr-Trp-Glu-Pro-Asp-Trp-Gln-Arg-Met-

Leu-Gly-Gln
``` where Xaa represents any amino acid residue,
on the C terminal of the coat protein g10 of T7 phage via a linker consisting of the amino acid sequence:

```
                                         (SEQ ID NO: 169)
        Gly-Gly-Gly-Gly-Ser
``` was constructed by use of T7Select1-1 Cloning Kit (Novagen). Construction was performed completely in accordance with the procedure instructed by the accompanying T7Select (registered trade mark) System Manual (Novagen).

The "step of bringing a library into contact with an Fc region and selecting and recovering a phage bound to the Fc region" was carried out by using the phage library constructed in the same manner as in Example 2, 1) and repeated 10 times. The binding activity test by ELISA and DNA sequence analysis were performed in the same manner as in Example 1, 2). As a result, the amino acid sequences represented by SEQ ID NOs: 57 to 81 were specified as a polypeptide having binding activity.

3) In this section, it will be stated as an example that the binding activity of polypeptides consisting of amino acid sequences of SEQ ID NOs: 24 to 27 (referred to as pep14, pep11, pep21 and pep24, respectively) was measured by surface plasmon resonance. The polypeptides, which were previously synthesized in an organic chemical manner were purchased from bioSYNTHESIS, were diluted with HBS-T buffer and controlled so as to have a concentration of 500, 400, 300, 200 or 100 nM. The surface plasmon resonance test was performed by using Biacore T100 (GE Healthcare).

The Fc region to be immobilized to a sensor chip was prepared, by digesting human monoclonal antibody IgG with papain, in accordance with the instruction attached to Pierce (registered trade mark) Fab Preparation Kit (Thermo SCIENTIFIC), followed by purifying by affinity chromatography using MabSelect SuRe (GE Healthcare), HiTrap DEAE anion exchange chromatography (GE Healthcare) and gel filtration chromatography using Superdex 200 (GE Healthcare). The Fc region prepared was immobilized to Sensor Chip CM5 (GE Healthcare) by the amine coupling method. The binding activity of the synthesized peptides prepared was measured and equilibrium dissociation constants were determined. Data were processed by use of Biacore T00 Evaluation Software (GE Healthcare). The equilibrium dissociation constants $K_D$ of pep14, pep11, pep21 and pep24 calculated were $1.2\times10^{-7}$ (M), $5.1\times10^{-7}$ (M), $1.0\times10^{-7}$ (M) and $2.2\times10^{-7}$ (M), respectively (Table 3A).

TABLE 3A

| Polypeptide | Sequence | KD (nM) | SEQ ID NO: |
|---|---|---|---|
| pep14, | DAAWHLGELVWATYYDPETGTWQPDWLYMTTR | 120 | 24 |
| pep11 | DAAWHLGELVWATYYDPETGTWAPDWRLMQGQ | 510 | 25 |
| pop21 | DAWHLGELVWATYYDPETGTWLPDWQTMAQK | 100 | 26 |
| pep24 | DAAWHLGELVWATYYDPETGTWEPDWQRMLGQ | 220 | 27 |

4) In this section, it will be stated as an example that the binding activity of a polypeptide consisting of an amino acid sequence (referred to as p17) of SEQ ID NO: 57 was measured by surface plasmon resonance. The polypeptide was prepared by cleaving thioredoxin fusion protein p17_trx consisting of the amino acid sequence of SEQ ID NO: 86 with a protease and removing a thioredoxin portion. Since the thioredoxin fusion protein, which is produced by expression vector pET-48b (Novagen), has an HRV 3C protease cleavage site in the amino acid sequence, the desired polypeptide ligated to the C terminal can be obtained by use of protease.

DNA (SEQ ID NO: 124) encoding the thioredoxin fusion protein (SEQ ID NO: 86) containing p17 was synthesized by PCR and introduced to an expression vector, pET-48b (Novagen). Using the expression vector and in accordance with the same procedure as in Example, 1, 5), the thioredoxin fusion protein was prepared. The thioredoxin fusion protein (40 mg) was digested with 100 units of HRV 3C Protease (Novagen) at 4° C. under the reaction conditions according to the accompanying manual. The digested product was diluted in a 6 M guanidine hydrochloride solution and purified by gel filtration chromatography using Superdex Peptide 10/300 GL (GE Healthcare). Subsequently reverse phase chromatography using µRPC C2/C18 ST 4.6/100 (GE Healthcare) was performed to prepare a polypeptide p17 consisting of an amino acid sequence of SEQ ID NO: 57.

Subsequently, the binding activity of p17 prepared was measured by surface plasmon resonance by use of Biacore T100 (GE Healthcare). Polypeptide p17 was diluted in HBS-T and controlled to have a concentration of 25, 12.5, 6.25 or 3.13 nM. The Fc region was immobilized to Sensor Chip CM5 and measurement of binding activity was performed in the same procedure as in Examples 2, 3). As a result of analysis, p17 bound to the Fc region with an equilibrium dissociation constant $K_D$ of $1.6\times10^{-9}$ (M) (Table 3B).

TABLE 3B

| Polypeptide | Sequence | KD (nM) | SEQ ID NO: |
|---|---|---|---|
| p17 | GPGISAFSPGRGVYDPETGTWYDAAWHLGELVWATYYDPETGTWEPDWQRMLGQ | 1.6 | 57 |

This value exhibits extremely high binding activity as the binding activity of a linear polypeptide. The binding activity values of IgG-binding proteins, protein A and protein G, conventionally used, more specifically, the binding activity value of their domains by themselves, in terms of $K_D$ are at most about $1.0\times10^{-8}$ (M) (Non Patent Literature 28) and $4.9\times10^{-7}$ (M) (Non Patent Literature 29), respectively. Even compared to that of a cyclic polypeptide whose binding activity is generally higher than that of linear polypeptide, the polypeptide p17 of the present invention has a high binding activity of the highest rank beyond the value of cyclic peptide FcBP-2 ($K_D$=2.2 nM) (Non Patent Literature 4) reported to have a high binding activity.

5) In this section, it will be stated as an example that thioredoxin fusion proteins containing amino acid sequences represented by SEQ ID NOs: 24, 26 to 33 and 57 to 81 were prepared and the binding activity of them was measured by a surface plasmon resonance method.

DNA molecules encoding polypeptides of SEQ ID NOs: 24, 26 to 33 and 57 to 81 were amplified by PCR, digested with EcoRI and HindIII and each introduced to a site of pET-48b (Invitrogen) digested with EcoRI/HindIII to construct expression vectors containing DNA (SEQ ID NOs: 125 to 133, 124, 136, 137, 139, 140, 144 to 151, 154 to 156, 134, 135, 138, 141 to 143, 152, 153 and 157) encoding fusion proteins (SEQ ID NOs: 87 to 95, 86, 98, 99, 101, 102, 106 to 113, 116 to 118, 96, 97, 100, 103 to 105, 114, 115 and 119) obtained by ligating a polypeptide to the C terminal of thioredoxin. Using the expression vectors, thioredoxin fusion proteins were prepared in the same manner as in Example 1, 5).

Subsequently, the binding activity of the prepared thioredoxin fusion proteins was measured by a surface plasmon resonance method. As the measurement apparatus, Biacore T100 (GE Healthcare) was used. An Fc region was immobilized to Sensor Chip CM5 (GE Healthcare) by the amine coupling method in the same manner as in Example 2, 3). Subsequently, the prepared thioredoxin fusion proteins each were diluted with HBS-T buffer and controlled so as to have a concentration of 600, 500, 400, 300, 200 or 100 nM. The binding activity was measured at 25° C. Data were processed by Biacore T00 Evaluation Software (GE Healthcare). The values $K_D$ calculated are shown in Table 4.

TABLE 4A

| Sequence of polypeptide fused with thioredoxin | $K_D$ (nM) | SEQ ID NO: (polypeptide) | SEQ ID NO: (fusion protein) |
|---|---|---|---|
| DAAWHLGELVWATYYDPETGTWQPDWLYMTTR | 720 | 24 | 87 |
| DAAWHLGELVWATYYDPETGTWLPDWQTMAQK | 26 | 26 | 88 |
| DAAWHLGELVWATYYDPETGTWEPDWQRMLGQ | 120 | 27 | 89 |
| DAAWHLGELVWATYYDPETGTWQPDWRAMSGR | 200 | 28 | 90 |
| DAAWHLGELVWATYYDPETGTWRPDWKWMSTH | 850 | 29 | 91 |
| DAAWHLGELVWATYYDPETGTWEPDWKLMQRP | 640 | 30 | 92 |
| DAAWHLGELVWATYYDPETGTWQPDWDIMAGH | 130 | 31 | 93 |
| DAAWHLGELVWATYYDPETGTWLPDWDVMVRQ | 63 | 32 | 94 |
| DAAWHLGELVWATYYDPETGTWVPDWERMEQH | 3270 | 33 | 95 |
| GPGISAFSPGRGVYDPETGTWYDAAWHLGELVWATYYDPETGTWEPDWQRMLGQ | 7.8 | 57 | 86 |
| VISLGSDRGVYDPETGTWYDAAWHLGELVWATYYDPETGTWEPDWQRMLGQ | 32 | 58 | 98 |
| IMSVDGSSARYDPETGTWYDAAWHLGELVWATYYDPETGTWEPDWQRMLGQ | 34 | 59 | 99 |
| VDLRAHGGAVYDPETGTWYDAAWHLGELVWATYYDPETGTWEPDWQRMLGQ | 50 | 60 | 101 |
| WSRFSSRSVAYDPETGTWYDAAWHLGELVWATYYDPETGTWEPDWQRMLGQ | 39 | 61 | 102 |
| GNPSDSASAWYDPETGTWYDAAWHLGELVWATYYDPETGTWEPDWQRMLGQ | 26 | 62 | 106 |
| SNFVRSPSAWYDPETGTWYDAAWHLGELVWATYYDPETGTWEPDWQRMLGQ | 24 | 63 | 107 |
| IPYGFPGRGEYDPETGTWYDAAWHLGELVWATYYDPETGTWEPDWQRMLGQ | 14 | 64 | 108 |

TABLE 4B

| Sequence of polypeptide fused with thioredoxin | $K_D$ (nM) | SEQ ID NO: (polypeptide) | SEQ ID NO: (fusion protein) |
|---|---|---|---|
| GPYNIPDSAVYDPETGTWYDAAWHLGELVWATYYDPETGTWEPDWQRMLGQ | 14 | 65 | 109 |
| WPLNAPSSAFYDPETGTWYDAAWHLGELVWATYYDPETGTWEPDWQRMLGQ | 25 | 66 | 110 |
| VPPRFSSSAQYDPETGTWYDAAWHLGELVWATYYDPETGTWEPDWQRMLGQ | 8.8 | 67 | 111 |
| FLVGLHAGAVYDPETGTWYDAAWHLGELVWATYYDPETGTWEPDWQRMLGQ | 32 | 68 | 112 |
| VVRVDHSSAVYDPETGTWYDAAWHLGELVWATYYDPETGTWEPDWQRMLGQ | 30 | 69 | 113 |
| WMEFYPGRGVYDPETGTWYDAAWHLGELVWATYYDPETGTWEPDWQRMLGQ | 11 | 70 | 116 |
| DGVGPGSRGVYDPETGTWYDAAWHLGELVWATYYDPETGTWEPDWQRMLGQ | 23 | 71 | 117 |
| FVSSLPNSAMYDPETGTWYDAAWHLGELVWATYYDPETGTWEPDWQRMLGQ | 17 | 72 | 118 |
| GRAFSGSRRWYDPETGTWYDAAWHLGELVWATYYDPETGTWAPDWRLMQGQ | 39 | 73 | 96 |

TABLE 4B-continued

| Sequence of polypeptide fused with thioredoxin | K_D (nM) | SEQ ID NO: (polypeptide) | SEQ ID NO: (fusion protein) |
|---|---|---|---|
| VMATEVVRGVYDPETGTWYDATWHLGELVWATYYDPETGTWE PDWQRMLGQ | 110 | 74 | 97 |
| MMVRPPRLGVYDPEPGTWYDATWHLGELVWATYYDPETGTWE PDWQRMLGQ | 85 | 75 | 100 |
| ERHLVSDYLHYDPETGTWYDAAWHLGELVWATYYDPETGTWE PDWQRMLGQ | 27 | 76 | 103 |
| FSDLDSFGVSYDPETGTWYDAAWHLGELVWATYYDPETGTWE PDWQRMLGQ | 240 | 77 | 104 |
| LEDNKLKHASYDPETGTWYDAAWHLGELVWATYYDPETGTWE PDWQRMLGQ | 44 | 78 | 105 |
| GSCKFSSSCHYDPETGTWYDAAWHLGELVWATYYDPETGTWE PDWQRMLGQ | 35 | 79 | 114 |
| LIPPGGISPWYDPETGTWYDAAWHLGELVWATYYDPETGTWE PDWQRMLGQ | 38 | 80 | 115 |
| LNDFLTPTAWYDPETGTWYDAAWHLGELVWATYYDPETGTWL PDWQTMAQK | 14 | 81 | 119 |

6) In this section, it will be stated as an example that the binding activity of recombinant phages transformed by nucleic acids encoding amino acid sequences represented by SEQ ID NOs: 26, 27, 30 to 55, 57, 63 to 72 and 79 to 81 was measured by Enzyme Linked Immuno-Sorbent Assay (ELISA).

DNA molecules encoding amino acid sequences of SEQ ID NOs: 26, 27, 30 to 55, 57, 63 to 72 and 79 to 81 were amplified by a polymerase chain reaction (PCR) using KOD DNA polymerase (TOYOBO) under the reaction conditions according to the accompanying manual. Each of the amplified DNA was digested with restriction enzymes EcoRI and HindIII, and ligated to the 3' terminal of g10 gene on T7 phage genomic DNA. Ligation to T7 phage genomic DNA was performed by use of a sample attached to T7Select10-3 Cloning Kit (Novagen) under the reaction conditions and in accordance with the procedure described in T7Select (registered trade mark) System Manual. Using T7 phage genomic DNA ligated, T7 phage was packaged in a test tube by T7Select Packaging Kit (Novagen) under the reaction conditions in accordance with T7Select (registered trade mark) System Manual (Novagen). Subsequently, phage plaque was formed in accordance with T7Select (registered trade mark) System Manual (Novagen). From each of the plaques, a recombinant phage displaying the polypeptide was isolated. To MICROTEST (registered trade mark) 96 (BECTON, DICKINSON AND COMPANY), a culture solution (0.2 mL) of *Escherichia coli* BL5403 strain cultured in LB medium until O.D._{600} reached 1.0 was poured to infect with the *Escherichia coli* cells each of the recombinant phages isolated from plaques and allowed to stand still 37° C. for 12 hours to proliferate phages. The culture solution (10 μL) containing these phages was diluted in 90 μL of TBS buffer (50 mM Tris-HCl, 150 mM NaCl, pH 7.4) to prepare measurement samples.

The measurement samples were poured to MEDISORP 96 well microplate (Nunc) and allowed to stand still for one hour to allow the phage to physically adsorb to the plate. The supernatant was removed and SuperBlock (registered trade mark) T20 (TBS) Blocking Buffer (Thermo SCIENTIFIC) (150 μL) was poured to the plate and allowed to stand still for one hour to block the surface of the plate. The plate was washed three times with TBS-T buffer (50 mM Tris-HCl, 150 mM NaCl, 0.1% Tween 20 (registered trade mark), pH 7.4). To the plate, TBS-T buffer (100 μL) containing an Fc region (Jackson ImmunoResearch Laboratories, Inc.) (0.2 μg/mL) labeled with horseradish peroxidase (HRP) was added and allowed to stand still for one hour. After the plate was washed three times with TBS-T buffer, ABTS One Component HRP Microwell Substrate (BioFX) (100 μL) was poured to the plate. The binding activity was detected through a light-emitting reaction. The absorbance at 415 nm (O.D._{415}) was measured by a microplate absorbance reader Sunrise R (TECAN GROUP LTD.). TBS-T buffer containing no phages was used as a negative control in a control experiment.

ELISA results of the recombinant phages displaying polypeptides containing amino acid sequences represented by SEQ ID NOs: 26, 27 and 30 to 55 and the recombinant phages displaying polypeptides containing amino acid sequences represented by SEQ ID NOs: 57, 63 to 72 and 79 to 81 are shown in Table 5A and Table 5B, respectively. Any one of recombinant phages exhibited significant binding activity compared to the control.

TABLE 5A

| Polypeptide sequence | O.D. 415 | SEQ ID NO: |
|---|---|---|
| DAAWHLGELVWATYYDPETGTWLPDWQTMAQK | 0.43 | 26 |
| DAAWHLGELVWATYYDPETGTWEPDWQRMLGQ | 0.289 | 27 |
| DAAWHLGELVWATYYDPETGTWEPDWKLMQRP | 0.287 | 30 |

TABLE 5A-continued

| Polypeptide sequence | O.D. 415 | SEQ ID NO: |
|---|---|---|
| DAAWHLGELVWATYYDPETGTWQPDWDIMAGH | 0.295 | 31 |
| DAAWHLGELVWATYYDPETGTWLPDWDVMVRQ | 0.352 | 32 |
| DAAWHLGELVWATYYDPETGTWVPDWERMKQH | 0.305 | 33 |
| DAAWHLGELVWATYYDPETGTWEPDWSKMRPQ | 0.281 | 34 |
| DAAWHLGELVWATYYDPETGTWRPDWAVMATP | 0.32 | 35 |
| DAAWHLGELVWATYYDPETGTWKPDWRMMGVP | 0.287 | 36 |
| DAAWHLGELVWATYYDPETGTWLPDWDYMSSK | 0.235 | 37 |
| DAAWHLGELVWATYYDPETGTWMPDWDRMLRR | 0.29 | 38 |
| DAAWHLGELVWATYYDPETGTWTPDWNAMSQR | 0.273 | 39 |
| DAAWHLGELVWATYYDPETGTWQPDWKRMTSR | 0.251 | 40 |
| DAAWHLGELVWATYYDPETGTWQPDWGRMNSK | 0.274 | 41 |
| DAAWHLGELVWATYYDPETGTWAPDWNRMRDFNRSFREV | 0.273 | 42 |
| DAAWHLGELVWATYYDPETGTWVPDWDAMSSR | 0.813 | 43 |
| DAAWHLGELVWATYYDPETGTWIPDWTRMQTW | 0.243 | 44 |
| DAAWHLGELVWATYYDPETGTWKPDWQRMKLH | 0.249 | 45 |
| DAAWHLGELVWATYYDPETGTWLPDWSQMRPQ | 0.243 | 46 |
| DAAWHLGELVWATYYDPETGTWLPDWDTMTPR | 0.255 | 47 |
| DAAWHLGELVWATYYDPETGTWQPDWSVMKSL | 0.373 | 48 |
| DAAWHLGELVWATYYDPETGTWVPDWDTMHAAINRSFREV | 0.346 | 49 |
| DAAWHLGELVWATYYDPETGTWIPDWRAMSQF | 0.244 | 50 |
| DAAWHLGELVWATYYDPETGTWLPDWNLMGQH | 0.265 | 51 |
| DAAWHLGELVWATYYDPETGTWRPDWARMEPM | 0.25 | 52 |
| DAAWHLGELVWATYYDPETGTWKPDWQVMSPVSNRSFREV | 0.279 | 53 |
| DAAWHLGELVWATYYDPETGTWQPDWEIMRPF | 0.258 | 54 |
| EAWHLGELVWATYYDPETGTWRPDWSRMSGR | 0.252 | 55 |
| Control | 0.11 | |

TABLE 5B

| Polypeptide sequence | O.D. 415 | SEQ ID NO: |
|---|---|---|
| GPGISAFSPGRGVYDPETGTWYDAAWHLGELVWATYYDPETGTWEPDWQRMLGQ | 0.229 | 57 |
| SNFVRSPSAWYDPETGTWYDAAWHLGELVWATYYDPETGTWEPDWQRMLGQ | 0.272 | 63 |
| IPYGFPGRGEYDPETGTWYDAAWHLGELVWATYYDPETGTWEPDWQRMLGQ | 0.213 | 64 |
| GPYNIPDSAVYDPETGTWYDAAWHLGELVWATYYDPETGTWEPDWQRMLGQ | 0.291 | 65 |
| WPLNAPSSAFYDPETGTWYDAAWHLGELVWATYYDPETGTWEPDWQRMLGQ | 0.182 | 66 |
| VPPRFSSSAQYDPETGTWYDAAWHLGELVWATYYDPETGTWEPDWQRMLGQ | 0.25 | 67 |
| FLVGLHAGAVYDPETGTWYDAAWHLGELVWATYYDPETGTWEPDWQRMLGQ | 0.186 | 68 |
| VVRVDHSSAVYDPETGTWYDAAWHLGELVWATYYDPETGTWEPDWQRMLGQ | 0.201 | 69 |
| WMEFYPGRGVYDPETGTWYDAAWHLGELVWATYYDPETGTWEPDWQRMLGQ | 0.189 | 70 |
| DGVGPGSRGVYDPETGTWYDAAWHLGELVWATYYDPETGTWEPDWQRMLGQ | 0.219 | 71 |

TABLE 5B-continued

| Polypeptide sequence | O.D. 415 | SEQ ID NO: |
|---|---|---|
| FVSSLPNSAMYDPETGTWYDAAWHLGELVWATYYDPETGTWEPDWQRMLGQ | 0.229 | 72 |
| GSCKFSSSCHYDPETGTWYDAAWHLGELVWATYYDPETGTWEPDWQRMLGQ | 0.329 | 79 |
| LIPPGGISPWYDPETGTWYDAAWHLGELVWATYYDPETGTWEPDWQRMLGQ | 0.215 | 80 |
| LNDFLTPTAWYDPETGTWYDAAWHLGELVWATYYDPETGTWLPDWQTMACK | 0.235 | 81 |
| Control | 0.098 | |

Example 3

In this Example, it will be stated as an example that non-nativenon-native IgG contained in a small amount in a natural IgG sample was quantitatively detected by using synthetic peptide 2A1 represented by SEQ ID NO: 11. Generally in a quality control step of antibody drugs, chromatographic technique such as size exclusion chromatography is frequently used as a rapid and simple technique for evaluating heterogeneity (Non Patent Literature 30). In the Example, usefulness of a detection technique using the polypeptide of the present invention was demonstrated by comparing to general method, i.e., size exclusion chromatography.

Non-nativeNon-native IgG was obtained by dialyzing a human monoclonal antibody against 10 mM Glycine-HCl, 150 mM NaCl, pH 2.0 by which AFS is known to be produced, for 18 hours. The prepared non-nativenon-native IgG was neutralized by Tris-HCl (pH 8.0) and mixed with natural IgG (6.7 µM) diluted in HBS-T buffer at predetermined dilution rates (10, 5, 1, 0.1, 0.01, 0.001%), which were used as measurement samples.

Subsequently, measurement samples were analyzed by use of surface plasmon resonance and size exclusion chromatography. Both analysis methods were compared with respect to detection sensitivity of non-nativenon-native IgG. The surface plasmon resonance test was performed by use of the measurement apparatus and sensor chip described in Example 1, 7).

Figure 2:
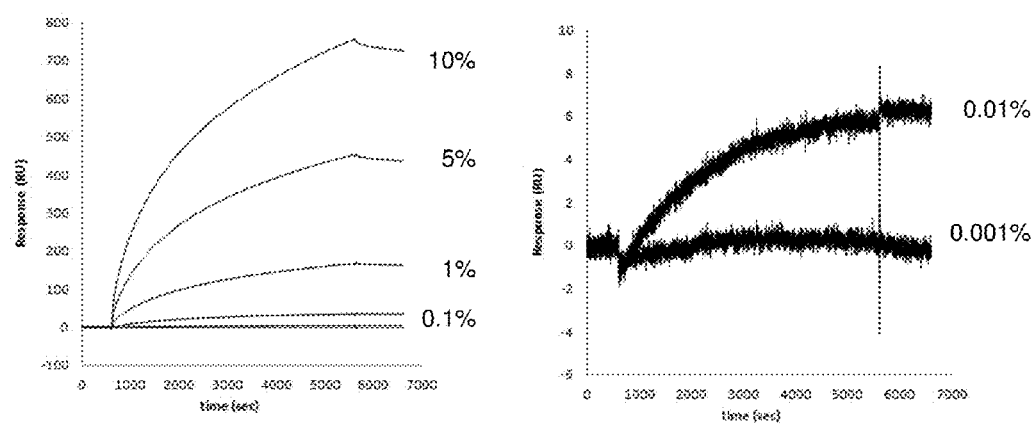
FIG. 2 shows detection results of contaminant, AFS IgG by surface plasmon resonance; more specifically, shows binding curves exhibited by samples prepared by adding a contaminant, AFS IgG in ratios of 10, 5, 1, 0.1, 0.01 and 0.001% to natural IgG of 6.7 μM in concentration.
Figure 3:
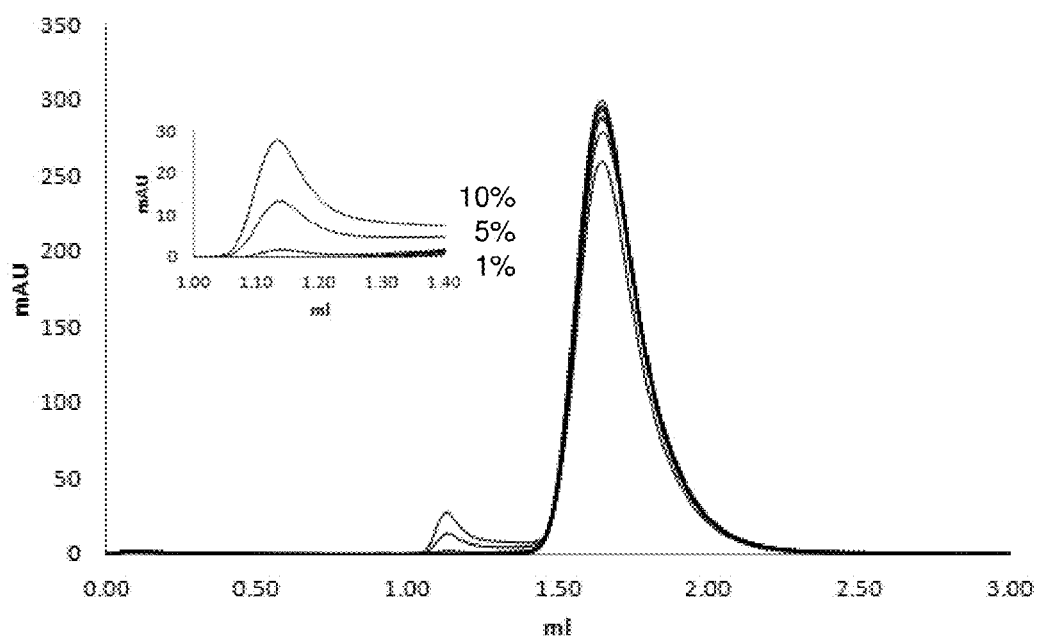
FIG. 3 shows detection results of contaminant, AFS IgG by size exclusion chromatography; more specifically, shows chromatograms of samples prepared by adding a contaminant, AFS IgG in ratios of 10, 5, 1, 0.1, 0.01 and 0.001% to natural IgG of 6.7 M in concentration. The figure inserted therein is a magnified view of a multimer fraction.

Measurement data of prepared samples were analyzed by Bicore T100 Evaluation Software (GE Healthcare), an amount of contaminant, i.e., non-native IgG, was determined as a binding response (FIG. 2). The size exclusion chromatography was performed by using an AKTA purifier (GE Healthcare) as an analysis apparatus and Superdex 200 5/150 GL (GE Healthcare) as a column. Measurement data were processed by UNICORN version 4.12 (GE Healthcare). Based on the areas of the peaks of an IgG monomer fraction and a multimer fraction detected (FIG. 3), the amount of contaminant, i.e., non-native IgG, was determined.

Figure 4:
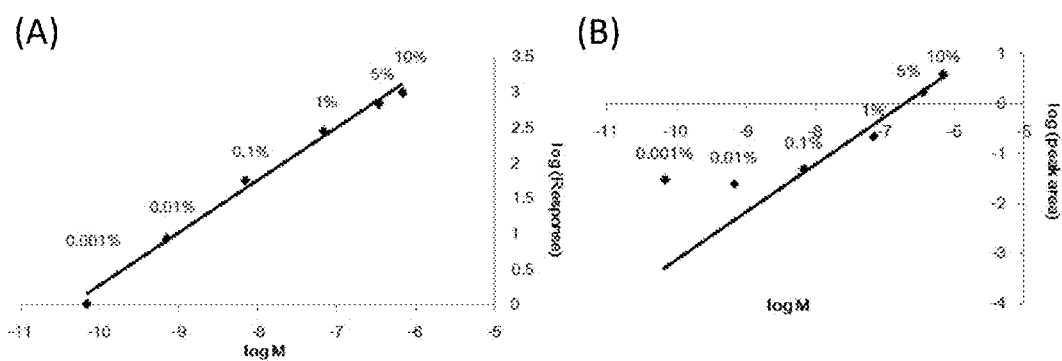
FIG. 4 (A) shows the results showing a detection range of AFS IgG obtained by surface plasmon resonance; more specifically, shows a double logarithmic chart obtained by plotting the binding response obtained from the results of FIG. 2 and the concentration of contaminant, AFS IgG; and (B) shows the results showing a detection range of AFS IgG obtained by size exclusion chromatography; more specifically, shows a double logarithmic chart obtained by plotting the ratio of a multimer fraction, which is calculated from the peak areas of the multimer fraction of IgG obtained from the chromatograms of FIG. 3 and the monomer fraction, and the concentration of contaminant, AFS IgG.

FIG. 4 shows double logarithmic charts prepared by plotting amounts of AFS IgG detected by surface plasmon resonance method and size exclusive chromatography each relative to the concentration of AFS IgG, in comparison. In the size exclusion chromatography, the detection sensitivity is significant since a contamination rate reaches up to 0.1%. In the contamination detection using surface plasmon resonance and the polypeptide of the present invention, non-native IgG can be highly sensitively detected owing to the high binding activity of the polypeptide; more specifically, it was found that the sensitivity is sufficient to detect a contamination rate of even 0.01%. In short, the results of the Example demonstrate that an extremely small amount of non-native IgG mixed in natural IgG such as an antibody drug can be accurately detected by use of a non-native IgG-binding polypeptide, compared to conventional methods.

Example 4

In this Example, it will be stated as an example that an affinity column was prepared by immobilizing thioredoxin fusion protein p17_trx (SEQ ID NO: 86) prepared by fusing an IgG-binding polypeptide, and the affinity column was used in removing and purifying an Fc region and in purifying human IgG. As described in Example 2, 4), the polypeptide of the present invention binds to an Fc region of IgG with an equilibrium dissociation constant of the order of nM and thus has a binding activity corresponding to those of a conventional IgG-binding protein and IgG-binding polypeptide or beyond them. Based on the high binding activity, the polypeptide of the present invention was applied to an affinity column, which can be favorably used for selectively removing an Fc region or IgG purification.

(1) In this section, it will be stated as an example that the polypeptide of the present invention was applied to a case where removal of an Fc region is required, more specifically, a case where a Fab region was purified from papain digestion product of IgG. A thioredoxin fusion protein was prepared in the same manner as in Example 2, 5). Thioredoxin fusion protein p17_trx (12 mg/mL) prepared was immobilized to HiTrap NHS-activated HP (GE Healthcare) via an amino group under the conditions and a method according to the accompanying manual. The amount of immobilized fusion protein calculated was about 10.8 mg.

Figure 5:
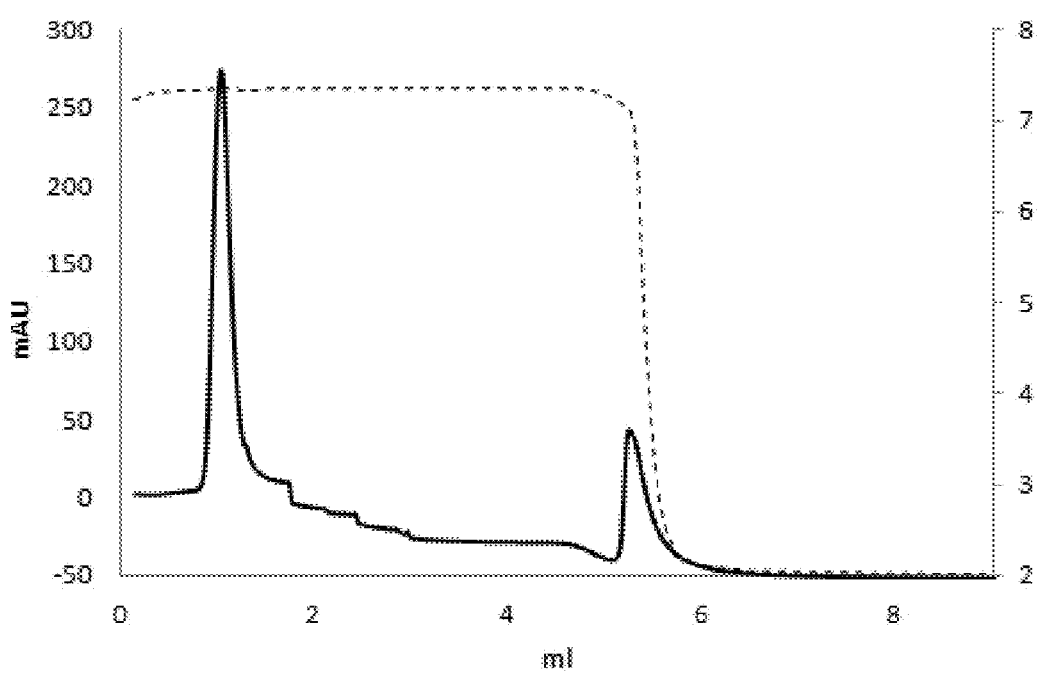
FIG. 5 shows the purification results obtained by affinity chromatography using p17_trx immobilization column, in which a continuous line indicates a chromatogram obtained when a papain digestion product of human monoclonal IgG is applied to the column and a broken line indicates pH of the buffer. The peak in the early part corresponds to a flow-through fraction; whereas the peak of the later part corresponds to an elution fraction with an acid buffer.
Figure 6:
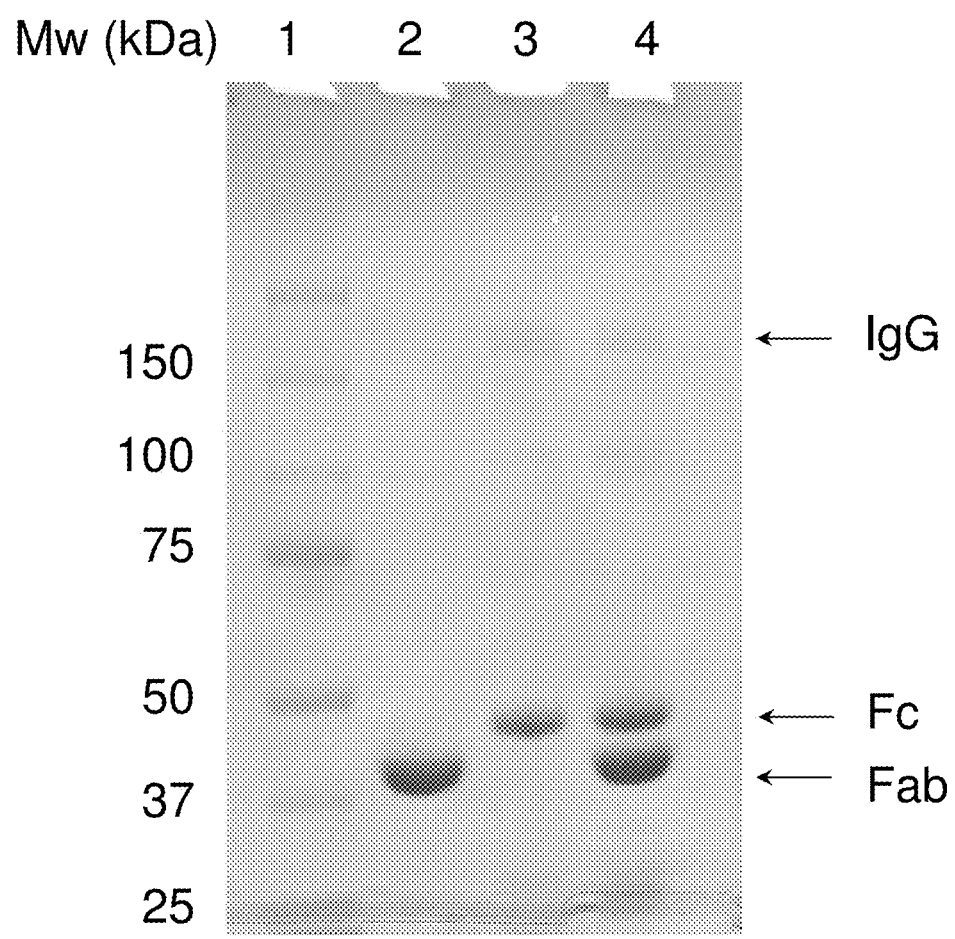
FIG. 6 shows SDS-polyacrylamide gel electrophoretogram of a sample fractionated by affinity chromatography using p17_trx immobilization column, for confirming a degree of purification of the sample, in which electrophoresis results of a molecular weight marker is shown in lane 1, a flow-through fraction in the chromatogram of FIG. 5 in lane 2, an elution fraction in lane 3 and a sample before applied to the column in lane 4.

Subsequently, human monoclonal IgG was digested with papain by use of Pierce Fab Preparation Kit (Thermo SCIENTIFIC) in accordance with the accompanying manual. The papain digestion product of IgG prepared was purified by p17_trx immobilization column. More specifically, to AKTA purifier (GE Healthcare) used as a chromatographic apparatus, a papain digestion product was applied in the presence of a running buffer (50 mM Tris-HCl, 150 mM NaCl, pH 7.4) and elution was made by an elution buffer (100 mM Gly-HCl, pH 2.0). The obtained chromatogram is shown in FIG. 5. A flow-through fraction represented by the peak in the early part and an elution fraction represented by the peak of the later part were checked by SDS-polyacrylamide gel electrophoresis (FIG. 6). As a result, it was found that Fab, an Fc region and unreacted IgG are completely separated by application of p17_trx immobilization column. In short, this Example demonstrates that affinity chromatography using an IgG-binding polypeptide according to the present invention can be favorably used for selectively removing an Fc region.

Figure 7:
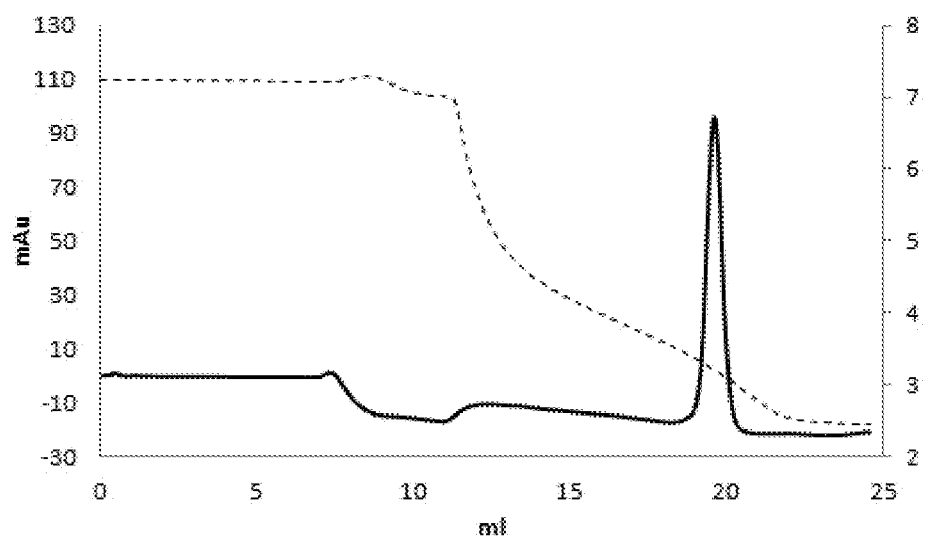
FIG. 7 shows the purification results of human IgG by affinity chromatography using p17_trx immobilization column, in which a continuous line indicates a chromatogram obtained by applying human monoclonal IgG to the column and eluting by pH gradient and a broken line indicates pH of the buffer.

(2) In this section, it will be stated as an example that p17_trx immobilization column was applied to purification of human monoclonal IgG. To the column prepared in the previous section, human monoclonal IgG was applied in the presence of a running buffer (50 mM Tris-HCl, 150 mM NaCl, pH 7.4) and IgG was eluted by pH gradient prepared by mixing 50 mM sodium citrate (pH 7.0) and 0.5 M acetic acid (pH 2.5). The obtained chromatogram is shown in FIG. 7. The IgG applied was trapped with the column and was able to be eluted under an acidic condition of pH about 3.25. This result demonstrates that the IgG-binding polypeptide of the present invention can be favorably used in an affinity column that can be used for IgG purification.

Example 5

In this section, it will be stated as an example that the binding activity of variants (SEQ ID NOs: 158 to 164), which were obtained by introducing a mutation of 1 amino acid residue to the amino acid sequence of polypeptide 2A1 represented by SEQ ID NO: 11, was measured by surface plasmon resonance to evaluate the effect of each amino acid residue on binding.

Seven types of variant polypeptides, 2A1_Q5R (SEQ ID NO: 158), 2A1_W6A (SEQ ID NO: 159), 2A1_S7A (SEQ ID NO: 160), 2A1_R17A (SEQ ID NO: 161), 2A1_S18A (SEQ ID NO: 162), 2A1_S19A (SEQ ID NO: 163) and 2A_I20A (SEQ ID NO: 164) previously synthesized in an organic chemical manner, were purchased from bioSYN-THESIS. As the surface plasmon resonance measurement apparatus, Biacore T100 (GE Healthcare) was used. The human Fc region having a non-native structure used herein was prepared by dialyzing a natural human Fc region against an acid buffer (10 mM Gly-HCl, 150 mM NaCl, pH 2.0). The non-native human Fc region was immobilized to Sensor Chip CM5 (GE Healthcare) by the amine coupling method using Amine Coupling Kit (GE Healthcare). Subsequently, polypeptide Q5R was diluted with HBS-T buffer (10 mM HEPES, 150 mM NaCl, 0.05% Tween 20 (registered trade mark), pH 7.4) to have a concentration of 62.5, 31.3 or 15.6 nM, W6A to a concentration of 500, 250 or 125 nM; S7A a concentration of 1000, 500 or 250 nM, R17A to a concentration of 500, 250 or 125 nM, S18A to a concentration of 125, 62.5 or 31.3 nM, S19A to a concentration of 1000, 500 or 250 nM and I20A to a concentration of 500, 250 or 125 nM. The binding activity was measured at a reaction temperature of 25° C.

Measurement data were processed by Biacore T00 Evaluation Software (GE Healthcare) to calculate equilibrium dissociation constant $K_D$ values of Q5R, W6A, S7A, R17A, S18A, S19A and I20A (Table 6). As a result, it was found that binding activity increases 2.5 times by changing the glutamine residue at the 5-position to an arginine residue. Furthermore, the amino acid residues which significantly reduce binding activity by changing each of them to an alanine residue were identified. It was confirmed that a tryptophan residue at the 6-position reduces the binding activity about 1/8; the serine residue at the 7-position about 1/5, the arginine residue at the 17-position about 1/16, the serine residue at the 19-position about 1/10 and the isoleucine residue at the 20-position about 1/50. The results show that these residues are greatly involved in expression of binding activity.

TABLE 6

| Polypeptide | Sequence | $K_D$ (nM) | SEQ ID NO: |
|---|---|---|---|
| 2A1_Q5R | GVVRRWSGYDPRTGTWRSSIAYGGG | 8.7 | 158 |
| 2A1_W6A | GVVRQASGYDPRTGTWRSSIAYGGG | 180 | 159 |
| 2A1_S7A | GVVRQWAGYDPRTGTWRSSIAYGGG | 110 | 160 |
| 2A1_R17A | GVVRQWSGYDPRTGTWASSIAYGGG | 350 | 161 |
| 2A1_S18A | GVVRQWSGYDPRTGTWRASIAYGGG | 23 | 162 |
| 2A1_S19A | GVVRQWSGYDPRTGTWRSAIAYGGG | 220 | 163 |
| 2A1_I20A | GVVRQWSGYDPRTGTWRSSAAYGGG | 920 | 164 |

Example 6

In this Example, it will be stated as an example that a target Fc region of human IgG was recovered from a solution containing contaminant proteins in order to evaluate the binding specificity of polypeptide 2A1 consisting of an amino acid sequence represented by SEQ ID NO: 11.

Polypeptide 2A1 (0.5 mg) was dissolved in 1.5 mL of a sodium carbonate buffer (0.2 M NaHCO3, 0.5 M NaCl, pH 8.3) and immobilized to NHS-activated Sepharose (registered trade mark) (0.1 mL) (GE Healthcare) by the amine coupling method in accordance with the procedure instructed in the accompanying manual. The reaction rate of immobilization was 42%. A solution containing contaminant proteins was prepared by suspending Escherichia coli BLT5403 strain, which was obtained by culturing in 1 mL-LB medium, in 1 mL of TBS-T buffer (50 mM Tris-HCl, 150 mM NaCl, 0.05% (w/v) Tween 20 (registered trade mark), pH 7.4), subjecting the suspension solution to ultrasonic grinding, and centrifuging to obtain the supernatant. A human Fc region having a non-native structure was prepared by dialyzing natural human Fc region against glycine hydrochloric acid buffer (10 mM Glycine-HCl, 150 mM NaCl, pH 2.0). The non-native Fc region (about 5 µg) was added to the above Escherichia coli ground solution (62 µL) and diluted with TBS-T buffer to obtain 1 mL of a solution. This was used as a sample solution for binding specificity evaluation. As a control solution for a comparison test, an Escherichia coli ground solution containing no non-native Fc region was prepared.

Figure 8:
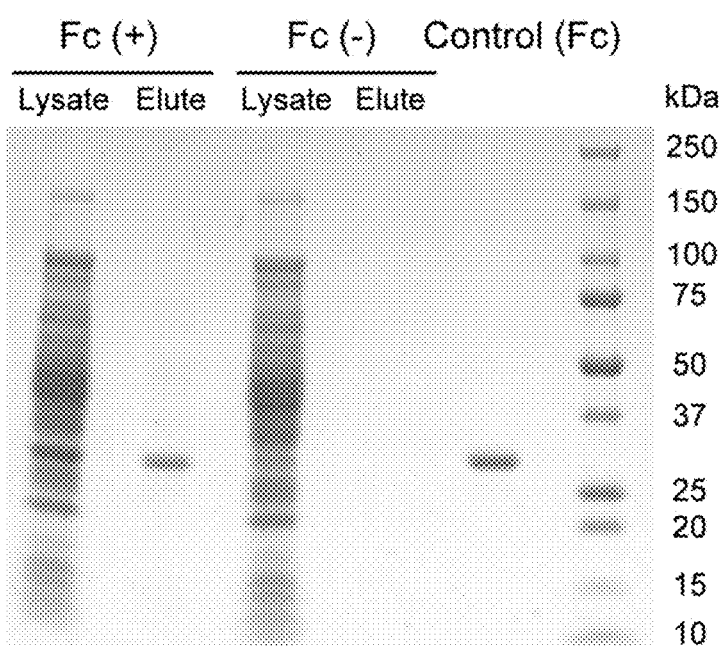
FIG. 8 shows evaluation of binding specificity by use of a 2A1 peptide immobilized resin; more specifically, shows the SDS polyacrylamide gel electrophoresis results of a sample solution (lysate) and elute in the presence of non-native Fc region (Fc (+)) and absence of non-native Fc region (Fc (−)), in which the control shows the band of an Fc region.

The sample solution prepared and Sepharose having 2A1 peptide immobilized thereto were mixed for 20 minutes. Thereafter, the mixture was washed five times with 0.5 mL of TBS-T buffer and eluted with 0.2 mL of 50 mM NaOH. The eluate was neutralized with 10 µL of 3 M sodium acetate (pH 5.2). The eluate and sample solution were analyzed by SDS polyacrylamide gel electrophoresis (FIG. 8). Only the band corresponding to an Fc region was significantly present in the eluate compared to other contaminant proteins. This result demonstrates that polypeptide 2A1 specifically recognizes a target Fc region from many contaminant proteins, in other words, that the molecule obtained by the present invention has a high target specificity as usually observed in interaction between proteins.

Example 7

In this Example, a complex of polypeptide p17 consisting of SEQ ID NO: 57 and an Fc region of human IgG was analyzed by X-ray crystal structural analysis and the conformation of the complex was determined. The analysis method and results will be described.

Polypeptide p17 was prepared in the same manner as in Example 2, 4). The Fc region of human IgG was prepared in the same manner as in Example 2, 1). A complex of polypeptide p17 and the Fc region was dialyzed against a buffer (20 mM Tris-HCl, 10% (v/v) dimethylsulfoxide, pH 7.4) and concentrated by ultrafiltration to a concentration of 10 mg/mL. A crystal was obtained by using a 40% polyethylene glycol 4000, 0.1 M sodium citrate (pH 5.6) and 0.2 M ammonium acetate as a precipitator/buffer for crystallization in accordance with a sitting-drop vapor diffusion method. The crystal obtained was subjected to diffraction in a high energy accelerator research institute, Photon Factory NW-12A and diffraction data were collected. Phase determination was performed by a molecular replacement method using a search model (Protein Data Bank (PDB) code, 1DN2). The structure of the crystal was accurately analyzed by CNS (Non Patent Literature 31 Brunger A T, Adams P D, Clore G M, DeLano W L, Gros P, Grosse-Kunstleve R W, Jiang J S, Kuszewski J, Nilges M, Pannu N S, Read R J, Rice L M, Simonson T, and Warren G L. (1998) Crystallography & NMR system: A new software suite for macromolecular structure determination. Acta Crystallogr D Biol Crystallogr. 54, 905-921), CCP4 suite (Non Patent Literature 32 Winn M D, Ballard C C, Cowtan K D, Dodson E J, Emsley P, Evans P R, Keegan R M, Krissinel E B, Leslie A G, McCoy A, McNicholas S J, Murshudov G N, Pannu N S, Potterton E A, Powell H R, Read R J, Vagin A and Wilson K S. (2011) Overview of the CCP4 suite and current developments. Acta Crystallogr D Biol Crystallogr. 67, 235-242) and Coot (Non Patent Literature 33 Emsley P and Cowtan K. (2004) Coot: model-building tools for molecular graphics. Acta Crystallogr D Biol Crystallogr. 60, 2126-2132). As a result, the crystal structure of the complex was determined at a resolution of 2.9 Å. Four complexes, i.e., four Fc regions and eight p17 molecules were contained in an asymmetric unit.

Figure 9:
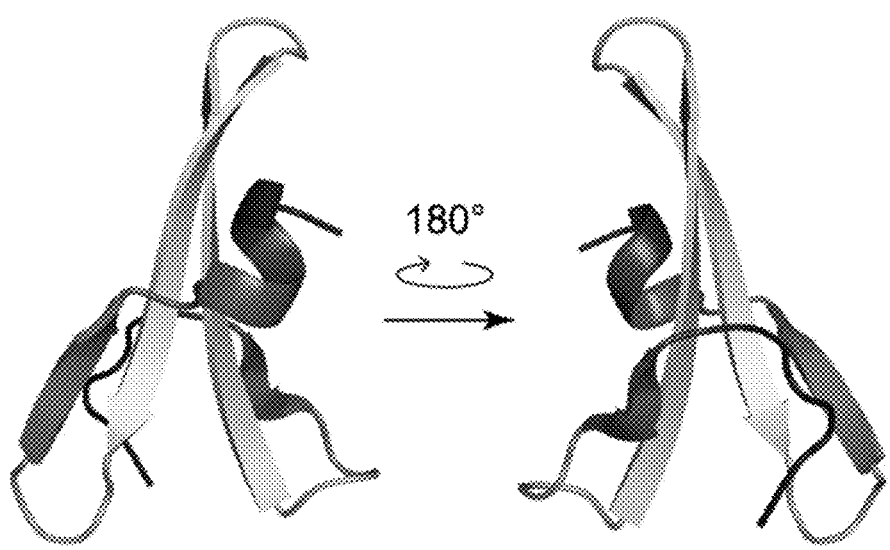
FIG. 9 shows ribbon models of a whole structure of polypeptide p17.
Figure 10:
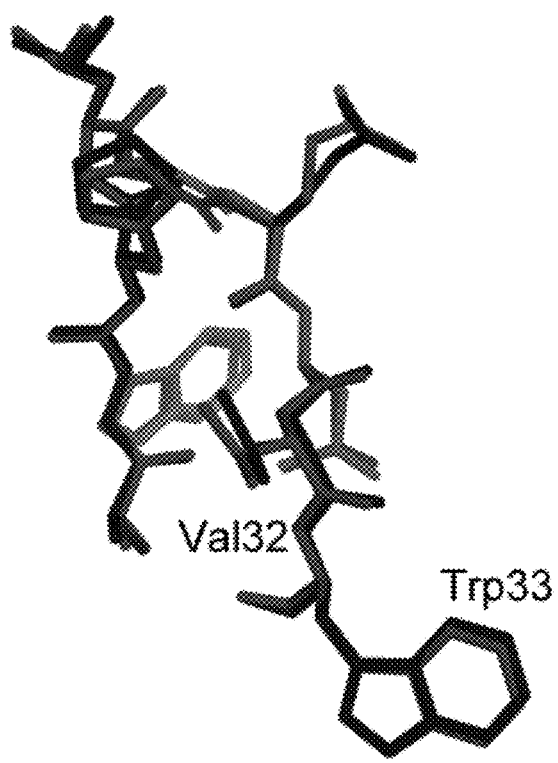
FIG. 10 shows superposition of polypeptide p17 and Fc III structures.
Figure 11:
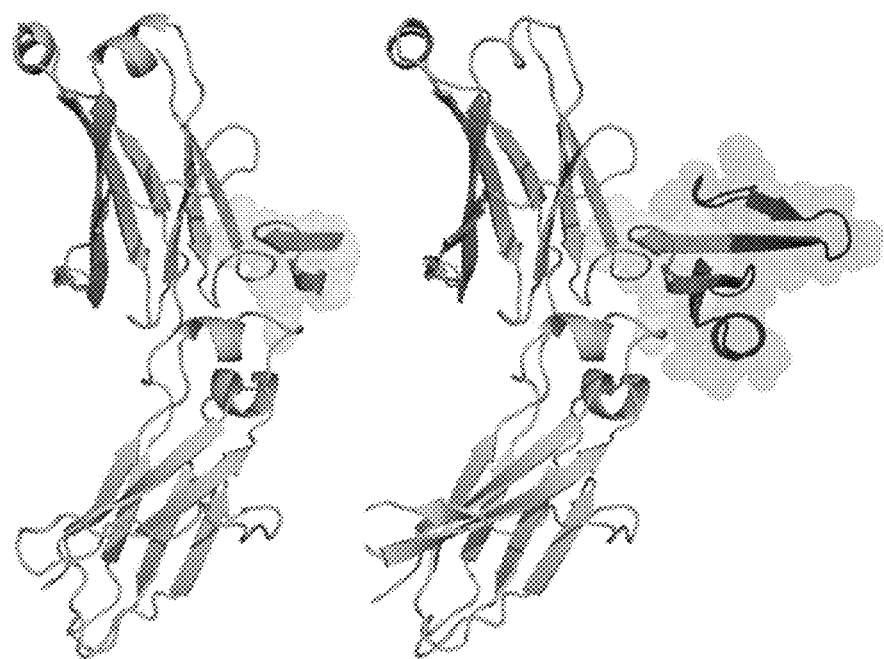
FIG. 11 (A) shows the structure of a complex of Fc III and an Fc region; and (B) shows a structure of a complex of polypeptide p17 and an Fc region.
Figure 12:
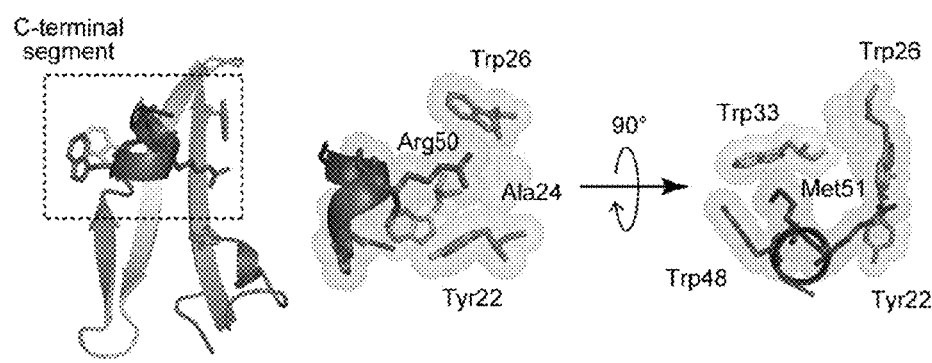
FIG. 12 (A) shows α helix formed of the C terminal segment; and (B) shows a loop structure formed of the N terminal segment.
Figure 12:
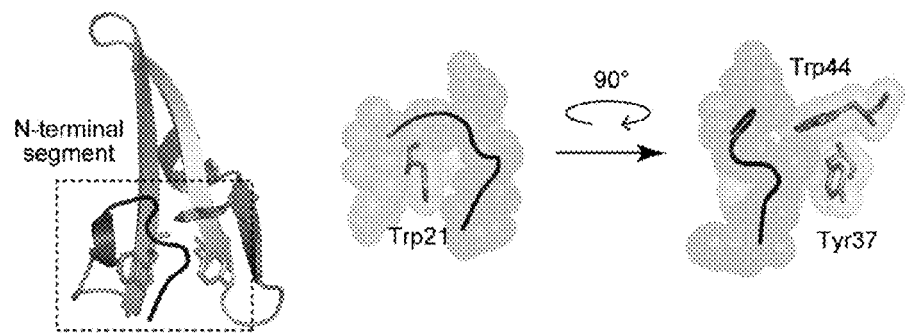

Polypeptide p17 was formed of four β strands, three β hairpins, a single short α helix and a single loop structure (FIG. 9). The Fc-III Ala portion contained in p17 exhibited high conformational homology with Fc III peptide used as a template (PDB code, 1DN2) with respect to both main chain and side chain structure (r.m.s.d.=0.639 Å) (FIG. 10) and recognized the same binding site to the Fc region (FIG. 11). This means that the function of the peptide of the present invention can be enhanced without damaging the specific function intrinsic to the peptide. The region derived from chignolin and introduced to the library had a β hairpin structure similarly to chignolin and played a role in arranging the region of extended random amino acid sequence to a position near Fc-III Ala. This means that two segments were effectively arranged closely to each other by use of a small protein forming a β hairpin. Two regions extended as random amino acid sequences formed totally different conformations. A C-terminal segment formed a short α helix structure, a side chain, which protruded from the surface of the helix structure, came into contact with an amino acid residue of Fc-III Ala and supported an advantageous conformation for binding (FIG. 12). A previous study suggests that the direction of a Trp residue is important in binding of an Fc III peptide used as a template to an Fc region (Non Patent Literatures 3 and 4). In Fc-III Ala, the aromatic ring residue of the corresponding Trp33 was directly supported by the side chain of Met51 present in the α helix (FIG. 12). In contrast to the C-terminal segment, the N terminal formed a loop structure and was in contact with the introduced chignolin portion corresponding to the base of Fc-III Ala to support the base (FIG. 12). These results show that the segments introduced as random amino acid sequences separately formed conformation suitable for individual surroundings as the result of functional selection and enhanced the function of the polypeptide.

Example 8

In this Example, it will be stated as an example that a variant was prepared by substituting an amino acid residue present in the C terminal segment of p17 polypeptide (SEQ ID NO: 57) with alanine and the effect of the amino acid residue on the binding activity was evaluated by measuring the binding activity and the role of the amino acid residue was more specifically analyzed in comparison with the conformation data obtained in Example 7.

DNA molecules (SEQ ID NOs: 179 to 183) encoding amino acid sequences represented by SEQ ID NOs: 174 to 178 were designed and synthesized by PCR. Thioredoxin fusion proteins were expressed and treated with protease in the same manner as in Example 2, 4) to prepare variant polypeptides, which were designated as follows: p17_P46A (SEQ ID NO: 174), p17_D47A (SEQ ID NO: 175), p17_W48A (SEQ ID NO: 176), p17_R50A (SEQ ID NO: 177) and p17_M51A (SEQ ID NO: 178).

Subsequently, the binding activity of five types of polypeptides prepared above was analyzed by surface plasmon resonance. Biacore T100 (GE Healthcare) was used in measurement. An Fc region was immobilized to Sensor Chip CM5 (GE Healthcare) and binding activity was analyzed in the same manner as in Example 2, 4). The binding activity values of the polypeptides obtained by the analysis are shown in Table 7. In all variants having a substitution with alanine, decrease of binding activity was confirmed, suggesting that these residues are involved in binding activity. Particularly, the binding activity values of p17_W48A and p17_M51A having an alanine substitution decreased 100 times or more. [Table 7]

TABLE 7

Equilibrium dissociation constant of p17 variant

| Variant | $K_D$ (nM) | SEQ ID NO: |
|---|---|---|
| p17_P46A | 5.6 | 174 |
| p17_D47A | 45 | 175 |
| p17_W48A | 200 | 176 |
| p17_R50A | 7.8 | 177 |
| p17_M51A | 180 | 178 |

Figure 13:
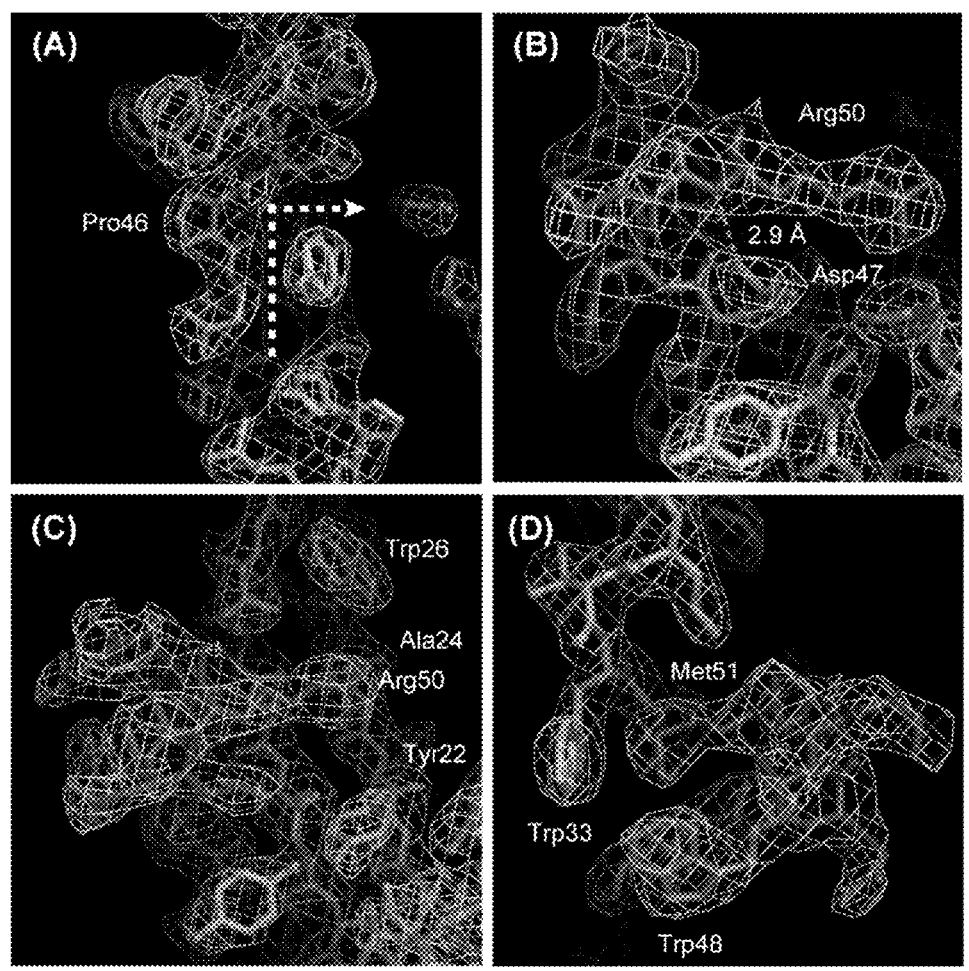
FIG. 13 shows electron density maps: (A) around Pro46, (B) around Asp47, (C) around Arg50 and (D) around Trp48 and Met51.

Next, the site substituted with alanine was discussed from a structural point of view. The direction of a main chain of the polypeptide is changed at a Pro46 site due to structural orientation specific to the proline residue, with the result that the direction of the α helix present upstream the site is slightly changed appropriately (FIG. 13A). Asp47 binds to Arg50 present in the proximity via a hydrogen bond (FIG. 13B) to thereby slightly control the direction of the α helix, in the same manner as Pro46. Arg50 present in the α helix, since its side chain is in contact with Ala24, assisted the crosslinkage between β strands of the 23 to 35 positions forming a binding site (FIG. 13C). Similarly, Trp48 and Met51 present in the α helix were in contact with each other (these hydrophobic residues are in contact with each other around Met51) to directly stabilize an aromatic ring of Trp33 present in the binding site (FIG. 13D). Previous studies (Non Patent Literatures 3 and 4) suggest that the direction of the aromatic ring side-chain of Trp33 has a large effect on binding to an Fc region. Furthermore, in the aforementioned binding activity test, it has been elucidated that the binding affinity of a peptide having an alanine substitution at Met51 reduces 100 times or more. Based on these two facts, it is considered that Met51 is involved in enhancing the binding activity by supporting the aromatic ring of Trp33.

The aforementioned results experimentally demonstrate that in the amino acid sequences randomly introduced in a molecular library, a functionally and structurally favorable amino acid residue is employed as a result of functional selection, with the result that the function of the resultant polypeptide can be effectively enhanced, based on not only binding function analysis but also conformational analysis.

All publications, patents and patent applications cited in the specification are incorporated in their entirety by reference.

INDUSTRIAL APPLICABILITY

The present invention is useful in detection, purification, immobilization or removal of proteins including antibodies.

SEQUENCE LIST FREE TEXT

SEQ ID NO: 1: IgG binding peptide
SEQ ID NO: 2: IgG binding peptide, H6
SEQ ID NO: 3: IgG binding peptide, H3
SEQ ID NO: 4: IgG binding peptide, D5
SEQ ID NO: 5: IgG binding peptide, E7
SEQ ID NO: 6: IgG binding peptide, sC12
SEQ ID NO: 7: IgG binding peptide, G3
SEQ ID NO: 8: IgG binding peptide, G11
SEQ ID NO: 9: IgG binding peptide, sA7
SEQ ID NO: 10: IgG binding peptide
SEQ ID NO: 11: IgG binding peptide, 2A1
SEQ ID NO: 12: IgG binding peptide, 2A4
SEQ ID NO: 13: IgG binding peptide, 2F12
SEQ ID NO: 14: IgG binding peptide, 2H1
SEQ ID NO: 15: IgG binding peptide, 2F2
SEQ ID NO: 16: IgG binding peptide, 2F4
SEQ ID NO: 17: IgG binding peptide, 2F6
SEQ ID NO: 18: IgG binding peptide, 2F7
SEQ ID NO: 19: IgG binding peptide, 2F9
SEQ ID NO: 20: IgG binding peptide
SEQ ID NO: 21: IgG binding peptide, 2A1Gly
SEQ ID NO: 22: IgG binding peptide, RSS
SEQ ID NO: 23: IgG binding peptide
SEQ ID NO: 24: IgG binding peptide, pep14
SEQ ID NO: 25: IgG binding peptide, pep11
SEQ ID NO: 26: IgG binding peptide, pep21
SEQ ID NO: 27: IgG binding peptide, pep24
SEQ ID NO: 28: IgG binding peptide, pep3
SEQ ID NO: 29: IgG binding peptide, pep9
SEQ ID NO: 30: IgG binding peptide, pep7
SEQ ID NO: 31: IgG binding peptide, pep25
SEQ ID NO: 32: IgG binding peptide, pep27
SEQ ID NO: 33: IgG binding peptide, pep31
SEQ ID NO: 34: IgG binding peptide, pep1
SEQ ID NO: 35: IgG binding peptide, pep2
SEQ ID NO: 36: IgG binding peptide, pep3
SEQ ID NO: 37: IgG binding peptide, pep4
SEQ ID NO: 38: IgG binding peptide, pep5
SEQ ID NO: 39: IgG binding peptide, pep6
SEQ ID NO: 40: IgG binding peptide, pep10
SEQ ID NO: 41: IgG binding peptide, pep12
SEQ ID NO: 42: IgG binding peptide, pep29
SEQ ID NO: 43: IgG binding peptide, pep15
SEQ ID NO: 44: IgG binding peptide, pep16
SEQ ID NO: 45: IgG binding peptide, pep17
SEQ ID NO: 46: IgG binding peptide, pep18
SEQ ID NO: 47: IgG binding peptide, pep19
SEQ ID NO: 48: IgG binding peptide, pep20
SEQ ID NO: 49: IgG binding peptide, pep22
SEQ ID NO: 50: IgG binding peptide, pep23
SEQ ID NO: 51: IgG binding peptide, pep26
SEQ ID NO: 52: IgG binding peptide, pep28
SEQ ID NO: 53: IgG binding peptide, pep29
SEQ ID NO: 54: IgG binding peptide, pep30
SEQ ID NO: 55: IgG binding peptide, pep11_2
SEQ ID NO: 56: IgG binding peptide
SEQ ID NO: 57: IgG binding peptide, p17
SEQ ID NO: 58: IgG binding peptide, p6
SEQ ID NO: 59: IgG binding peptide, p12
SEQ ID NO: 60: IgG binding peptide, p16
SEQ ID NO: 61: IgG binding peptide, p19
SEQ ID NO: 62: IgG binding peptide, p36
SEQ ID NO: 63: IgG binding peptide, p2_2
SEQ ID NO: 64: IgG binding peptide, p4
SEQ ID NO: 65: IgG binding peptide, p5
SEQ ID NO: 66: IgG binding peptide, p13
SEQ ID NO: 67: IgG binding peptide, p14
SEQ ID NO: 68: IgG binding peptide, p15_2
SEQ ID NO: 69: IgG binding peptide, p20
SEQ ID NO: 70: IgG binding peptide, p26
SEQ ID NO: 71: IgG binding peptide, p27
SEQ ID NO: 72: IgG binding peptide, p28
SEQ ID NO: 73: IgG binding peptide
SEQ ID NO: 74: IgG binding peptide, p2
SEQ ID NO: 75: IgG binding peptide, p15
SEQ ID NO: 76: IgG binding peptide, p24
SEQ ID NO: 77: IgG binding peptide, p25
SEQ ID NO: 78: IgG binding peptide, p34
SEQ ID NO: 79: IgG binding peptide, p24_2
SEQ ID NO: 80: IgG binding peptide, p25_2
SEQ ID NO: 81: IgG binding peptide, p31
SEQ ID NO: 82: Thioredoxin fusion protein, H6_trx
SEQ ID NO: 83: Thioredoxin fusion protein, 2A1_trx
SEQ ID NO: 84: Thioredoxin fusion protein, 2A4_trx
SEQ ID NO: 85: Thioredoxin fusion protein, 2F12_trx
SEQ ID NO: 86: Thioredoxin fusion protein, p17_trx
SEQ ID NO: 87: Thioredoxin fusion protein, pep14_trx
SEQ ID NO: 88: Thioredoxin fusion protein, pep21_trx
SEQ ID NO: 89: Thioredoxin fusion protein, pep24_trx
SEQ ID NO: 90: Thioredoxin fusion protein, pep3_trx
SEQ ID NO: 91: Thioredoxin fusion protein, pep9_trx
SEQ ID NO: 92: Thioredoxin fusion protein, pep7_trx
SEQ ID NO: 93: Thioredoxin fusion protein, pep25_trx
SEQ ID NO: 94: Thioredoxin fusion protein, pep27_trx
SEQ ID NO: 95: Thioredoxin fusion protein, pep31_trx
SEQ ID NO: 96: Thioredoxin fusion protein
SEQ ID NO: 97: Thioredoxin fusion protein, p2_trx
SEQ ID NO: 98: Thioredoxin fusion protein, p6_trx
SEQ ID NO: 99: Thioredoxin fusion protein, p12_trx
SEQ ID NO: 100: Thioredoxin fusion protein, p15_trx
SEQ ID NO: 101: Thioredoxin fusion protein, p16_trx
SEQ ID NO: 102: Thioredoxin fusion protein, p19_trx
SEQ ID NO: 103: Thioredoxin fusion protein, p24_trx
SEQ ID NO: 104: Thioredoxin fusion protein, p25_trx
SEQ ID NO: 105: Thioredoxin fusion protein, p34_trx
SEQ ID NO: 106: Thioredoxin fusion protein, p36_trx
SEQ ID NO: 107: Thioredoxin fusion protein, p2_2_trx
SEQ ID NO: 108: Thioredoxin fusion protein, p4_trx SEQ ID NO: 109: Thioredoxin fusion protein, p5_trx
SEQ ID NO: 110: Thioredoxin fusion protein, p13_trx
SEQ ID NO: 111: Thioredoxin fusion protein, p14_trx
SEQ ID NO: 112: Thioredoxin fusion protein, p15_2_trx
SEQ ID NO: 113: Thioredoxin fusion protein, p20_trx
SEQ ID NO: 114: Thioredoxin fusion protein, p24_2_trx
SEQ ID NO: 115: Thioredoxin fusion protein, p25_2_trx
SEQ ID NO: 116: Thioredoxin fusion protein, p26_trx
SEQ ID NO: 117: Thioredoxin fusion protein, p27_trx
SEQ ID NO: 118: Thioredoxin fusion protein, p28_trx
SEQ ID NO: 119: Thioredoxin fusion protein, p31_trx
SEQ ID NO: 120: Oligo DNA
SEQ ID NO: 121: Oligo DNA
SEQ ID NO: 122: Oligo DNA
SEQ ID NO: 123: Oligo DNA
SEQ ID NO: 124: Oligo DNA
SEQ ID NO: 125: Oligo DNA
SEQ ID NO: 126: Oligo DNA
SEQ ID NO: 127: Oligo DNA
SEQ ID NO: 128: Oligo DNA
SEQ ID NO: 129: Oligo DNA
SEQ ID NO: 130: Oligo DNA
SEQ ID NO: 131: Oligo DNA
SEQ ID NO: 132: Oligo DNA
SEQ ID NO: 133: Oligo DNA
SEQ ID NO: 134: Oligo DNA
SEQ ID NO: 135: Oligo DNA
SEQ ID NO: 136: Oligo DNA
SEQ ID NO: 137: Oligo DNA
SEQ ID NO: 138: Oligo DNA
SEQ ID NO: 139: Oligo DNA
SEQ ID NO: 140: Oligo DNA
SEQ ID NO: 141: Oligo DNA
SEQ ID NO: 142: Oligo DNA
SEQ ID NO: 143: Oligo DNA
SEQ ID NO: 144: Oligo DNA
SEQ ID NO: 145: Oligo DNA
SEQ ID NO: 146: Oligo DNA
SEQ ID NO: 147: Oligo DNA
SEQ ID NO: 148: Oligo DNA
SEQ ID NO: 149: Oligo DNA
SEQ ID NO: 150: Oligo DNA
SEQ ID NO: 151: Oligo DNA
SEQ ID NO: 152: Oligo DNA
SEQ ID NO: 153: Oligo DNA
SEQ ID NO: 154: Oligo DNA
SEQ ID NO: 155: Oligo DNA
SEQ ID NO: 156: Oligo DNA
SEQ ID NO: 157: Oligo DNA
SEQ ID NO: 158: IgG binding peptide, 2A1_Q5R
SEQ ID NO: 159: IgG binding peptide, 2A1_W6A
SEQ ID NO: 160: IgG binding peptide, 2A1_S7A
SEQ ID NO: 161: IgG binding peptide, 2A1_R17A
SEQ ID NO: 162: IgG binding peptide, 2A1_S18A
SEQ ID NO: 163: IgG binding peptide, 2A1_S19A
SEQ ID NO: 164: IgG binding peptide, 2A1_I20A
SEQ ID NO: 165: IgG binding peptide, Fc-III
SEQ ID NO: 166: IgG binding peptide
SEQ ID NO: 167: IgG binding peptide
SEQ ID NO: 168: IgG binding peptide library
SEQ ID NO: 169: Glycine linker
SEQ ID NO: 170: IgG binding peptide library
SEQ ID NO: 171: IgG binding peptide library
SEQ ID NO: 172: IgG binding peptide library
SEQ ID NO: 173: IgG binding peptide library
SEQ ID NO: 174: IgG binding peptide, p17_P46A
SEQ ID NO: 175: IgG binding peptide, p17_D47A
SEQ ID NO: 176: IgG binding peptide, p17_W48A
SEQ ID NO: 177: IgG binding peptide, p17_R50A
SEQ ID NO: 178: IgG binding peptide, p17_M51A
SEQ ID NO: 179: Oligo DNA
SEQ ID NO: 180: Oligo DNA
SEQ ID NO: 181: Oligo DNA
SEQ ID NO: 182: Oligo DNA
SEQ ID NO: 183: Oligo DNA

The invention claimed is:

1. A polypeptide exhibiting binding activity to an Fc region of immunoglobulin G, wherein the polypeptide comprises the amino acid sequence represented by the following formula 1:

```
                                    (SEQ ID NO: 1)
        Y-D-P-x-T-G-T-W-R-S-x-[IL] (1)
``` where x represents any amino acid residue; and amino acid residues within the square brackets indicate that any one of the amino acid residues is selected.

2. The polypeptide according to claim 1, consisting of:
   a) the amino acid sequence represented by formula 1;
   b) the amino acid sequence represented by any one of SEQ ID NOs: 2 to 6:

```
                                    (SEQ ID NO: 2)
        YDPRTGTWRSSIAYGGG (SEQ ID NO: 3)
        YDPGTGTWRSYLRFGGG (SEQ ID NO: 4)
        YDPYTGTWRSSIWVLSG (SEQ ID NO: 5)
        YDPGTGTWRSWLSFNVG (SEQ ID NO: 6)
        YDPWTGTWRSFIWGGGG;
        or
``` c) an amino acid sequence having addition of one or several amino acid residues in the amino acid sequence represented by any one of SEQ ID NOs: 2 to 6.

3. The polypeptide according to claim 1, consisting of the amino acid sequence represented by the following formula 2:

```
                                    (SEQ ID NO: 10)
        R-[QRS]-x-x-[GS]-Y-D-P-R-T-G-T-W-R-S-S-I-A-Y-
        G-G (2)
``` where x represents any amino acid residue; and amino acid residues within the square brackets indicate that any one of the amino acid residues is selected.

4. The polypeptide of claim 3, consisting of:
   a) the amino acid sequence represented by any one of SEQ ID NOs: 11 to 14;

```
                                    (SEQ ID NO: 11)
        GVVRQWSGYDPRTGTWRSSIAYGGG (SEQ ID NO: 12)
        AGSRRAHGYDPRTGTWRSSIAYGGG (SEQ ID NO: 13)
        ASVRSWSSYDPRTGTWRSSIAYGGG (SEQ ID NO: 14)
        SWRRRGSSYDPRTGTWRSSIAYGGG;
``` b) an amino acid sequence obtained by addition of one or several amino acid residues in the amino acid sequence represented by SEQ ID NOs: 11 to 14; or
   c) the amino acid sequence represented by any one of SEQ ID NOs: 15 to 19, 158-160 and 163:

```
                                    (SEQ ID NO: 15)
        TGRGRSARYDPRTGTWRSSIAYGGG (SEQ ID NO: 16)
        HWVNGRSGYDPRTGTWRSSIAYGGG (SEQ ID NO: 17)
        ERWITWSGYDPRTGTWRSSIAYGGG (SEQ ID NO: 18)
        GSVVRWRGYDPRTGTWRSSIAYGGG (SEQ ID NO: 19)
        GAVYRRSFYDPRTGTWRSSIAYRGG (SEQ ID NO: 158)
        GVVRRWSGYDPRTGTWRSSIAYGGG (SEQ ID NO: 159)
        GVVRQAQSGYDPRTGTWRSSIAYGGG (SEQ ID NO: 160)
        GVVRQWAGYDPRTGTWRSSIAYGGG (SEQ ID NO: 163)
        GVVRQWSGYDPRTGTWRSAIAYGGG.
```

5. A polypeptide exhibiting binding activity to an Fc region of immunoglobulin G, wherein the polypeptide is a tandem polypeptide formed by linking a second polypeptide to an amino terminal or a carboxyl terminal or both terminals of the polypeptide according to claim 1.

6. The polypeptide according to claim 5, which is a tandem polypeptide formed by linking a second polypeptide to an amino terminal or a carboxyl terminal or both terminals of the polypeptide of any one of SEQ ID NOs: 2 to 9, 11 to 19, 21, 22, 24 to 55, 57 to 81, 158 to 164 and 174 to 178.

7. A protein exhibiting binding activity to an Fc region of immunoglobulin G, wherein the protein is a fusion protein formed by binding a protein to the amino terminal or carboxyl terminal or both terminals of the polypeptide according to claim 1.

8. The protein according to tai claim 7, which is a fusion protein formed by binding a protein to the amino terminal or carboxyl terminal or both terminals of the polypeptide of any one of SEQ ID NOs: 2 to 9, 11 to 19, 21, 22, 24 to 55, 57 to 81, 158 to 164 and 174 to 178, or any one of SEQ ID NOs: 82 to 119.

9. A kit for detecting, purifying, immobilizing or removing an antibody, immunoglobulin G or a protein containing an Fc region of immunoglobulin G, comprising the polypeptide according to claim 1.

10. A polypeptide exhibiting binding activity to an Fc region of immunoglobulin G, wherein the polypeptide consists of the amino acid sequence represented by any one of SEQ ID NOs: 7 to 9:

```
                                   (SEQ ID NO: 7)
YDPRTGTWLLYASRLLG (SEQ ID NO: 8)
YDPVTGTWTSSIASWMG (SEQ ID NO: 9)
YDPRTGTWRRSSLSYSG.
```

11. A polypeptide exhibiting binding activity to an Fc region of immunoglobulin G, wherein the polypeptide consists of the amino acid sequence represented by any one of SEQ ID NOs: 15 to 19 and 158 to 164:

```
                                   (SEQ ID NO: 15)
TGRGRSARYDPRTGTWRSSIAYGGG (SEQ ID NO: 16)
HWVNGRSGYDPRTGTWRSSIAYGGG (SEQ ID NO: 17)
ERWITWSGYDPRTGTWRSSIAYGGG (SEQ ID NO: 18)
GSVVRWRGYDPRTGTWRSSIAYGGG (SEQ ID NO: 19)
GAVYRRSFYDPRTGTWRSSIAYRGG (SEQ ID NO: 158)
GVVRRWSGYDPRTGTWRSSIAYGGG (SEQ ID NO: 159)
GVVRQAQSGYDPRTGTWRSSIAYGGG (SEQ ID NO: 160)
GVVRQWAGYDPRTGTWRSSIAYGGG (SEQ ID NO: 161)
GVVRQWSGYDPRTGTWASSIAYGGG (SEQ ID NO: 162)
GVVRQWSGYDPRTGTWRASIAYGGG (SEQ ID NO: 163)
GVVRQWSGYDPRTGTWRSAIAYGGG (SEQ ID NO: 164)
GVVRQWSGYDPRTGTWRSSAAYGGG.
```

* * * * *